United States Patent
Chou et al.

(10) Patent No.: US 11,771,685 B2
(45) Date of Patent: Oct. 3, 2023

(54) COMPOUNDS FOR THE TREATMENT OF NEUROLOGICAL OR MITOCHONDRIAL DISEASES

(71) Applicant: MUSC FOUNDATION FOR RESEARCH DEVELOPMENT, Charleston, SC (US)

(72) Inventors: James C. Chou, Mt. Pleasant, SC (US); Sherine S. L. Chan, Charleston, SC (US); Richard A. Himes, Charleston, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 0 days.

(21) Appl. No.: 17/264,714

(22) PCT Filed: Jul. 29, 2019

(86) PCT No.: PCT/US2019/043868
§ 371 (c)(1),
(2) Date: Jan. 29, 2021

(87) PCT Pub. No.: WO2020/028222
PCT Pub. Date: Feb. 6, 2020

(65) Prior Publication Data
US 2022/0125774 A1 Apr. 28, 2022

Related U.S. Application Data

(60) Provisional application No. 62/711,575, filed on Jul. 29, 2018.

(51) Int. Cl.
*A61K 31/4406* (2006.01)
*A61P 25/08* (2006.01)
*A61K 31/136* (2006.01)
*A61K 31/18* (2006.01)

(52) U.S. Cl.
CPC ........ *A61K 31/4406* (2013.01); *A61K 31/136* (2013.01); *A61K 31/18* (2013.01); *A61P 25/08* (2018.01)

(58) Field of Classification Search
CPC .............................. A61P 25/08; A61K 31/136
See application file for complete search history.

(56) References Cited

U.S. PATENT DOCUMENTS

| 4,195,998 | A | 4/1980 | Adin et al. |
|---|---|---|---|
| 2013/0345312 | A1 | 12/2013 | Jankowski et al. |
| 2014/0031432 | A1 | 1/2014 | Jankowski et al. |
| 2015/0166476 | A1 | 6/2015 | Chen |
| 2015/0320702 | A1* | 11/2015 | Chou ............... A61P 25/00 514/655 |
| 2017/0283374 | A1 | 10/2017 | Borgstrom et al. |

FOREIGN PATENT DOCUMENTS

| CN | 101712648 | 11/2011 |
|---|---|---|
| CN | 102321084 | 3/2013 |
| CN | 104761568 | 7/2015 |
| KR | 1020140030786 | 3/2014 |
| WO | WO 1997/21432 | 6/1997 |
| WO | WO 2005/053609 | 6/2005 |
| WO | WO 2010/026592 | 3/2010 |
| WO | WO 2012/166862 | 12/2012 |
| WO | WO 2014/074976 | 5/2014 |
| WO | WO 2017/020030 | 2/2017 |

OTHER PUBLICATIONS

Journal of Organic Chemistry (2014) 79:4553-4560) (Year: 2014).*
Afrikanova et al., "Validation of the zebrafish pentylenetetrazol seizure model: locomotor versus electrographic responses to antiepileptic drugs," PLoS One. 2013;8(1):e54166. Epub Jan. 24, 2013. doi: 10.1371/journal.pone.0054166. PubMed PMID: 23342097; PubMed Central PMCID: PMC3544809.
Allison, "The possible role of vitamin K deficiency in the pathogenesis of Alzheimer's disease and in augmenting brain damage associated with cardiovascular disease," Med Hypotheses. 2001;57(2):151-5. Epub Jul. 20, 2001. doi: 10.1054/mehy.2001.1307. PubMed PMID: 11461163.
Alsdorf and Wyszynski, "Teratogenicity of sodium valproate," Expert Opin Drug Saf. 4(2):345-53, 2005.
Amini et al. "A Molecular Approach to Epilepsy Management: from Current Therapeutic Methods to Preconditioning Efforts," Mol Neurobiol. 2015;52(1):492-513. doi: 10.1007/s12035-014-8876-5. PubMed PMID: 25195699.
Andreux et al., "Pharmacological approaches to restore mitochondrial function," Nat Rev Drug Discov. 12(6):465-83; 2013.
Andreux et al., "A method to identify and validate mitochondrial modulators using mammalian cells and the worm C. elegans," Sci Rep; 4:5285; 2014.
Artuso et al., "Mitochondrial DNA metabolism in early development of zebrafish (Danio rerio)," Biochim Biophys Acta.;1817(7):1002-11, 2012.
Baraban et al., "Pentylenetetrazole induced changes in zebrafish behavior, neural activity and c-fos expression," Neuroscience. 2005;131(3):759-68. Epub Feb. 26, 2005. doi: S0306-4522(04)01079-6 [pii].
Barton et al., "Pharmacological characterization of the 6 Hz psychomotor seizure model of partial epilepsy," Epilepsy Res. 2001;47(3):217-27. PubMed PMID: 11738929.
Bindoff and Engelsen, "Mitochondrial cytopathies," In: Andermann F, Guerrini R, Shorvon SD, editors. The Causes of Epilepsy: Common and Uncommon Causes in Adults and Children. Cambridge: Cambridge University Press, p. 147-57, 2011.

(Continued)

*Primary Examiner* — Marcos L Sznaidman
(74) *Attorney, Agent, or Firm* — Parker Highlander PLLC

(57) ABSTRACT

Compounds and methods are provided for the treatment of neurological or mitochondrial diseases, including epilepsy. In some embodiments, the compounds are substituted 1,4-naphthoquinones.

5 Claims, 5 Drawing Sheets

(56) References Cited

OTHER PUBLICATIONS

Bindoff and Engelsen, "Mitochondrial diseases and epilepsy," Epilepsia. 53:92-7, 2012.
Booth et al., "Response of vitamin K status to different intakes and sources of phylloquinone-rich foods: comparison of younger and older adults," Am J Clin Nutr. 1999;70(3):368-77. Epub Sep. 9, 1999. PubMed PMID: 10479199.
Booth et al., "Age and dietary form of vitamin K affect menaquinone-4 concentrations in male Fischer 344 rats," J Nutr. 2008;138(3):492-6. Epub Feb. 22, 2008. PubMed PMID: 18287355.
Carrie et al., "Lifelong low-phylloquinone intake is associated with cognitive impairments in old rats," J Nutr. 2011;141(8):1495-501. Epub Jun. 10, 2011. doi: 10.3945/jn.110.137638. PubMed PMID: 21653572.
Cheng et al., "Retinoic acid protects against proteasome inhibition associated cell death in SH-SY5Y cells via the AKT pathway," Neurochem Int.; 62(1):31-42, 2013.
Da Cruz et al., "1,2,3-Triazole-, arylamino- and thio-substituted 1,4-naphthoquinones: Potent antitumor activity, electrochemical aspects, and bioisosteric replacement of C-ring-modified lapachones," Bioorganic and Medicinal Chemistry, 22(5):1608-1619, 2014.
Da Cruz et al., "Synthesis and antitumor activity of selenium-containing quinone-based triazoles possessing two redox centres, and their mechanistic insights," European Journal of Medicinal Chemistry, 122:1-16, 2016. doi: 10.1016/j.ejmech.2016.06.019.
Da Silva et al., "Synthesis of N-substituted phthalimidoalkyl 1H-1,2,3-triazoles: a molecular diversity combining click chemistry and ultrasound irradiation," Journal of the Brazilian Chemical Society, 23(10):1839-1843, 2012.
Diogo et al., "Synthesis and anti-Trypanosoma cruzi activity of naphthoquinone-containing triazoles: Electrochemical studies on the effects of the quinoidal moiety," Bioorganic and Medicinal Chemistry, 21(21):6337-6348, 2013.
Fei et al., "CuCl2-Promoted 6-endo-dig Chlorocyclization and Oxidative Aromatization Cascade: Efficient Construction of 1-Azaanthraquinones from N-Propargylaminoquinones," Organic Letters, 13(16):4208-4211, 2011.
Fieser, "The alkylation of hydroxynaphthoquinone I. Ortho-ethers," J Am Chem Soc. 48(11):2922-37, 1926.
Finsterer and Scorza, "Effects of antiepileptic drugs on mitochondrial functions, morphology, kinetics, biogenesis, and survival," Epilepsy Res. 136:5-11, 2017.
Finsterer and Segall, "Drugs interfering with mitochondrial disorders," Drug Chem Toxicol. 33(2):138-5, 2010.
Franco et al., "Challenges in the clinical development of new antiepileptic drugs," Pharmacol. Res.; 103:95-104, 2016.
Gano et al., "Ketogenic diets, mitochondria, and neurological diseases," J Lipid Res. 2014;55(11):2211-28. doi: 10.1194/jlr.R048975. PubMed PMID: 24847102; PubMed Central PMCID: PMCPMC4617125.
Gornostaev et al., "Synthesis of 13-alkylbenzo[f]isochromeno[4,3-b]indole-5,7,12(13H)-triones by reaction of 2-alkylamino-1,4-naphthoquinones with ninhydrin," Russian Journal of Organic Chemistry; 52(1):80-6, 2016.
Hansen et al., "Anticonvulsant and antiepileptogenic effects of GABAA receptor ligands in pentylenetetrazole-kindled mice," Prog. Neuropsychopharmacol. Biol. Psychiatry. 2004;28(1):105-13. Epub Feb. 23, 2003. doi: 10.1016/j.pnpbp.2003.09.026. PubMed PMID: 14687864.
Hanson et al., "Synthesis and evaluation of 11β-(4-Substituted phenyl) estradiol analogs: Transition from estrogen receptor agonists to antagonists," Bioorganic and Medicinal Chemistry, 20(12):3768-3780, 2012.
Hirota et al. "Menadione (vitamin K3) is a catabolic product of oral phylloquinone (vitamin K1) in the intestine and a circulating precursor of tissue menaquinone-4 (vitamin K2) in rats," J Biol Chem. 2013;288(46):33071-80. Epub Oct. 3, 2013. doi: 10.1074/jbc.M113.477356. PubMed PMID: 24085302; PubMed Central PMCID: PMC3829156.
Hoffmann et al., "Increase in antiepileptic efficacy during prolonged treatment with valproic acid: role of inhibition of histone deacetylases?" Epilepsy Res. 2008;81(2-3):107-13. Epub Jun. 10, 2008. doi: 10.1016/j.eplepsyres.2008.04.019. PubMed PMID: 18538545.
Howe et al., "The zebrafish reference genome sequence and its relationship to the human genome," Nature; 496(7446):498-503, 2013.
Jiang et al., "Azaanthraquinone Assembly from N-Propargylamino-Quinone via a Au(I)-Catalyzed 6-endo-dig Cycloisomerization," Journal of Organic Chemistry, 75912):4323-4325, 2010.
Johannessen and Johannessen, "Valproate: past, present, and future," CNS Drug Rev. 2003;9(2):199-216. Epub Jul. 9, 2003. PubMed PMID: 12847559.
Josey et al., "Structure-activity relationship study of vitamin k derivatives yields highly potent neuroprotective agents," *Journal of Medicinal Chemistry*, 56:1007-1022, 2013.
Kohlmeier et al., "Transport of vitamin K to bone in humans," J Nutr. 1996;126(4 Suppl):1192S-6S. Epub Apr. 1, 1996. PubMed PMID: 8642455.
Koppel et al., "Neuroketotherapeutics: A modern review of a century-old therapy," Neurochem Int. 2017. doi: 10.1016/j.neuint.2017.05.019. PubMed PMID: 28579059.
Kumar et al., "Synthesis of pharmacologically important naphthoquinones and anticancer activity of 2-benzyllawsone through DNA topoisomerase-II inhibition," Bioorg Med Chem. 25(4):1364-73, 2017.
Lheureux and Hantson, "Carnitine in the treatment of valproic acid-induced toxicity," Clin Toxicol (Phila). 2009;47(2):101-11. Epub Mar. 13, 2009. doi: 909432124 [pii] 10.1080/15563650902752376. PubMed PMID: 19280426.
Lien et al., "eSynthesis of 2-alkoxy 1,4-naphthoquinone derivatives as antiplatelet, antiinflammatory, and antiallergic agents," Chem. Pharm. Bull. (Tokyo). 50(5):672-4, 2002.
Loscher et al., "New avenues for anti-epileptic drug discovery and development," Nat. Rev. Drug Discov., 12(10):757-76, 2013.
Matagne and Klitgaard, "Validation of corneally kindled mice: a sensitive screening model for partial epilepsy in man," Epilepsy Res; 31(1):59-71, 1998.
Metcalf et al., "Development and pharmacologic characterization of the rat 6 Hz model of partial seizures," Epilepsia. 2017;58(6):1073-84. doi: 10.1111/epi.13764. PubMed PMID: 28449218; PubMed Central PMCID: PMCPMC5469205.
Milton et al., "Rational design of quinones for high power density biofuel cells," Chem Sci. 6(8):4867-75, 2015.
Minor et al., "Chronic ingestion of 2-deoxy-D-glucose induces cardiac vacuolization and increases mortality in rats," Toxicol Appl Pharmacol. 2010;243(3):332-9. doi: 10.1016/j.taap.2009.11.025. PubMed PMID: 20026095; PubMed Central PMCID: PMCPMC2830378.
Mula, "Investigational new drugs for focal epilepsy," Expert Opin Investig Drugs. 2016;25(1):1-5. doi: 10.1517/13543784.2016.1110144. PubMed PMID: 26535466.
Nadanaciva et al., "Toxicity assessments of nonsteroidal anti-inflammatory drugs in isolated mitochondria, rat hepatocytes, and zebrafish show good concordance across chemical classes," Toxicol Appl Pharmacol., 272:272-280, 2013.
Neal et al., "The ketogenic diet for the treatment of childhood epilepsy: a randomised controlled trial," Lancet Neurol. 2008;7(6):500-6. doi: 10.1016/S1474-4422(08)70092-9. PubMed PMID: 18456557.
Noebels et al., Jasper's Basic Mechanisms of the Epilepsies. 4th edition ed. Bethesda (MD): National Center for Biotechnology Information (US); 2012.
Nogueira et al., "Syndromes associated with mitochondrial DNA depletion." Ital. J. Pediatr., 40:34, 10 pages, 2014.
Ogata et al., "Unusual, chemoselective etherification of 2-hydroxy-1,4-naphthoquinone derivatives utilizing alkoxymethyl chlorides: scope, mechanism and application to the synthesis of biologically active natural product (±)-lantalucratin C," Tetrahedron, 72(11):1423-32, 2016.
Ohlow et al., "Why Have Clinical Trials of Antioxidants to Prevent Neurodegeneration Failed?—A Cellular Investigation of Novel

(56) References Cited

OTHER PUBLICATIONS

Phenothiazine-Type Antioxidants Reveals Competing Objectives for Pharmaceutical Neuroprotection," Pharm Res. 34(2):378-93, 2017.
PCT International Invitation to Pay Additional Fees issued in International Application No. PCT/US2019/043868, dated Oct. 1, 2019.
PCT International Search Report and Written Opinion issued in International Application No. PCT/US2019/043868, dated Dec. 3, 2019.
Peng et al., "Improved pharmacokinetic and bioavailability support of drug discovery using serial blood sampling in mice," Journal of Pharmaceutical Sciences, 98(5):1877-84, 2009.
Perucca, "Pharmacological and therapeutic properties of valproate: a summary after 35 years of clinical experience," CNS Drugs. 2002;16(10):695-714. Epub Sep. 25, 2002. doi: 161004 [pii]. PubMed PMID: 12269862.
Phiel et al., Histone deacetylase is a direct target of valproic acid, a potent anticonvulsant, mood stabilizer, and teratogen, J Biol Chem. 2001;276(39):36734-41. Epub Jul. 27, 2001. doi: 10.1074/jbc.M101287200. PubMed PMID: 11473107.
Porta et al., "Fenofibrate, a peroxisome proliferator-activated receptor-alpha agonist, exerts anticonvulsive properties," Epilepsia. 2009;50(4):943-8. Epub Dec. 5, 2008. doi: 10.1111/j.1528-1167.2008.01901.x. PubMed PMID: 19054409.
Poteet et al., "Neuroprotective actions of methylene blue and its derivatives," PLoS One, 7(10):e48279, 2012.
Presse et al., "Vitamin K status and cognitive function in healthy older adults," Neurobiol Aging. 2013;34(12):2777-83. Epub Jul. 16, 2013. doi: 10.1016/j.neurobiolaging.2013.05.031. PubMed PMID: 23850343.
Presse et al., "Low vitamin K intakes in community-dwelling elders at an early stage of Alzheimer's disease," J Am Diet Assoc. 2008;108(12):2095-9. Epub Nov. 26, 2008. doi: 10.1016/j.jada.2008.09.013. PubMed PMID: 19027415.
Rahn et al., "Novel Vitamin K analogs suppress seizures in zebrafish and mouse models of epilepsy," Neuroscience, 259:142-154, 2014. doi: 10.1016/j.neuroscience.2013.11.040.
Reagan-Shaw et al., "Dose translation from animal to human studies revisited," FASEB J., 22(3):659-661, 2008.
Rogawski and Loscher, "The neurobiology of antiepileptic drugs for the treatment of nonepileptic conditions," Nat Med. 2004;10(7):685-92. Epub Jul. 2, 2004. doi: 10.1038/nm1074. PubMed PMID: 15229516.
Rowley and White, "Comparative anticonvulsant efficacy in the corneal kindled mouse model of partial epilepsy: Correlation with other seizure and epilepsy models," Epilepsy Res. 2010;92(2-3):163-9. doi: 10.1016/j.eplepsyres.2010.09.002. PubMed PMID: 20951004.
Rowley and Patel, "Mitochondrial involvement and oxidative stress in temporal lobe epilepsy," Free Radic Biol Med. 2013;62:121-31. doi: 10.1016/j.freeradbiomed.2013.02.002. PubMed PMID: 23411150; PubMed Central PMCID: PMCPMC4043127.
Shearer and Newman, "Recent trends in the metabolism and cell biology of vitamin K with special reference to vitamin K cycling and MK-4 biosynthesis," J Lipid Res. 2014;55(3):345-62. Epub Feb. 4, 2014. doi: 10.1194/jlr.R045559. PubMed PMID: 24489112; PubMed Central PMCID: PMC3934721.
Sreelatha et al., "Synthesis and SAR study of novel anticancer and antimicrobial naphthoquinone amide derivatives," Bioorg Med Chem Lett.; 24(15):3647-51, 2014.
Stables et al., "Therapy discovery for pharmacoresistant epilepsy and for disease-modifying therapeutics: summary of the NIH/NINDS/AES models II workshop," Epilepsia. 2003;44(12):1472-8. PubMed PMID: 14636315.
Stenger et al., "Efficacy of a ketogenic diet in resistant myoclono-astatic epilepsy: A French multicenter retrospective study," Epilepsy Res. 2017;131:64-9. doi: 10.1016/j.eplepsyres.2017.02.005. PubMed PMID: 28273610.
Stewart et al., "Polymerase gamma gene POLG determines the risk of sodium valproate-induced liver toxicity," Hepatology. 52(5):1791-6, 2010.
Suja et al., "Copper-catalyzed three-component synthesis of aminonaphthoquinone-sulfonylamidine conjugates and in vitro evaluation of their antiproliferative activity," Bioorganic & Medicinal Chemistry Letters, 26(8):2072-2076, 2016. doi: 10.1016/j.bmcl.2016.02.071.
Tan et al., "Tridecanoin is anticonvulsant, antioxidant, and improves mitochondrial function," J. Cereb. Blood Flow Metab. 2017. 37(6):2035-48. doi: 10.1177/0271678X16659498. PubMed PMID: 27418037; PubMed Central PMCID: PMCPMC5464699.
Tandon et al., "Synthesis and evaluation of novel 1,4-naphthoquinone derivatives as antiviral, antifungal and anticancer agents," Bioorg. Med. Chem. Lett., 14(11):2901-4, 2004.
Thijssen et al., "Phylloquinone and menaquinone-4 distribution in rats: synthesis rather than uptake determines menaquinone-4 organ concentrations," J. Nutr. 1996. 126(2):537-43. Epub Feb. 1, 1996. PubMed PMID: 8632229.
Thijssen and Drittij-Reijnders, "Vitamin K status in human tissues: tissue-specific accumulation of phylloquinone and menaquinone-4," Br J Nutr. 1996;75(1):121-7. Epub Jan. 1, 1996. PubMed PMID: 8785182.
Tobaben et al., "Bid-mediated mitochondrial damage is a key mechanism in glutamate-induced oxidative stress and AIF-dependent cell death in immortalized HT-22 hippocampal neurons," Cell Death Differ. 18(2):282-92, 2011.
Vafai et al., "Natural Product Screening Reveals Naphthoquinone Complex I Bypass Factors," PLoS One; 11(9):e0162686, 2016.
Valente et al., "The 1,4-naphthoquinone scaffold in the design of cysteine protease inhibitors," Bioorg Med Chem. 15(15):5340-50, 2007.
Vining et al., "A multicenter study of the efficacy of the ketogenic diet," Arch Neurol. 1998;55(11):1433-7. PubMed PMID: 9823827.
Vos et al., "Vitamin K2 is a mitochondrial electron carrier that rescues pink1 deficiency," Science. 2012;336(6086):1306-10. Epub May 5, 2012. doi: 10.1126/science.1218632. PubMed PMID: 22582012.
Wang et al., "Naphthoquinone-directed C—H annulation and C(sp(3))-H bond cleavage: one-pot synthesis of tetracyclic naphthoxazoles," J. Org. Chem. 79(10):4553-60, 2014.
Wang et al., "Synthesis and Biological Evaluation of Lipophilic 1,4-Naphthoquinone Derivatives against Human Cancer Cell Lines," Molecules. 20(7):11994-2015, 2015.
Wen et al., "Alternative mitochondrial electron transfer as a novel strategy for neuroprotection," J. Biol. Chem. 286(18):16504-15, 2011.
Wheless, "History of the ketogenic diet," Epilepsia. 2008;49 Suppl 8:3-5. doi: 10.1111/j.1528-1167.2008.01821.x. PubMed PMID: 19049574.
Yang et al., "The excitatory neurotransmitter glutamate stimulates DNA repair to increase neuronal resiliency," Mech Ageing Dev. 132(8-9):405-11, 2011.
Yin et al., "Assembly of pentacyclic pyrido[4,3,2-mn]acridin-8-ones via a domino reaction initiated by Au(I)-catalyzed 6-endo-dig cycloisomerization of N-propargylaminoquinones," Tetrahedron Letters, 53(52):7078-7082, 2012.
Zaccara and Schmidt, "Do traditional anti-seizure drugs have a future? A review of potential anti-seizure drugs in clinical development," Pharmacol. Res. 2016;104:38-48. doi: 10.1016/j.phrs.2015.12.011. PubMed PMID: 26689774.
Zsurka and Kunz, "Mitochondrial dysfunction and seizures: the neuronal energy crisis," Lancet Neurol. 2015;14(9):956-66. doi: 10.1016/81474-4422(15)00148-9. PubMed PMID: 26293567.
Partial European Search Report issued in International Application No. PCT/US2019043868, dated Mar. 30, 2022.
Fei et al., "Azaanthraquinone assembly from N-propargylamino quinone via iodine-induced 6-endo-digelectrophilic cyclization," Org Biomol Chem., 8(18):4096-103, 2010.

* cited by examiner

COMPOUNDS FOR THE TREATMENT OF NEUROLOGICAL OR MITOCHONDRIAL DISEASES

This application is a national phase application under 35 U.S.C. § 371 of International Application No. PCT/US2019/043868, filed Jul. 29, 2019, which claims the benefit of U.S. Provisional Patent Application No. 62/711,575, filed Jul. 29, 2018, the entirety of each of which is hereby incorporated by reference.

This invention was made with government support under Grant No. NS097047-01, ES015555, RR024485, GM103542, and RR029882 awarded by the National Institutes of Health. The government has certain rights in the invention.

BACKGROUND OF THE INVENTION

1. Field of the Invention

The present invention relates generally to the field of chemistry and medicine. More particularly, it concerns compounds that may be used, e.g., for the treatment of neuronal disorders such as epilepsy.

2. Description of Related Art

Epilepsy is a widespread, debilitating disease with treatments that suffer from poor adherence, adverse side effects, or even inefficacy in patients with various forms of medication-resistance epilepsy. Epilepsy is affects approximately 1-2% of the world's population and is characterized by the periodic and unpredictable occurrence of seizures (Bialer and White 2010).

The more than 25 anti-epileptic drugs (AEDs) on the market suffer several drawbacks, including side effects and adverse drug interactions that can lead to decreased patient quality of life and poor treatment adherence (Franco et al. 2016; Loscher et al.). For example, commonly prescribed valproic acid (VPA), a broad-spectrum AED used to treat all forms of seizures (Perucca E. 2002), is generally well tolerated but requires high therapeutic doses and is associated with several side effects: acute hepatic failure, pancreatitis and teratogenesis (Lheureux and Hantson, 2009). Thus, VPA is contra-indicated for young children (Stewart et al. 2010) and pregnant women (Alsdorf and Wyszynski, 2005), and can induce rapid decline in health in mitochondrial disease patients (Finsterer and Segall, 2010). Some more recently generated AEDs display lowered toxicity and fewer adverse drug interactions but are only marginally (if at all) more efficacious than older drugs (Loscher and Schmidt, 2011).

Medication-resistant epilepsy presents a particularly difficult clinical problem. Indeed, ~40% of patients experience medication-resistant epilepsy, which no currently marketed drug has been shown to control (Loscher and Schmidt, 2011; Mohanraj and Brodie, 2005). These patients include up to 90% of pediatric patients with medication-resistant epilepsies due to genetic mitochondrial disorders, such as mitochondrial DNA depletion syndrome (MDS) (Finsterer and Scorza, 2017).

A poor understanding of how to target the underlying causes of epilepsy impedes therapeutic breakthroughs (Bindoff and Engelsen, 2011; Bindoff and Engelsen, 2012; Loscher et al., 2013; Noebels et al. 2012). Additionally, previously identified compounds that have displayed encouraging results in vitro have often displayed poor pharmacokinetic profiles, limiting their potential for use as an anti-epilepsy drug (AED) (Rahn et al., 2013). Despite the fact that mitochondrial dysfunction is a major underlying cause of epilepsy, there are currently no AEDs for clinical use that target mitochondrial health and energetics. Clearly, there is a need for new compounds for the treatment of epilepsy and medication resistant epilepsy.

SUMMARY OF THE INVENTION

The present invention, in certain aspects, overcomes limitations in the prior art by providing compounds that may be used for the treatment of neurological or metabolic diseases such as, e.g., epilepsy or medication-resistant epilepsy. In some embodiments, and as shown in in vivo experiments in the below examples, compounds are provided herein that display improved anti-seizure activity and improved pharmacokinetic properties. In some embodiments, compounds are provided that resulted in improved efficacy and drug-like properties; for example, inclusion of a 2-pentynylamine substituent or an isoamyloxy group on an 1,4-naphthoquinone scaffold resulted in significant improvements in anti-seizure activity in zebrafish and improved pharmacokinetic properties in mice.

In some aspects, the present disclosure provides methods of treating a neurological disease or a mitochondrial disease in a mammalian subject comprising administering to a subject a therapeutically effective dose of a pharmaceutical composition comprising a compound of the formula:

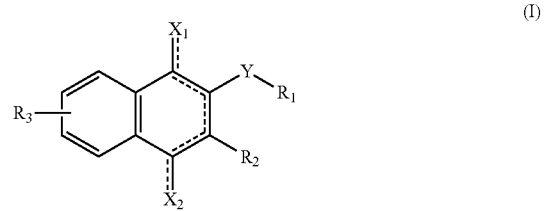

(I)

wherein:
$X_1$ and $X_2$ are each independently oxo or hydroxy;
$R_2$ is hydrogen, $C_{1-6}$ alkyl, $C_{6-12}$ aryl, $C_{5-12}$ heteroaryl, $C_{1-6}$ alkanediyl-$C_{6-12}$ aryl, —NH—CO—$C_{6-12}$ aryl, —$C_{1-4}$alkanediyl-O—$C_{6-12}$ aryl, halogen, or a substituted version thereof;
$R_3$ is hydrogen, amino, cyano, halo, hydroxy, nitro, aminosulfonyl, hydroxysulfonyl, $C_{1-6}$ alkyl, $C_{1-6}$ acyl, $C_{1-6}$ alkoxy, $C_{1-6}$ alkylamino, $C_{1-8}$ dialkylamino, or a substituted version of any of the last five groups;
Y is —NH— or —O—;
wherein when Y is —NH— and $R_2$ is hydrogen,
$R_1$ is $C_{1-8}$ alkyl, $C_{6-18}$ alkenyl, or $C_{6-12}$ aryl; —$(CH_2)_xC\equiv CR_a$; wherein: x is 1, 2, 3, or 4 and $R_a$ is $C_{1-8}$ alkyl, $C_{1-8}$ alkenyl, $C_{1-8}$ alkynyl, $C_{6-12}$ aryl, $C_{1-12}$ heteroaryl, or a substituted version of any of these groups;
a group of the formula:

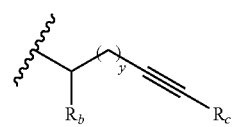

wherein:
  $R_b$ is $C_{1-8}$ alkyl, substituted $C_{1-8}$ alkyl, $C_{6-12}$ aryl, substituted $C_{6-12}$ aryl, or —C(O)$R_d$;
    wherein: $R_d$ is amino, hydroxy, —NHNH$_2$, $C_{1-6}$ alkoxy, $C_{1-6}$ alkylamino, or $C_{1-8}$ dialkylamino, or a substituted version of any of the last three groups; or
  $R_e$ is hydrogen, $C_{1-8}$ alkyl, $C_{1-8}$ alkenyl, $C_{1-8}$ alkynyl, $C_{6-12}$ aryl, $C_{1-12}$ heteroaryl, or a substituted version of any of the last five groups; and
  y is 0, 1, or 2; or
a group of the formula:

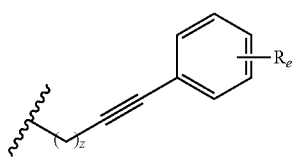

wherein:
  z is 1, 2, or 3
  $R_e$ is halo, $C_{1-6}$ alkyl, $C_{1-6}$ alkoxy, $C_{1-6}$ alkylsulfonylamino, or a substituted version of any of the last three groups; or
a group of the formula:

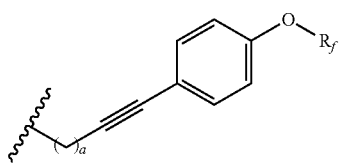

wherein:
  a is 1, 2, or 3
  $R_f$ is $C_{6-12}$ aryl, $C_{7-12}$ aralkyl, or a substituted version of any of either groups;
wherein when Y is —NH— and $R_2$ is not hydrogen; then:
  $R_1$ is $C_{1-12}$ alkyl, $C_{6-12}$ alkenyl, $C_{6-12}$ alkynyl, $C_{6-12}$ aryl, $C_{1-12}$ heteroaryl, or a substituted version of any of these groups, or —Y'—X$_3$—R$_g$, wherein:
    Y' is $C_{1-6}$ alkynediyl, $C_{6-12}$ arenediyl, or a substituted version of either group;
    $X_3$ is a covalent bond, —O—, —NHC(O)—, or —C(O)NH—; and
    $R_g$ is $C_{1-6}$ alkyl, Cis alkenyl, $C_{1-8}$ alkynyl, $C_{6-12}$ aryl, $C_{1-12}$ heteroaryl, $C_{7-12}$ aralkyl, or a substituted version of any of these groups; or
wherein when Y is —O—,
  $R_1$ is $C_{1-18}$ alkyl, $C_{1-18}$ alkenyl, $C_{1-18}$ alkynyl, $C_{7-18}$ aralkyl, or a substituted version of any of these groups;
or
  a group of the formula:

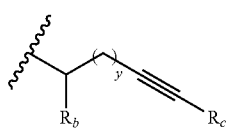

wherein:
  $R_b$ is hydrogen, $C_{1-8}$ alkyl, substituted $C_{1-8}$ alkyl, $C_{6-12}$ aryl, substituted $C_{6-12}$ aryl, or —C(O)$R_d$;
    wherein: $R_d$ is amino, hydroxy, —NHNH$_2$, $C_{1-6}$ alkoxy, $C_{1-6}$ alkylamino, or $C_{1-8}$ dialkylamino, or a substituted version of any of the last three groups; or
  $R_c$ is hydrogen, $C_{1-8}$ alkyl, $C_{1-8}$ alkenyl, $C_{1-8}$ alkynyl, $C_{6-12}$ aryl, $C_{1-12}$ heteroaryl, or a substituted version of any of the last five groups; and
  y is 0, 1, 2, or 3;
or a pharmaceutically acceptable salt thereof.

In some embodiments, the compound is further defined as:

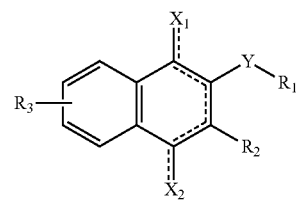

(I)

wherein:
  $X_1$ and $X_2$ are each independently oxo or hydroxy;
  $R_2$ is hydrogen, $C_{1-6}$ alkyl, $C_{6-12}$ aryl, $C_{5-12}$ heteroaryl, $C_{1-6}$ alkanediyl-$C_{6-12}$ aryl, —NH—CO—$C_{6-12}$ aryl, —C$_{1-4}$alkanediyl-O—C$_{6-12}$ aryl, halogen, or a substituted version thereof;
  $R_3$ is hydrogen, amino, cyano, halo, hydroxy, nitro, aminosulfonyl, hydroxysulfonyl, $C_{1-6}$ alkyl, $C_{1-6}$ acyl, $C_{1-6}$ alkoxy, $C_{1-6}$ alkylamino, $C_{1-8}$ dialkylamino, or a substituted version of any of the last five groups;
  Y is —NH— or —O—;
  wherein when Y is —NH— and $R_2$ is hydrogen,
    $R_1$ is $C_{6-18}$ alkenyl; —(CH$_2$)$_x$C≡CR$_a$; wherein: x is 1, 2, 3, or 4 and $R_a$ is $C_{1-8}$ alkyl, $C_{1-8}$ alkenyl, $C_{1-8}$ alkynyl, $C_{6-12}$ aryl, $C_{1-12}$ heteroaryl, or a substituted version of any of these groups;
  a group of the formula:

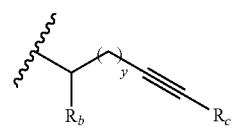

wherein:
  $R_b$ is $C_{1-8}$ alkyl, substituted $C_{1-8}$ alkyl, $C_{6-12}$ aryl, substituted $C_{6-12}$ aryl, or —C(O)$R_d$;
    wherein: $R_d$ is amino, hydroxy, —NHNH$_2$, $C_{1-6}$ alkoxy, $C_{1-6}$ alkylamino, or $C_{1-8}$ dialkylamino, or a substituted version of any of the last three groups; or $R_c$ is hydrogen, $C_{1-8}$ alkyl, $C_{1-8}$ alkenyl, $C_{1-8}$ alkynyl, $C_{6-12}$ aryl, $C_{1-12}$ heteroaryl, or a substituted version of any of the last five groups; and y is 0, 1, or 2; or a group of the formula:

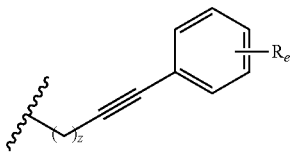

wherein:
z is 1, 2, or 3
$R_e$ is halo, $C_{1-6}$ alkyl, $C_{1-6}$ alkoxy, $C_{1-6}$ alkylsulfonylamino, or a substituted version of any of the last three groups; or
a group of the formula:

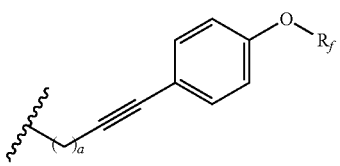

wherein:
a is 1, 2, or 3
$R_f$ is $C_{6-12}$ aryl, $C_{7-12}$ aralkyl, or a substituted version of any of either groups;
wherein when Y is —NH— and $R_2$ is not hydrogen; then:
$R_1$ is $C_{6-12}$ alkenyl, $C_{6-12}$ alkynyl, $C_{6-12}$ aryl, $C_{1-12}$ heteroaryl, or a substituted version of any of these groups, or —Y'—$X_3$—$R_g$, wherein:
Y' is $C_{1-6}$ alkynediyl, $C_{6-12}$ arenediyl, or a substituted version of either group;
$X_3$ is a covalent bond, —O—, —NHC(O)—, or —C(O)NH—; and
$R_g$ is $C_{1-6}$ alkyl $C_{1-8}$ alkenyl, $C_{1-8}$ alkynyl, $C_{6-12}$ aryl, $C_{1-12}$ heteroaryl, $C_{7-12}$ aralkyl, or a substituted version of any of these groups; or
wherein when Y is —O—,
$R_1$ is $C_{1-18}$ alkyl, substituted $C_{1-18}$ alkyl, $C_{1-18}$ alkenyl, substituted $C_{1-18}$ alkenyl, $C_{1-18}$ alkynyl, or substituted $C_{1-18}$ alkynyl; or
a group of the formula:

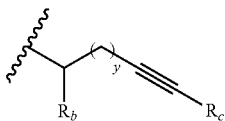

wherein:
$R_b$ is $C_{1-8}$ alkyl, substituted $C_{1-8}$ alkyl, $C_{6-12}$ aryl, substituted $C_{6-12}$ aryl, or —C(O)$R_d$;
wherein: $R_d$ is amino, hydroxy, —NHNH$_2$, $C_{1-6}$ alkoxy, $C_{1-6}$ alkylamino, or $C_{1-8}$ dialkylamino, or a substituted version of any of the last three groups; or $R_c$ is hydrogen, $C_{1-8}$ alkyl, $C_{1-8}$ alkenyl, $C_{1-8}$ alkynyl, $C_{6-12}$ aryl, $C_{1-12}$ heteroaryl, or a substituted version of any of the last five groups; and y is 0, 1, 2, or 3;

or a pharmaceutically acceptable salt thereof.

In some embodiments, Y is —NH—, $R_2$ is hydrogen, and $R_1$ is $C_{1-8}$ alkyl, such isopentyl.

In some embodiments, the disease is a neurological disease such as epilepsy, bipolar disorder or the manic phase of bipolar disorder, headaches, migraines, a traumatic brain injury, Parkinson's disease, Alzheimer's disease, Huntington's disease, Friedereich's Ataxia, or optic atrophy. In some embodiments, the neurological disease is epilepsy such as medication-resistant epilepsy. In other embodiments, the disease is a mitochondrial disease such as mitochondrial DNA depletion syndrome or dysfunctional mitochondrial respiratory chain disorder.

In some embodiments, the pharmaceutical composition is formulated for oral, sublingual, intranasal, intravenous, subcutaneous, parenteral, inhalation, or aerosol delivery; thus, in some embodiments the pharmaceutical composition may be administered orally, sublingually, intranasally, intravenously, subcutaneously, parenterally, or via inhalation or aerosol. In some embodiments, the subject is a human. In some embodiments, the compound has the structure:

(II)

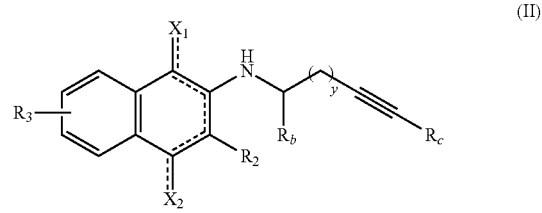

wherein:
$R_2$, $R_3$, $X_1$ and $X_2$ are as defined above; and
$R_b$ is $C_{1-8}$ alkyl, substituted $C_{1-8}$ alkyl, $C_{6-12}$ aryl, substituted $C_{6-12}$ aryl, or —C(O)$R_d$;
wherein: $R_d$ is amino, hydroxy, —NHNH$_2$, $C_{1-6}$ alkoxy, $C_{1-6}$ alkylamino, or $C_{1-8}$ dialkylamino, or a substituted version of any of the last three groups; or
$R_c$ is hydrogen, $C_{1-8}$ alkyl, $C_{1-8}$ alkenyl, $C_{1-8}$ alkynyl, $C_{6-12}$ aryl, $C_{1-12}$ heteroaryl, or a substituted version of any of the last five groups; and
y is 0, 1, or 2;

or a pharmaceutically acceptable salt thereof.

In some embodiments, $X_1$ and $X_2$ are =O. In some embodiments, $R_3$ is hydrogen. In some embodiments, $R_4$ is hydrogen. In some embodiments, $R_1$ is —(CH$_2$)$_x$C≡C$R_a$; wherein: x is 1, 2, 3, or 4 and $R_a$ is $C_{1-8}$ alkyl, $C_{1-8}$ alkenyl, $C_{1-8}$ alkynyl, $C_{6-12}$ aryl, $C_{1-12}$ heteroaryl, or a substituted version of any of these groups. In some embodiments, $R_1$ is —(CH$_2$)$_{y1}$—C≡C—$C_{1-8}$ alkyl, wherein y1=1–2. In some embodiments, $R_1$ is —(CH$_2$)$_{y1}$—C≡C—$C_{1-3}$ alkyl, wherein y1=1–2 such as —(CH$_2$)$_{y1}$—C≡C—(CH$_2$)$_{y2}$—CH$_3$, wherein y2=1–6. In some embodiments, $R_1$ is

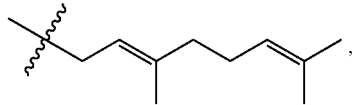

-continued
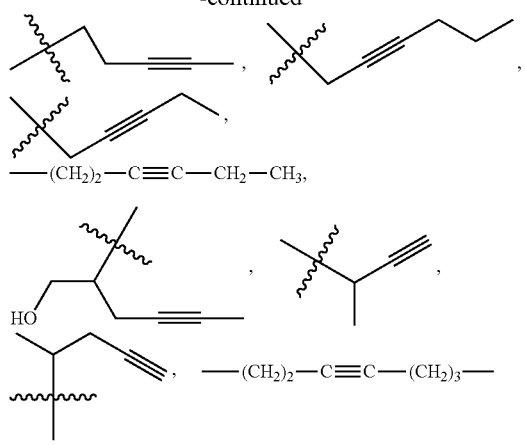
CH$_3$, —(CH$_2$)$_2$—C≡C—(CH$_2$)$_2$—CH$_3$, —CH$_2$—C≡C—(CH$_2$)$_2$—CH$_3$, —CH$_2$—C≡C—(CH$_2$)$_3$—CH$_3$, —CH$_2$—C≡C—(CH$_2$)$_6$—CH$_3$, or —CH$_2$—C≡C—CH$_2$—CH=CH—CH$_3$. In some embodiments, R$_f$ is substituted C$_{6-12}$ aryl or C$_{1-12}$ heteroaryl. In some embodiments, R$_f$ is substituted with a —F, —OCH$_3$, —CF$_3$, or —NHS(O)$_2$CH$_3$ group.
In some embodiments, the compound is further defined as:
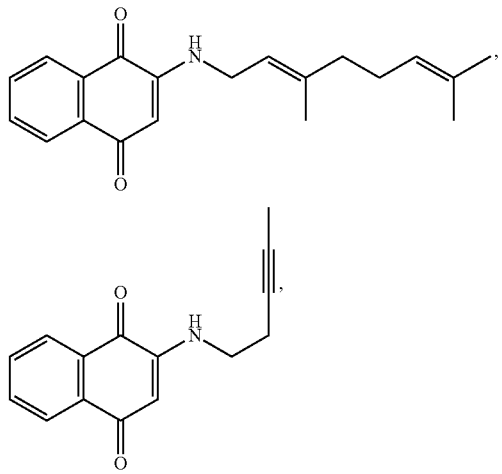
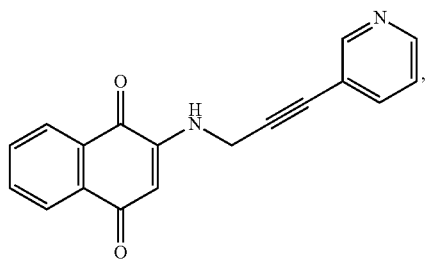
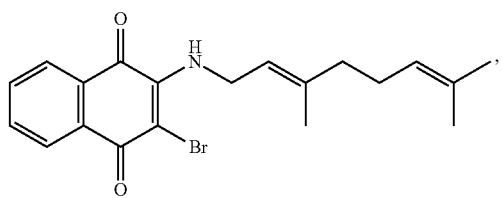
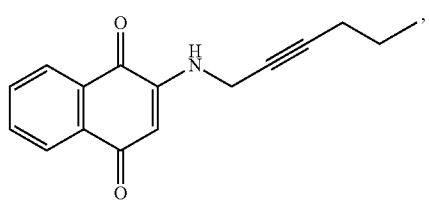

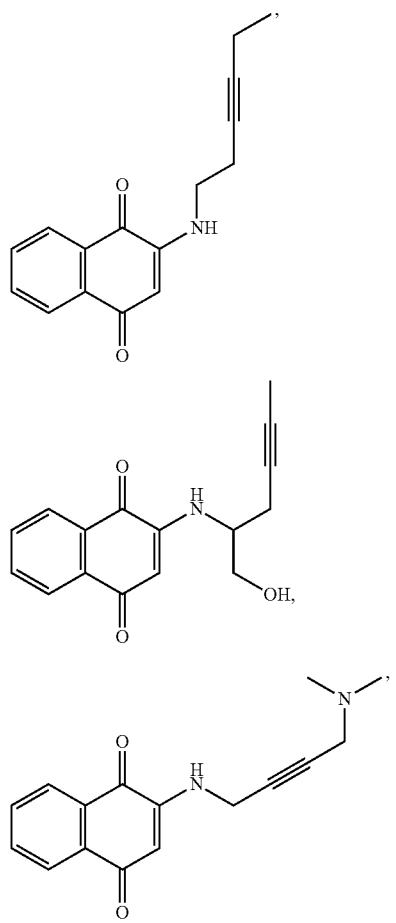
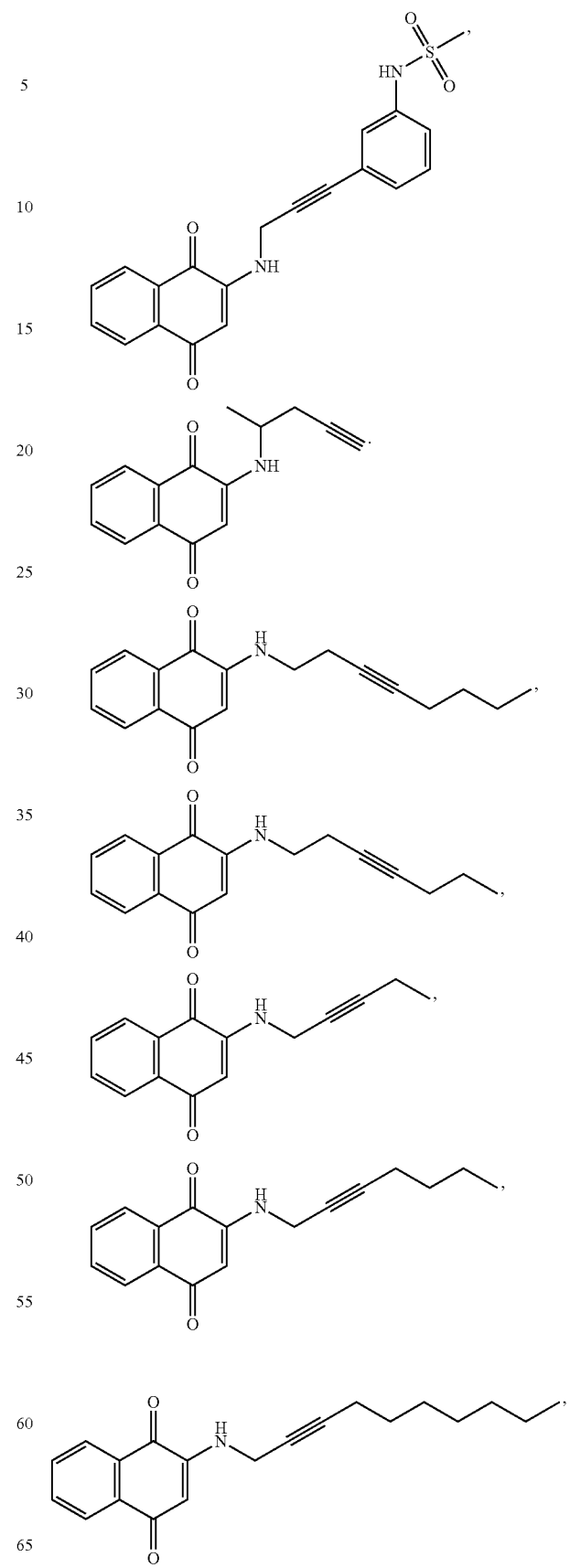

-continued
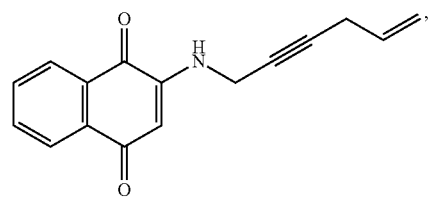
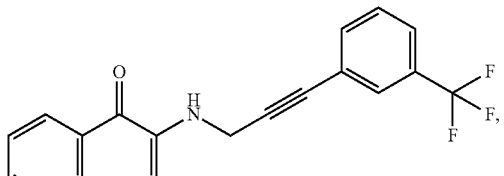
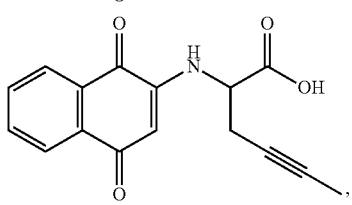
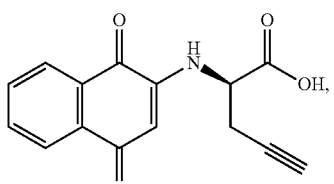
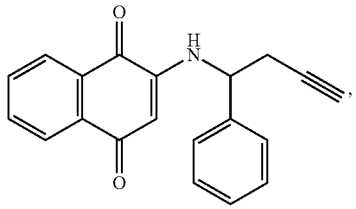
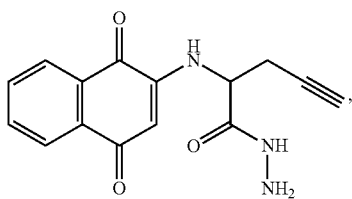
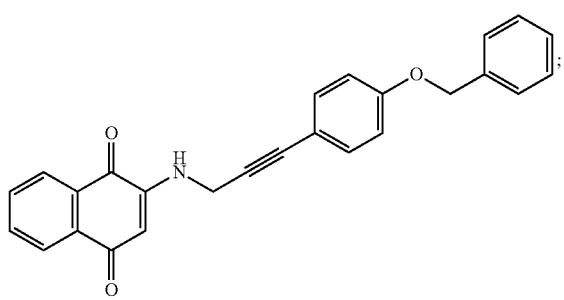 [SMILES: O=C1C=C(NCC#Cc2ccc(OCc3ccccc3)cc2)C(=O)c2ccccc21]
or a pharmaceutically acceptable salt thereof.
In some embodiments, the compound is:
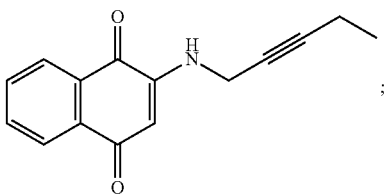 [SMILES: CCC#CCNC1=CC(=O)c2ccccc2C1=O]
or a pharmaceutically acceptable salt thereof.
In other embodiments, the compound is:
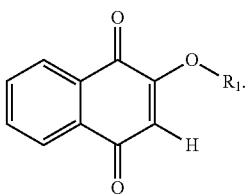
In some embodiments, $R_1$ is
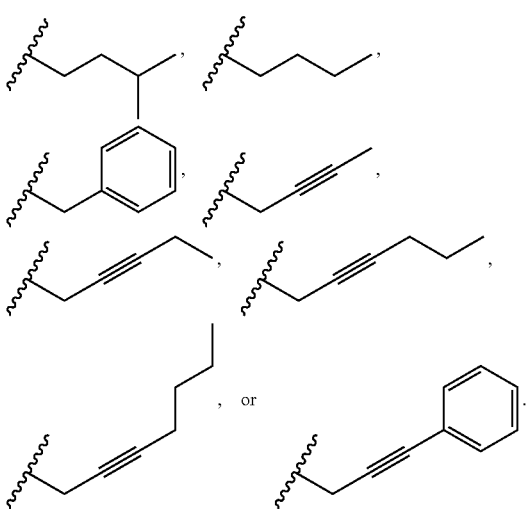
In some embodiments, $R_1$ is
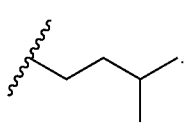 [SMILES: *CCC(C)C]
In some embodiments, the compound is:
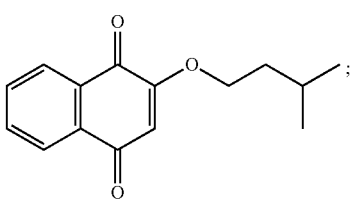 [SMILES: CC(C)CCOC1=CC(=O)c2ccccc2C1=O]

or a pharmaceutically acceptable salt thereof. In some embodiments, the compound is formulated with a pharmaceutically acceptable excipient.

In another aspect, the present disclosure provides pharmaceutical compositions comprising:

(A) a compound of the formula:

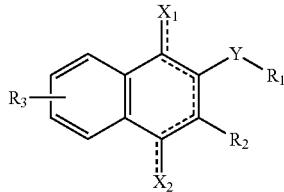

(I)

wherein:
$X_1$ and $X_2$ are each independently oxo or hydroxy;
$R_2$ is hydrogen, $C_{1-6}$ alkyl, $C_{6-12}$ aryl, $C_{5-12}$ heteroaryl, $C_{1-6}$ alkanediyl-$C_{6-12}$ aryl, —NH—CO—$C_{6-12}$ aryl, —$C_{1-4}$alkanediyl-O—$C_{6-12}$ aryl, halogen, or a substituted version thereof;
$R_3$ is hydrogen, amino, cyano, halo, hydroxy, nitro, aminosulfonyl, hydroxysulfonyl, $C_{1-6}$ alkyl, $C_{1-6}$ acyl, $C_{1-6}$ alkoxy, $C_{1-6}$ alkylamino, $C_{1-8}$ dialkylamino, or a substituted version of any of the last five groups;
Y is —NH— or —O—;
wherein when Y is —NH— and $R_2$ is hydrogen,
$R_1$ is $C_{1-8}$ alkyl, $C_{6-18}$ alkenyl, or $C_{6-12}$ aryl; —(CH$_2$)$_x$C≡CR$_a$; wherein: x is 1, 2, 3, or 4 and $R_a$ is $C_{1-8}$ alkyl, $C_{1-8}$ alkenyl, $C_{1-8}$ alkynyl, $C_{6-12}$ aryl, $C_{1-12}$ heteroaryl, or a substituted version of any of these groups;
a group of the formula:

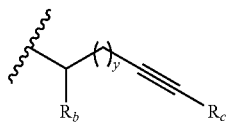

wherein:
$R_b$ is $C_{1-8}$ alkyl, substituted $C_{1-8}$ alkyl, $C_{6-12}$ aryl, substituted $C_{6-12}$ aryl, or —C(O)R$_d$;
wherein: $R_d$ is amino, hydroxy, —NHNH$_2$, $C_{1-6}$ alkoxy, $C_{1-6}$ alkylamino, or $C_{1-8}$ dialkylamino, or a substituted version of any of the last three groups; or
$R_c$ is hydrogen, $C_{1-8}$ alkyl, $C_{1-8}$ alkenyl, $C_{1-8}$ alkynyl, $C_{6-12}$ aryl, $C_{1-12}$ heteroaryl, or a substituted version of any of the last five groups; and
y is 0, 1, or 2; or
a group of the formula:

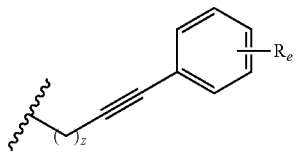

wherein:
z is 1, 2, or 3
$R_e$ is halo, $C_{1-6}$ alkyl, $C_{1-6}$ alkoxy, $C_{1-6}$ alkylsulfonylamino, or a substituted version of any of the last three groups; or
a group of the formula:

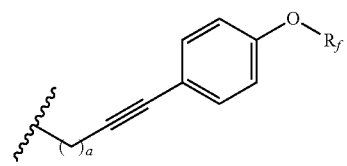

wherein:
a is 1, 2, or 3
$R_f$ is $C_{6-12}$ aryl, $C_{7-12}$ aralkyl, or a substituted version of any of either groups;
wherein when Y is —NH— and $R_2$ is not hydrogen; then:
$R_1$ is $C_{1-12}$ alkyl, $C_{6-12}$ alkenyl, $C_{6-12}$ alkynyl, $C_{6-12}$ aryl, $C_{1-12}$ heteroaryl, or a substituted version of any of these groups, or —Y'—X$_3$—R$_g$, wherein:
Y' is $C_{1-6}$ alkynediyl, $C_{6-12}$ arenediyl, or a substituted version of either group;
$X_3$ is a covalent bond, —O—, —NHC(O)—, or —C(O)NH—; and
$R_g$ is $C_{1-6}$ alkyl, $C_{1-8}$ alkenyl, $C_{1-8}$ alkynyl, $C_{6-12}$ aryl, $C_{1-12}$ heteroaryl, $C_{7-12}$ aralkyl, or a substituted version of any of these groups; or
wherein when Y is —O—,
$R_1$ is $C_{1-18}$ alkyl, $C_{1-18}$ alkenyl, $C_{1-18}$ alkynyl, $C_{7-18}$ aralkyl, or a substituted version of any of these groups;
or
a group of the formula:

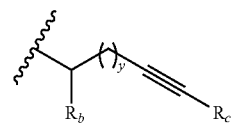

wherein:
$R_b$ is hydrogen, $C_{1-8}$ alkyl, substituted $C_{1-8}$ alkyl, $C_{6-12}$ aryl, substituted $C_{6-12}$ aryl, or —C(O)R$_d$;
wherein: $R_d$ is amino, hydroxy, —NHNH$_2$, $C_{1-6}$ alkoxy, $C_{1-6}$ alkylamino, or $C_{1-8}$ dialkylamino, or a substituted version of any of the last three groups; or
$R_c$ is hydrogen, $C_{1-8}$ alkyl, $C_{1-8}$ alkenyl, $C_{1-8}$ alkynyl, $C_{6-12}$ aryl, $C_{1-12}$ heteroaryl, or a substituted version of any of the last five groups; and
y is 0, 1, 2, or 3;
or a pharmaceutically acceptable salt thereof; and
(B) an excipient.

In some embodiments, the compound is further defined as:

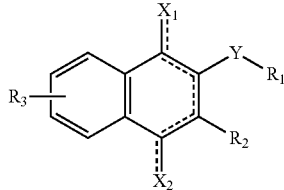

(I)

wherein:
X₁ and X₂ are each independently oxo or hydroxy;
R₂ is hydrogen, $C_{1-6}$ alkyl, $C_{6-12}$ aryl, $C_{5-12}$ heteroaryl, $C_{1-6}$ alkanediyl-$C_{6-12}$ aryl, —NH—CO—$C_{6-12}$ aryl, —$C_{1-4}$alkanediyl-O—$C_{6-12}$ aryl, halogen, or a substituted version thereof;
R₃ is hydrogen, amino, cyano, halo, hydroxy, nitro, aminosulfonyl, hydroxysulfonyl, $C_{1-6}$ alkyl, $C_{1-6}$ acyl, $C_{1-6}$ alkoxy, $C_{1-6}$ alkylamino, $C_{1-8}$ dialkylamino, or a substituted version of the last five groups;
Y is —NH— or —O—;
wherein when Y is —NH— and R₂ is hydrogen,
R₁ is $C_{6-18}$ alkenyl; —(CH₂)ₓC≡Rₐ; wherein: x is 1, 2, 3, or 4 and Rₐ is $C_{1-8}$ alkyl, $C_{1-8}$ alkenyl, $C_{1-8}$ alkynyl, $C_{6-12}$ aryl, $C_{1-12}$ heteroaryl, or a substituted version of any of these groups;
a group of the formula:

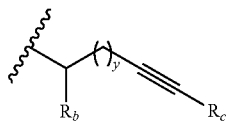

wherein:
$R_b$ is $C_{1-8}$ alkyl, substituted $C_{1-8}$ alkyl, $C_{6-12}$ aryl, substituted $C_{6-12}$ aryl, or —C(O)$R_d$;
wherein: $R_d$ is amino, hydroxy, —NHNH₂, $C_{1-6}$ alkoxy, $C_{1-6}$ alkylamino, or $C_{1-8}$ dialkylamino, or a substituted version of any of the last three groups; or
$R_c$ is hydrogen, $C_{1-8}$ alkyl, $C_{1-8}$ alkenyl, $C_{1-8}$ alkynyl, $C_{6-12}$ aryl, $C_{1-12}$ heteroaryl, or a substituted version of any of the last five groups; and
y is 0, 1, or 2; or
a group of the formula:

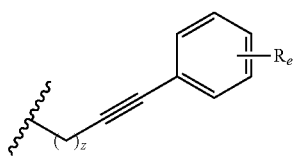

wherein:
z is 1, 2, or 3
$R_e$ is halo, $C_{1-6}$ alkyl, $C_{1-6}$ alkoxy, $C_{1-6}$ alkylsulfonylamino, or a substituted version of any of the last three groups; or a group of the formula:

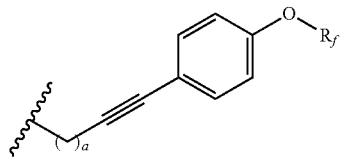

wherein:
a is 1, 2, or 3
$R_f$ is $C_{6-12}$ aryl, $C_{7-12}$ aralkyl, or a substituted version of any of either groups;
wherein when Y is —NH— and R₂ is not hydrogen; then:
R₁ is $C_{6-12}$ alkenyl, $C_{6-12}$ alkynyl, $C_{6-12}$ aryl, $C_{1-12}$ heteroaryl, or a substituted version of any of these groups, or —Y'—X₃—$R_g$, wherein:
Y' is $C_{1-6}$ alkynediyl, $C_{6-12}$ arenediyl, or a substituted version of either group;
X₃ is a covalent bond, —O—, —NHC(O)—, or —C(O)NH—; and
$R_g$ is $C_{1-6}$ alkyl $C_{1-8}$ alkenyl, $C_{1-8}$ alkynyl, $C_{6-12}$ aryl, $C_{1-12}$ heteroaryl, $C_{7-12}$ aralkyl, or a substituted version of either group; or
wherein when Y is —O—,
R₁ is $C_{1-18}$ alkynyl or substituted $C_{1-18}$ alkynyl;
a group of the formula:

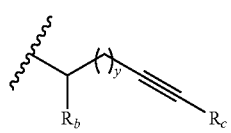

wherein:
$R_b$ is hydrogen, $C_{1-8}$ alkyl, substituted $C_{1-8}$ alkyl, $C_{6-12}$ aryl, substituted $C_{6-12}$ aryl, or —C(O)$R_d$;
wherein: $R_d$ is amino, hydroxy, —NHNH₂, $C_{1-6}$ alkoxy, $C_{1-6}$ alkylamino, or $C_{1-8}$ dialkylamino, or a substituted version of any of the last three groups; or
$R_c$ is hydrogen, $C_{1-8}$ alkyl, $C_{1-8}$ alkenyl, $C_{1-8}$ alkynyl, $C_{6-12}$ aryl, $C_{1-12}$ heteroaryl, or a substituted version of any of the last five groups; and
y is 0, 1, 2, or 3; or
or a pharmaceutically acceptable salt thereof.

In some embodiments, the pharmaceutical composition is administered orally, sublingually, intranasally, intravenously, subcutaneously, parenterally, via inhalation, or aerosol. In some embodiments, the compound is the compound described herein. In some embodiments, the pharmaceutical composition is formulated as a unit dose.

In some aspects the present disclosure provides pharmaceutical compositions comprising:
(A) a compound of the formula:

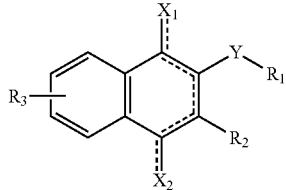

(I)

wherein:
X$_1$ and X$_2$ are each independently oxo or hydroxy;
R$_2$ is hydrogen, C$_{1-6}$ alkyl, C$_{6-12}$ aryl, C$_{5-12}$ heteroaryl, C$_{1-6}$ alkanediyl-C$_{6-12}$ aryl, —NH—CO—C$_{6-12}$ aryl, —C$_{1-4}$alkanethyl-O—C$_{6-12}$ aryl, halogen, or a substituted version thereof;
R$_3$ is hydrogen, amino, cyano, halo, hydroxy, nitro, aminosulfonyl, hydroxysulfonyl, C$_{1-6}$ alkyl, C$_{1-6}$ acyl, C$_{1-6}$ alkoxy, C$_{1-6}$ alkylamino, C$_{1-8}$ dialkylamino, or a substituted version of any of the last five groups;
Y is —NH— or —O—;
wherein when Y is —NH— and R$_2$ is hydrogen,
R$_1$ is C$_{1-8}$ alkyl, C$_{6-18}$ alkenyl, or C$_{6-12}$ aryl; —(CH$_2$)$_x$C≡CR$_a$; wherein: x is 1, 2, 3, or 4 and R$_a$ is C$_{1-8}$ alkyl, C$_{1-8}$ alkenyl, C$_{1-8}$ alkynyl, C$_{6-12}$ aryl, C$_{1-12}$ heteroaryl, or a substituted version of any of these groups;
a group of the formula:

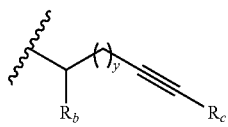

wherein:
R$_b$ is C$_{1-8}$ alkyl, substituted C$_{1-8}$ alkyl, C$_{6-12}$ aryl, substituted C$_{6-12}$ aryl, or —C(O)R$_d$;
wherein: R$_d$ is amino, hydroxy, —NHNH$_2$, C$_{1-6}$ alkoxy, C$_{1-6}$ alkylamino, or C$_{1-8}$ dialkylamino, or a substituted version of any of the last three groups; or
R$_c$ is hydrogen, C$_{1-8}$ alkyl, C$_{1-8}$ alkenyl, alkynyl, C$_{6-12}$ aryl, C$_{1-12}$ heteroaryl, or a substituted version of any of the last five groups; and
y is 0, 1, or 2; or
a group of the formula:

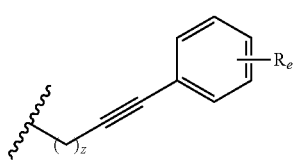

wherein:
z is 1, 2, or 3
R$_e$ is halo, C$_{1-6}$ alkyl, C$_{1-6}$ alkoxy, C$_{1-6}$ alkylsulfonylamino, or a substituted version of any of the last three groups; or a group of the formula:

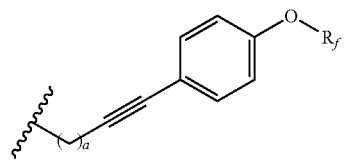

wherein:
a is 1, 2, or 3
R$_f$ is C$_{6-12}$ aryl, C$_{7-12}$ aralkyl, or a substituted version of any of either groups;
wherein when Y is —NH— and R$_2$ is not hydrogen; then:
R$_1$ is C$_{1-12}$ alkyl, C$_{6-12}$ alkenyl, C$_{6-12}$ alkynyl, C$_{6-12}$ aryl, C$_{1-12}$ heteroaryl, or a substituted version of any of these groups, or —Y'—X$_3$—R$_g$, wherein:
Y' is C$_{1-6}$ alkynediyl, C$_{6-12}$ arenediyl, or a substituted version of either group;
X$_3$ is a covalent bond, —O—, —NHC(O)—, or —C(O)NH—; and
R$_g$ is C$_{1-6}$ alkyl, C$_{1-8}$ alkenyl, C$_{1-8}$ alkynyl, C$_{6-12}$ aryl, C$_{1-12}$ heteroaryl, C$_{7-12}$ aralkyl, or a substituted version of any of these groups; or
wherein when Y is —O—,
R$_1$ is C$_{1-18}$ alkyl, C$_{1-18}$ alkenyl, C$_{1-18}$ alkynyl, C$_{7-18}$ aralkyl, or a substituted version of any of these groups;
or
a group of the formula:

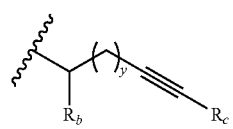

wherein:
R$_b$ is hydrogen, C$_{1-8}$ alkyl, substituted C$_{1-8}$ alkyl, C$_{6-12}$ aryl, substituted C$_{6-12}$ aryl, or —C(O)R$_d$;
wherein: R$_d$ is amino, hydroxy, —NHNH$_2$, C$_{1-6}$ alkoxy, C$_{1-6}$ alkylamino, or C$_{1-8}$ dialkylamino, or a substituted version of any of the last three groups; or
R$_c$ is hydrogen, C$_{1-8}$ alkyl, C$_{1-8}$ alkenyl, C$_{1-8}$ alkynyl, C$_{6-12}$ aryl, C$_{1-12}$ heteroaryl, or a substituted version of any of the last five groups; and
y is 0, 1, 2, or 3;
or a pharmaceutically acceptable salt thereof.
In some embodiments, the compound is further defined as:

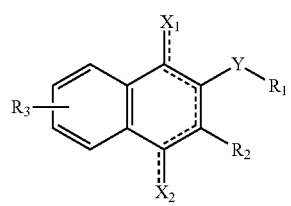

(I)

wherein:

X$_1$ and X$_2$ are each independently oxo or hydroxy;

R$_2$ is hydrogen, C$_{1-6}$ alkyl, C$_{6-12}$ aryl, C$_{5-12}$ heteroaryl, C$_{1-6}$ alkanediyl-C$_{6-12}$ aryl, —NH—CO—C$_{6-12}$ aryl, —C$_{1-4}$alkanediyl-O—C$_{6-12}$ aryl, halogen, or a substituted version thereof;

R$_3$ is hydrogen, amino, cyano, halo, hydroxy, nitro, aminosulfonyl, hydroxysulfonyl, C$_{1-6}$ alkyl, C$_{1-6}$ acyl, C$_{1-6}$ alkoxy, C$_{1-6}$ alkylamino, C$_{1-8}$ dialkylamino, or a substituted version of any of the last five groups;

Y is —NH— or —O—;

wherein when Y is —NH— and R$_2$ is hydrogen,

R$_1$ is C$_{6-18}$ alkenyl; —(CH$_2$)$_x$C≡CR$_a$; wherein: x is 1, 2, 3, or 4 and R$_a$ is C$_{1-8}$ alkyl, C$_{1-8}$ alkenyl, C$_{1-8}$ alkynyl, C$_{6-12}$ aryl, C$_{1-12}$ heteroaryl, or a substituted version of any of these groups;

a group of the formula:

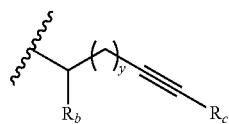

wherein:

R$_b$ is C$_{1-8}$ alkyl, substituted C$_{1-8}$ alkyl, C$_{6-12}$ aryl, substituted C$_{6-12}$ aryl, or —C(O)R$_d$;

wherein: R$_d$ is amino, hydroxy, —NHNH$_2$, C$_{1-6}$ alkoxy, C$_{1-6}$ alkylamino, or C$_{1-8}$ dialkylamino, or a substituted version of any of the last three groups; or R$_c$ is hydrogen, C$_{1-8}$ alkyl, C$_{1-8}$ alkenyl, C$_{1-8}$ alkynyl, C$_{6-12}$ aryl, C$_{1-12}$ heteroaryl, or a substituted version of any of the last five groups; and y is 0, 1, or 2; or a group of the formula:

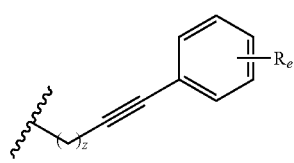

wherein:

z is 1, 2, or 3

R$_e$ is halo, C$_{1-6}$ alkyl, C$_{1-6}$ alkoxy, C$_{1-6}$ alkylsulfonylamino, or a substituted version of any of the last three groups; or a group of the formula:

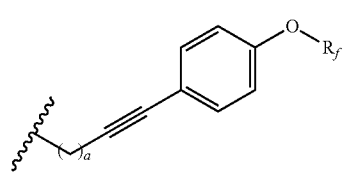

wherein:

a is 1, 2, or 3

R$_f$ is C$_{6-12}$ aryl, C$_{7-12}$ aralkyl, or a substituted version of any of either groups;

wherein when Y is —NH— and R$_2$ is not hydrogen; then:

R$_1$ is C$_{6-12}$ alkenyl, C$_{6-12}$ alkynyl, C$_{6-12}$ aryl, C$_{1-12}$ heteroaryl, or a substituted version of any of these groups, or —Y'—X$_3$—R$_g$, wherein:

Y' is C$_{1-6}$ alkynediyl, C$_{6-12}$ arenediyl, or a substituted version of either group;

X$_3$ is a covalent bond, —O—, —NHC(O)—, or —C(O)NH—; and

R$_g$ is C$_{1-6}$ alkyl, C$_{1-8}$ alkenyl, C$_{1-8}$ alkynyl, C$_{6-12}$ aryl, C$_{1-12}$ heteroaryl, C$_{7-12}$ aralkyl, or a substituted version of any of these groups; or wherein when Y is —O—, R$_1$ is C$_{1-18}$ alkyl, substituted C$_{1-18}$ alkyl, C$_{1-18}$ alkenyl, substituted C$_{1-18}$ alkenyl, C$_{1-18}$ alkynyl, and substituted C$_{1-18}$ alkynyl; or a group of the formula:

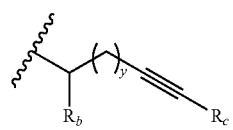

wherein:

R$_b$ is C$_{1-8}$ alkyl, substituted C$_{1-8}$ alkyl, C$_{6-12}$ aryl, substituted C$_{6-12}$ aryl, or —C(O)R$_d$;

wherein: R$_d$ is amino, hydroxy, —NHNH$_2$, C$_{1-6}$ alkoxy, C$_{1-6}$ alkylamino, or C$_{1-8}$ dialkylamino, or a substituted version of any of the last three groups; or R$_c$ is hydrogen, C$_{1-8}$ alkyl, C$_{1-8}$ alkenyl, C$_{1-8}$ alkynyl, C$_{6-12}$ aryl, C$_{1-12}$ heteroaryl, or a substituted version of any of the last five groups; and y is 0, 1, 2, or 3;

or a pharmaceutically acceptable salt thereof.

In some embodiments, Y is —NH—, R$_2$ is hydrogen, and R$_1$ is C$_{1-8}$ alkyl, such as isopentyl.

In some embodiments, the compound has the structure:

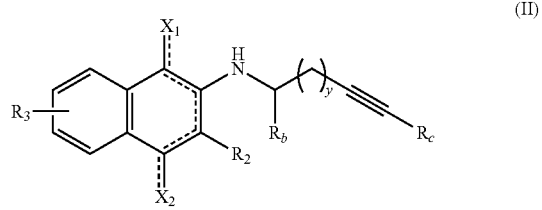

(II)

wherein:

R$_2$, R$_3$, X$_1$ and X$_2$ are as defined above; and

R$_b$ is C$_{1-8}$ alkyl, substituted C$_{1-8}$ alkyl, C$_{6-12}$ aryl, substituted C$_{6-12}$ aryl, or —C(O)R$_d$; wherein: R$_d$ is amino, hydroxy, —NHNH$_2$, C$_{1-6}$ alkoxy, C$_{1-6}$ alkylamino, or C$_{1-8}$ dialkylamino, or a substituted version of any of the last three groups; or $R_c$ is hydrogen, $C_{1-8}$ alkyl, $C_{1-8}$ alkenyl, $C_{1-8}$ alkynyl, $C_{6-12}$ aryl, $C_{1-12}$ heteroaryl, or a substituted version of any of the last five groups; and y is 0, 1, or 2;

or a pharmaceutically acceptable salt thereof.

In some embodiments, $X_1$ and $X_2$ are =O. In some embodiments, $R_3$ is hydrogen. In some embodiments, $R_4$ is hydrogen. In some embodiments, $R_1$ is —(CH$_2$)$_x$C≡CR$_a$; wherein: x is 1, 2, 3, or 4 and $R_a$ is $C_{1-8}$ alkyl, $C_{1-8}$ alkenyl, $C_{1-8}$ alkynyl, $C_{6-12}$ aryl, $C_{1-12}$ heteroaryl, or a substituted version of any of these groups. In some embodiments, $R_1$ is —(CH$_2$)$_{y1}$—C≡C—$C_{1-8}$ alkyl, wherein y1=1–2. In some embodiments, $R_1$ is —(CH$_2$)$_{y1}$—C≡C—$C_{1-3}$ alkyl, wherein y1=1–2. In some embodiments, $R_1$ is —(CH$_2$)$_{y1}$—C≡C—(CH$_2$)$_{y2}$—CH$_3$, wherein y2=1–6. In some embodiments, $R_1$ is

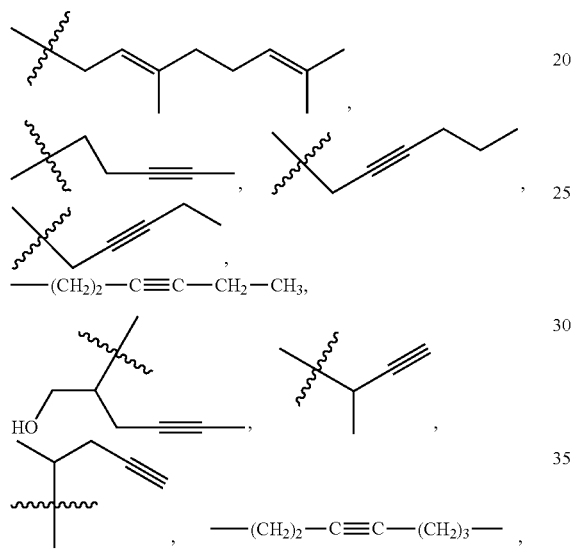

CH$_3$,  —(CH$_2$)$_2$—C≡C—(CH$_2$)$_2$—CH$_3$,  —CH$_2$—C≡C—(CH$_2$)$_2$—CH$_3$,  —CH$_2$—C≡C—(CH$_2$)$_3$—CH$_3$,  —CH$_2$—C≡C—(CH$_2$)$_6$—CH$_3$, or  —CH$_2$—C≡C—CH$_2$—CH=CH—CH$_3$. In some embodiments, $R_f$ is substituted $C_{6-12}$ aryl or $C_{1-12}$ heteroaryl. In some embodiments, $R_f$ is substituted with a —F, —OCH$_3$, —CF$_3$, or —NHS(O)$_2$CH$_3$ group. In some embodiments, the compound is further defined as:

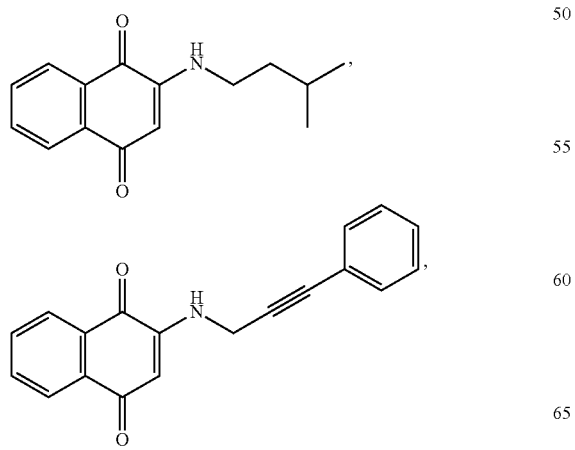

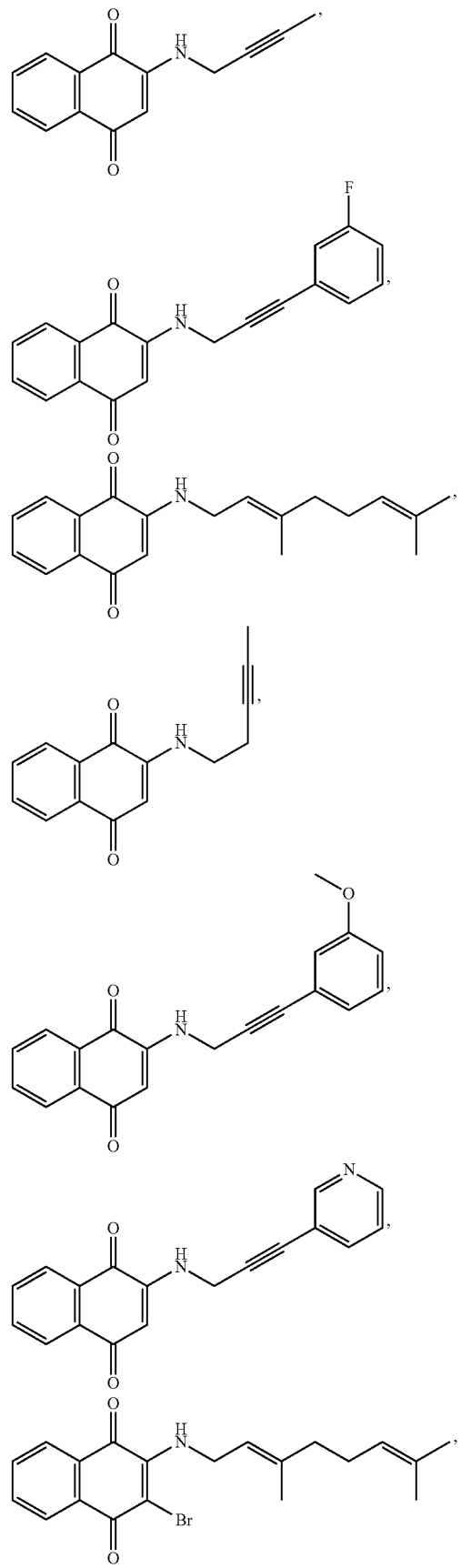

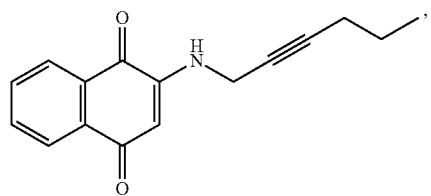
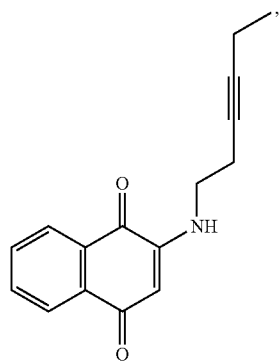
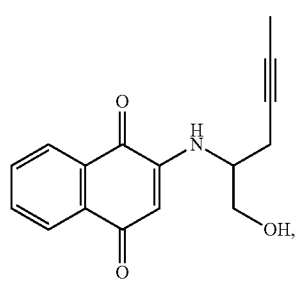
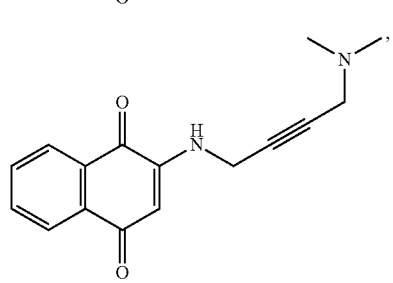
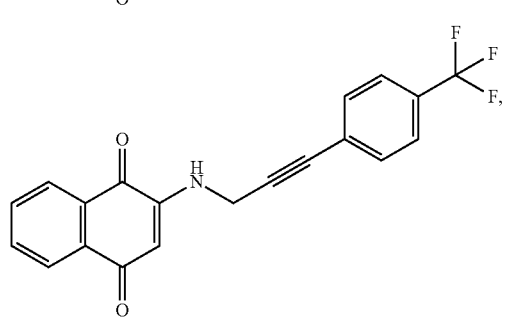
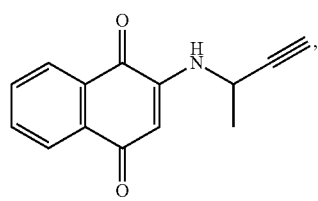
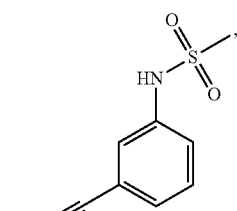
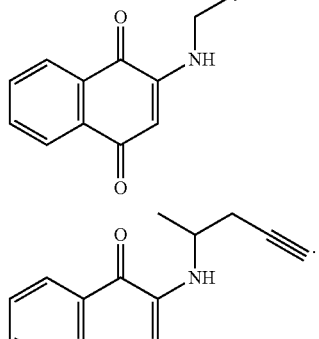
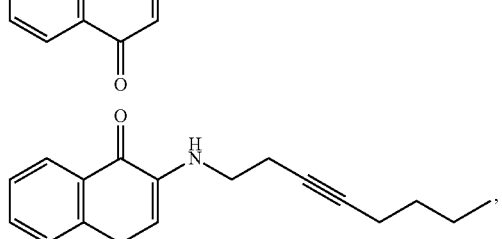
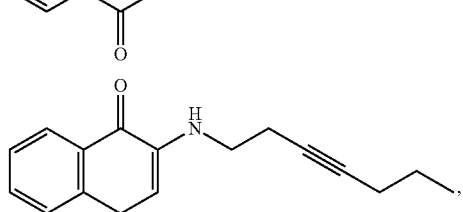
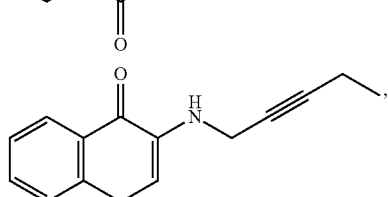
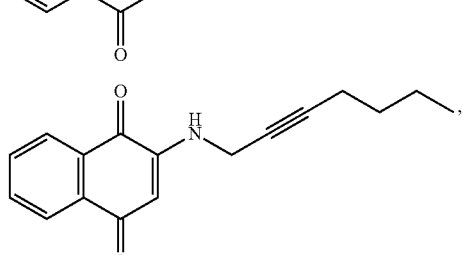
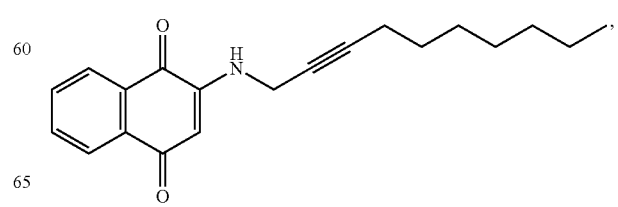

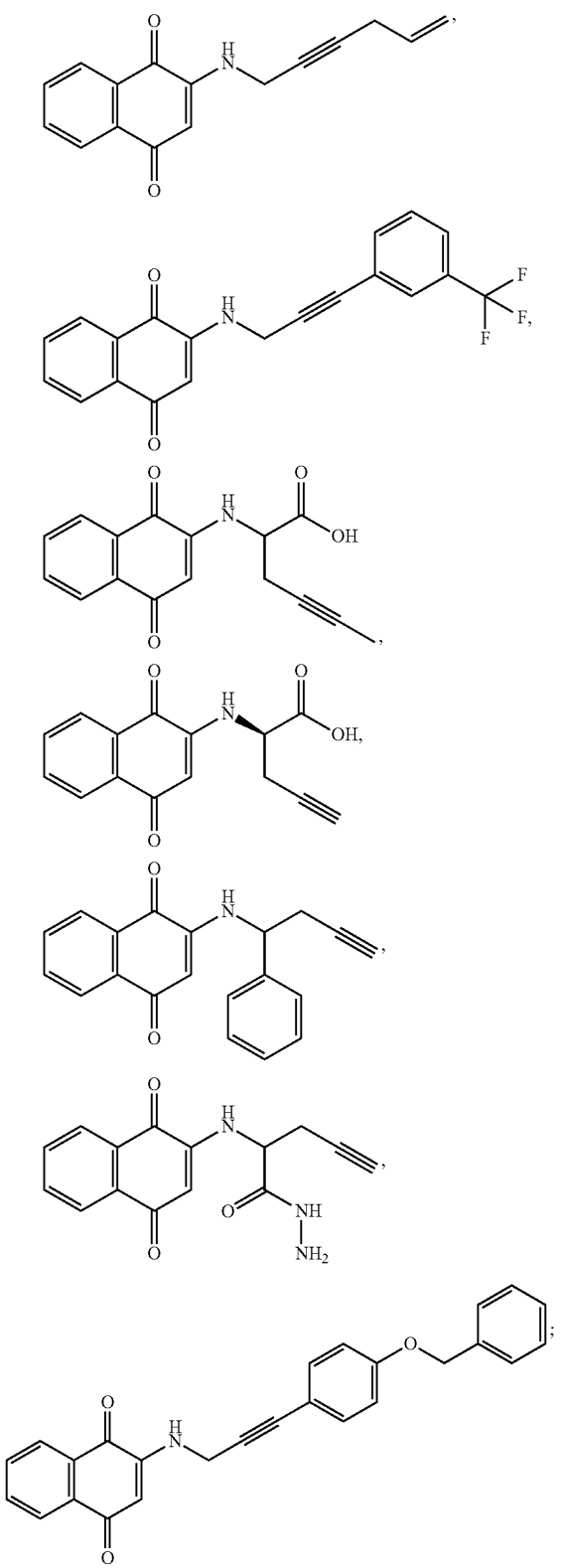
or a pharmaceutically acceptable salt thereof.
In some embodiments, the compound is:
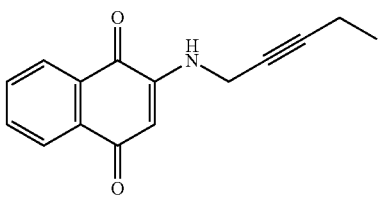
or a pharmaceutically acceptable salt thereof.
In some embodiments, the compound is:
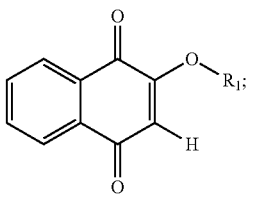
or a pharmaceutically acceptable salt thereof.
In some embodiments, $R_1$ is
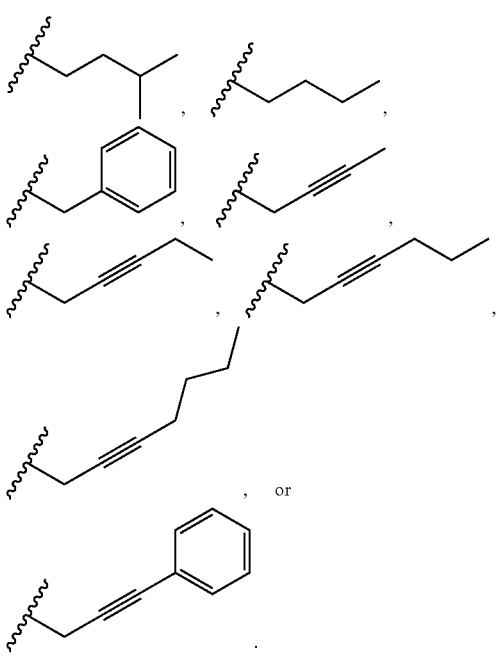
In some embodiments, the compound is:
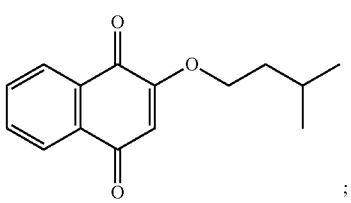 [SMILES: CC(C)CCOC1=CC(=O)c2ccccc2C1=O]
or a pharmaceutically acceptable salt thereof.

In still yet another aspect, the present disclosure provides compounds having the structure:

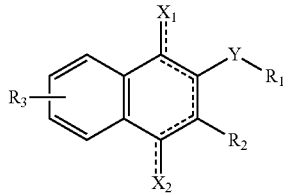
(I)

wherein:
X$_1$ and X$_2$ are each independently oxo or hydroxy;
R$_2$ is hydrogen, C$_{1-6}$ alkyl, C$_{6-12}$ aryl, C$_{5-12}$ heteroaryl, C$_{1-6}$ alkanediyl-C$_{6-12}$ aryl, —NH—CO—C$_{6-12}$ aryl, —C$_{1-4}$alkanediyl-O—C$_{6-12}$ aryl, halogen, or a substituted version thereof;
R$_3$ is hydrogen, amino, cyano, halo, hydroxy, nitro, aminosulfonyl, hydroxysulfonyl, C$_{1-6}$ alkyl, C$_{1-6}$ acyl, C$_{1-6}$ alkoxy, C$_{1-6}$ alkylamino, C$_{1-8}$ dialkylamino, or a substituted version of any of the last five groups;
Y is —NH— or —O—;
wherein when Y is —NH— and R$_2$ is hydrogen,
R$_1$ is isopentyl, C$_{6-18}$ alkenyl, or C$_{6-12}$ aryl; —(CH$_2$)$_x$C≡CR$_a$; wherein: x is 1, 2, 3, or 4 and R$_a$ is C$_{2-8}$ alkyl, C$_{1-8}$ alkenyl, C$_{1-8}$ alkynyl, C$_{1-12}$ heteroaryl, or a substituted version of any of these groups;
a group of the formula:

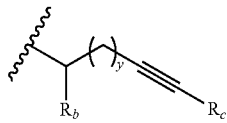

wherein:
R$_b$ is C$_{1-8}$ alkyl, substituted C$_{1-8}$ alkyl, C$_{6-12}$ aryl, substituted C$_{6-12}$ aryl, or —C(O)R$_d$;
wherein: R$_d$ is amino, hydroxy, —NHNH$_2$, C$_{1-6}$ alkoxy, C$_{1-6}$ alkylamino, or C$_{1-8}$ dialkylamino, or a substituted version of any of the last three groups; or
R$_c$ is hydrogen, C$_{1-8}$ alkyl, C$_{1-8}$ alkenyl, C$_{1-8}$ alkynyl, C$_{6-12}$ aryl, C$_{1-12}$ heteroaryl, or a substituted version of any of the last five groups; and
y is 0, 1, or 2; or
a group of the formula:

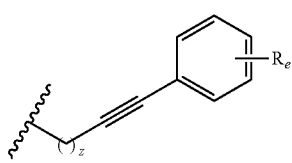

wherein:
z is 1, 2, or 3
R$_e$ is halo, C$_{1-6}$ alkyl, C$_{1-6}$ alkoxy, C$_{1-6}$ alkylsulfonylamino, or a substituted version of any of the last three groups; or a group of the formula:

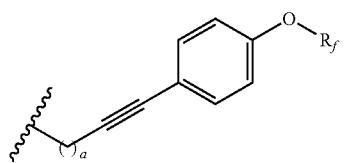

wherein:
a is 1, 2, or 3
R$_f$ is C$_{6-12}$ aryl, C$_{7-12}$ aralkyl, or a substituted version of any of either groups;
wherein when Y is —NH— and R$_2$ is not hydrogen; then:
R$_1$ is C$_{1-12}$ alkyl, C$_{6-12}$ alkenyl, C$_{6-12}$ alkynyl, C$_{6-12}$ aryl, C$_{1-12}$ heteroaryl, or a substituted version of any of these groups, or —Y'—X$_3$—R$_g$, wherein:
Y' is C$_{1-6}$ alkynediyl, C$_{6-12}$ arenediyl, or a substituted version of either group;
X$_3$ is a covalent bond, —O—, —NHC(O)—, or —C(O)NH—; and
R$_g$ is C$_{1-6}$ alkyl, C$_{1-8}$ alkenyl, C$_{1-8}$ alkynyl, C$_{6-12}$ aryl, C$_{1-12}$ heteroaryl, C$_{7-12}$ aralkyl, or a substituted version of any of these groups; or
wherein when Y is —O—,
R$_1$ is C$_{1-18}$ alkyl, C$_{1-18}$ alkenyl, C$_{1-18}$ alkynyl, C$_{7-18}$ aralkyl, or a substituted version of any of these groups;
or
a group of the formula.

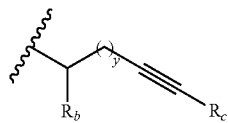

wherein:
R$_b$ is hydrogen, C$_{1-8}$ alkyl, substituted C$_{1-8}$ alkyl, C$_{6-12}$ aryl, substituted C$_{6-12}$ aryl, or —C(O)R$_d$;
wherein: R$_d$ is amino, hydroxy, —NHNH$_2$, C$_{1-6}$ alkoxy, C$_{1-6}$ alkylamino, or C$_{1-8}$ dialkylamino, or a substituted version of any of the last three groups; or
R$_c$ is hydrogen, C$_{1-8}$ alkyl, C$_{1-8}$ alkenyl, C$_{1-8}$ alkynyl, C$_{6-12}$ aryl, C$_{1-12}$ heteroaryl, or a substituted version of any of the last five groups; and
y is 0, 1, 2, or 3;
or a pharmaceutically acceptable salt thereof.
In some embodiments, the compound is further defined as:

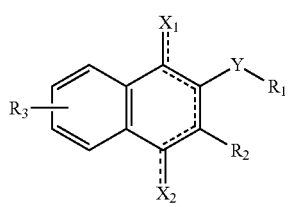
(I)

wherein:
X$_1$ and X$_2$ are each independently oxo or hydroxy;
R$_2$ is hydrogen, C$_{1-6}$ alkyl, C$_{6-12}$ aryl, C$_{5-12}$ heteroaryl, C$_{1-6}$ alkanediyl-C$_{6-12}$ aryl, —NH—CO—C$_{6-12}$ aryl, —C$_{1-4}$alkanediyl-O—C$_{6-12}$ aryl, halogen, or a substituted version thereof;
R$_3$ is hydrogen, amino, cyano, halo, hydroxy, nitro, aminosulfonyl, hydroxysulfonyl, C$_{1-6}$ alkyl, C$_{1-6}$ acyl, C$_{1-6}$ alkoxy, C$_{1-6}$ alkylamino, C$_{1-8}$ dialkylamino, or a substituted version of the last five groups;
Y is —NH— or —O—;
wherein when Y is —NH— and R$_2$ is hydrogen,
R$_1$ is C$_{6-18}$ alkenyl, substituted C$_{6-18}$ alkenyl, or —(CH$_2$)$_x$C≡CR$_a$, wherein: x is 1, 2, 3, or 4 and R$_a$ is C$_{1-8}$ alkenyl, C$_{1-8}$ alkynyl, C$_{1-12}$ heteroaryl, or a substituted version of any of these groups;
a group of the formula:

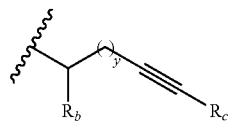

wherein:
R$_b$ is C$_{1-8}$ alkyl, substituted C$_{1-8}$ alkyl, C$_{6-12}$ aryl, substituted C$_{6-12}$ aryl, or —C(O)R$_d$;
wherein: R$_d$ is amino, hydroxy, —NHNH$_2$, C$_{1-6}$ alkoxy, C$_{1-6}$ alkylamino, or C$_{1-8}$ dialkylamino, or a substituted version of any of the last three groups; or
R$_c$ is hydrogen, C$_{1-8}$ alkyl, C$_{1-8}$ alkenyl, C$_{1-8}$ alkynyl, C$_{6-12}$ aryl, C$_{1-12}$ heteroaryl, or a substituted version of any of the last five groups; and
y is 0, 1, or 2; or
a group of the formula:

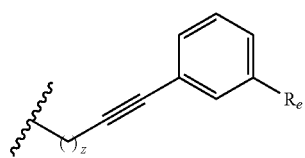

wherein:
z is 1, 2, or 3
R$_e$ is halo, C$_{1-6}$ alkyl, C$_{1-6}$ alkoxy, C$_{1-6}$ alkylsulfonylamino, or a substituted version of any of the last three groups; or
a group of the formula:

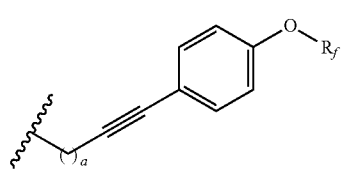

wherein:
a is 1, 2, or 3
R$_f$ is C$_{6-12}$ aryl, C$_{7-12}$ aralkyl, or a substituted version of any of either groups;
wherein when Y is —NH— and R$_2$ is not hydrogen; then:
R$_1$ is C$_{6-12}$ alkenyl, C$_{7-12}$ alkynyl, C$_{6-12}$ aryl, C$_{1-12}$ heteroaryl, or a substituted version of any of these groups, or —Y'—X$_3$—R$_g$, wherein:
Y' is C$_{1-6}$ alkynediyl, C$_{6-12}$ arenediyl, or a substituted version of either group;
X$_3$ is a covalent bond, —O—, —NHC(O)—, or —C(O)NH—; and
R$_g$ is C$_{1-6}$ alkyl C$_{1-8}$ alkenyl, C$_{1-8}$ alkynyl, C$_{6-12}$ aryl, C$_{1-12}$ heteroaryl, C$_{7-12}$ aralkyl, or a substituted version of either group; or
wherein when Y is —O—,
R$_1$ is C$_{1-18}$ alkynyl or substituted C$_{1-18}$ alkynyl; or
a group of the formula:

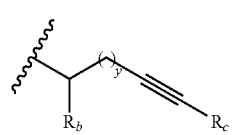

wherein:
R$_b$ is C$_{1-8}$ alkyl, substituted C$_{1-8}$ alkyl, C$_{6-12}$ aryl, substituted C$_{6-12}$ aryl, or —C(O)R$_d$;
wherein: R$_d$ is amino, hydroxy, —NHNH$_2$, C$_{1-6}$ alkoxy, C$_{1-6}$ alkylamino, or C$_{1-8}$ dialkylamino, or a substituted version of any of the last three groups; or
R$_c$ is hydrogen, C$_{1-8}$ alkyl, C$_{1-8}$ alkenyl, C$_{1-8}$ alkynyl, C$_{6-12}$ aryl, C$_{1-12}$ heteroaryl, or a substituted version of any of the last five groups; and
y is 0, 1, 2, or 3; or
or a pharmaceutically acceptable salt thereof.
In some embodiments, the compounds are further defined as:

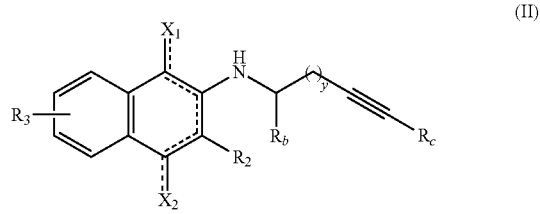

(II)

wherein:
R$_2$, R$_3$, X$_1$ and X$_2$ are as defined above; and
R$_b$ is C$_{1-8}$ alkyl, substituted C$_{1-8}$ alkyl, C$_{6-12}$ aryl, substituted C$_{6-12}$ aryl, or —C(O)R$_d$;
wherein: R$_d$ is amino, hydroxy, —NHNH$_2$, C$_{1-6}$ alkoxy, C$_{1-6}$ alkylamino, or C$_{1-8}$ dialkylamino, or a substituted version of any of the last three groups; or
R$_c$ is hydrogen, C$_{1-8}$ alkyl, C$_{1-8}$ alkenyl, C$_{1-8}$ alkynyl, C$_{6-12}$ aryl, C$_{1-12}$ heteroaryl, or a substituted version of any of the last five groups; and
y is 0, 1, or 2;
or a pharmaceutically acceptable salt thereof.

In other embodiments, the compounds are further defined as:

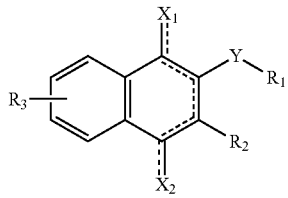
(I)

wherein:

X₁ and X₂ are each independently oxo or hydroxy;

R₂ is $C_{1-6}$ alkyl, $C_{6-12}$ aryl, $C_{5-12}$ heteroaryl, $C_{1-6}$ alkanediyl-$C_{6-12}$ aryl, —NH—CO—$C_{6-12}$ aryl, —$C_{1-4}$alkanediyl-O—$C_{6-12}$ aryl, halogen, or a substituted version thereof;

R₃ is hydrogen, amino, cyano, halo, hydroxy, nitro, aminosulfonyl, hydroxysulfonyl, $C_{1-6}$ alkyl, $C_{1-6}$ acyl, $C_{1-6}$ alkoxy, $C_{1-6}$ alkylamino, $C_{1-8}$ dialkylamino, or a substituted version of the last five groups;

Y is —NH—;

R₁ is $C_{6-12}$ alkenyl, $C_{6-12}$ alkynyl, $C_{6-12}$ aryl, $C_{1-12}$ heteroaryl, or a substituted version of any of these groups, or —Y'—X₃—R_g, wherein:

Y' is $C_{1-6}$ alkynediyl, $C_{6-12}$ arenediyl, or a substituted version of either group;

X₃ is a covalent bond, —O—, —NHC(O)—, or —C(O)NH—; and

R_g is $C_{1-6}$ alkyl $C_{1-8}$ alkenyl, $C_{1-8}$ alkynyl, $C_{6-12}$ aryl, $C_{1-12}$ heteroaryl, $C_{7-12}$ aralkyl, or a substituted version of either group; or or a pharmaceutically acceptable salt thereof.

In other embodiments, the compounds are further defined as:

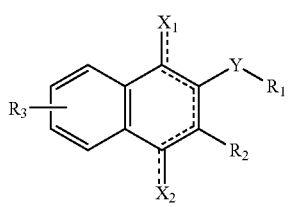
(I)

wherein:

X₁ and X₂ are each independently oxo or hydroxy;

R₂ is hydrogen, $C_{1-6}$ alkyl, $C_{6-12}$ aryl, $C_{5-12}$ heteroaryl, $C_{1-6}$ alkanediyl-$C_{6-12}$ aryl, —NH—CO—$C_{6-12}$ aryl, —$C_{1-4}$alkanediyl-O—$C_{6-12}$ aryl, halogen, or a substituted version thereof;

R₃ is hydrogen, amino, cyano, halo, hydroxy, nitro, aminosulfonyl, hydroxysulfonyl, $C_{1-6}$ alkyl, $C_{1-6}$ acyl, $C_{1-6}$ alkoxy, $C_{1-6}$ alkylamino, $C_{1-8}$ dialkylamino, or a substituted version of the last five groups;

Y is —O—;

R₁ is $C_{1-18}$ alkynyl and substituted $C_{1-18}$ alkynyl; or a group of the formula:

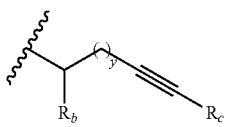

wherein:

R_b is $C_{1-8}$ alkyl, substituted $C_{1-8}$ alkyl, $C_{6-12}$ aryl, substituted $C_{6-12}$ aryl, or —C(O)R_d;

wherein: R_d is amino, hydroxy, —NHNH₂, $C_{1-6}$ alkoxy, alkylamino, or $C_{1-8}$ dialkylamino, or a substituted version of any of the last three groups; or R_c is hydrogen, $C_{1-8}$ alkyl, $C_{1-8}$ alkenyl, $C_{1-8}$ alkynyl, $C_{6-12}$ aryl, $C_{1-12}$ heteroaryl, or a substituted version of any of the last five groups; and y is 0, 1, 2, or 3; or or a pharmaceutically acceptable salt thereof.

In some embodiments, X₁ and X₂ are =O. In some embodiments, R₃ is hydrogen. In some embodiments, R₄ is hydrogen. In some embodiments, R₁ is —(CH₂)_xC≡CR_a; wherein: x is 1, 2, 3, or 4 and R_a is $C_{1-8}$ alkenyl, $C_{1-8}$ alkynyl, $C_{1-12}$ heteroaryl, or a substituted version of any of these groups. In some embodiments, R_f is substituted $C_{6-12}$ aryl or $C_{1-12}$ heteroaryl such as where R_f is substituted with a —F, —CF₃, or —NHS(O)₂CH₃ group. In some embodiments, the compound is further defined as:

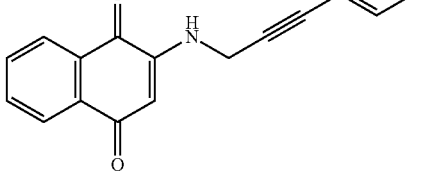

33
-continued
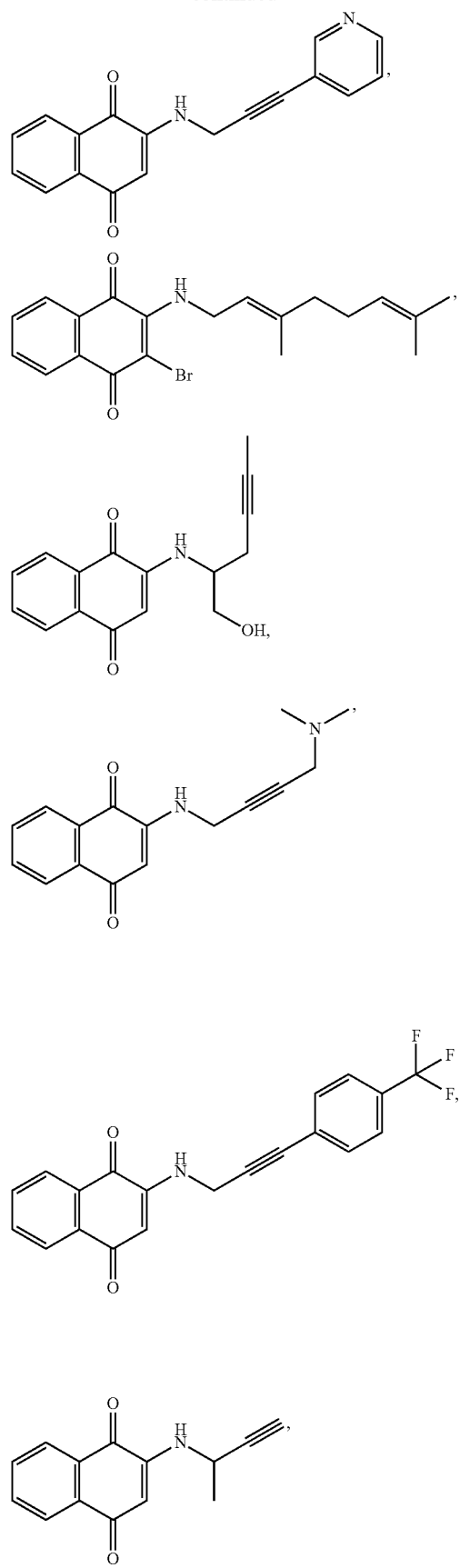
34
-continued
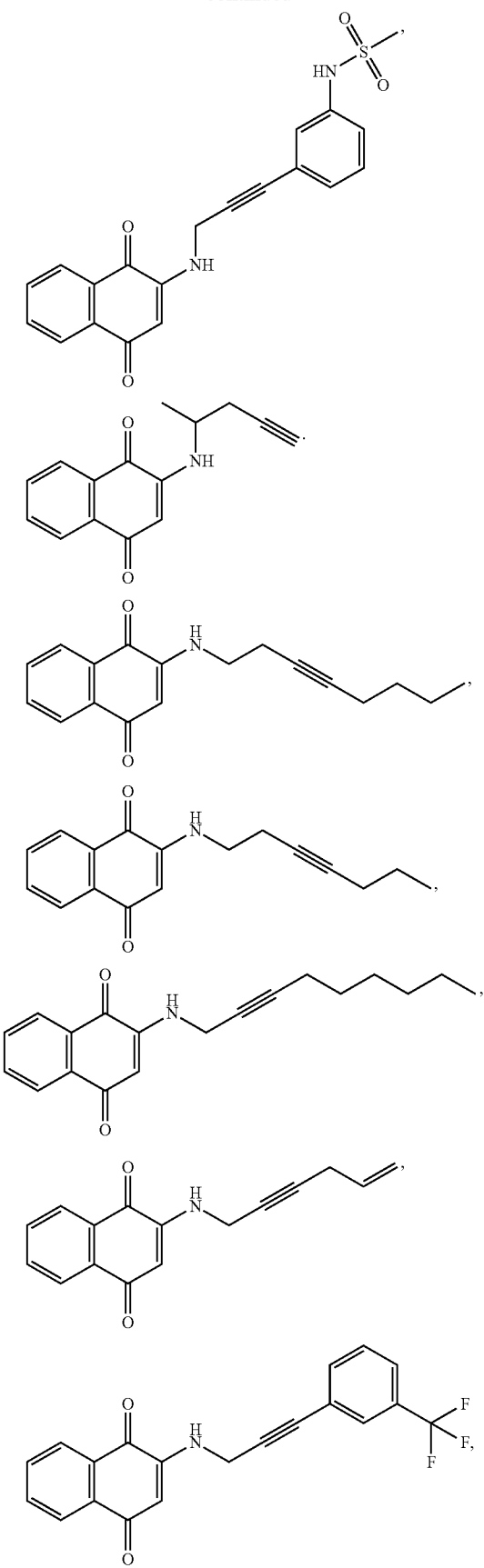

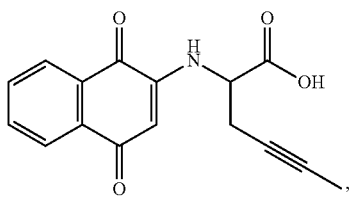

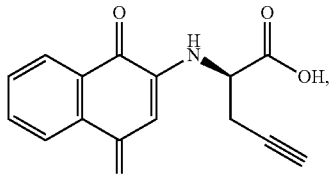

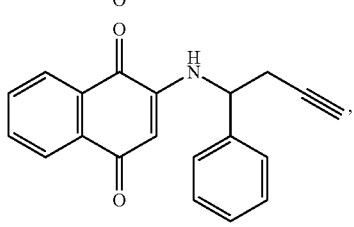

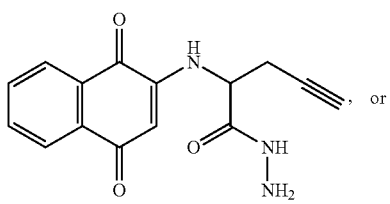

,or

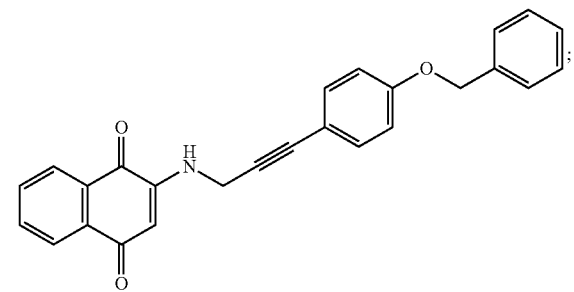 [SMILES: O=C1C=C(NCC#Cc2ccc(OCc3ccccc3)cc2)C(=O)c2ccccc21]

or a pharmaceutically acceptable salt thereof.

In some embodiments, the compound is

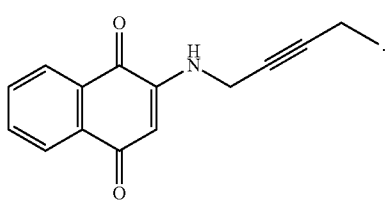 [SMILES: CCC#CCNC1=CC(=O)c2ccccc2C1=O]

In other embodiments, the compound is:

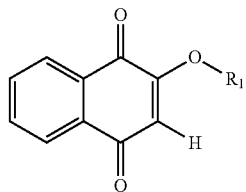

In some embodiments, $R_1$ is

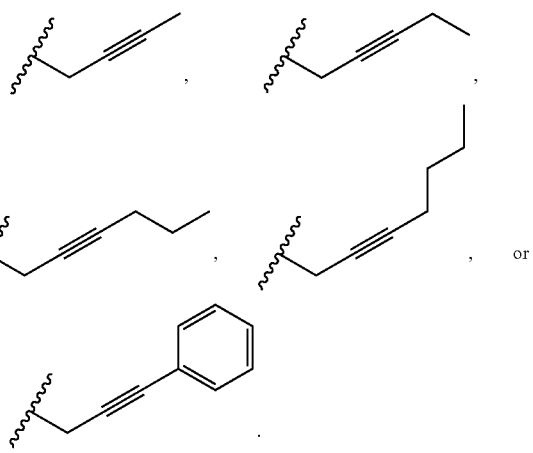

In some embodiments, the compound is not 2-((3-Phenylprop-2-yn-1-yl)amino)naphthalene-1,4-dione, 2-(Isopentylamino)naphthalene-1,4-dione, 2-(Isopentyloxy)naphthalene-1,4-dione, 2-Butoxynaphthalene-1,4-dione, or 2-(Benzyloxy)naphthalene-1,4-dione.

In still yet another aspect, the present disclosure provides compounds of the formula:

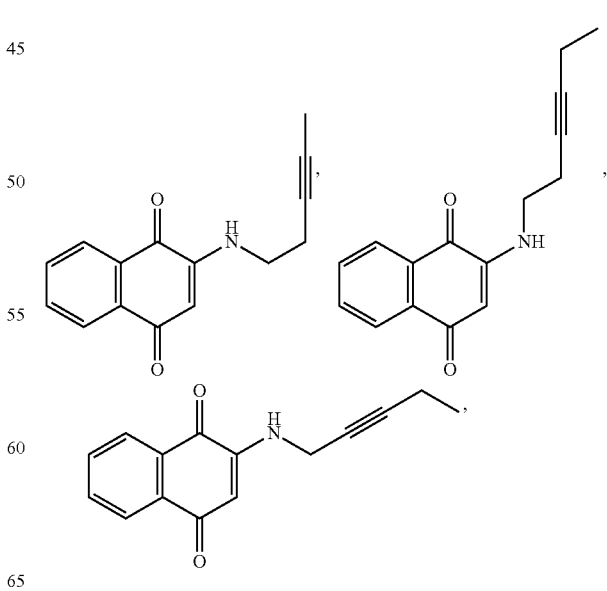

or a pharmaceutically acceptable salt thereof.

In some embodiments, the compound is

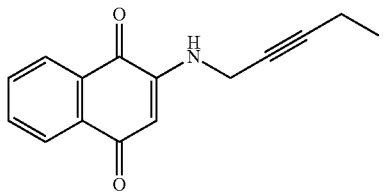 [SMILES: CCC#CCNC1=CC(=O)c2ccccc2C1=O]

or a pharmaceutically acceptable salt thereof. In some embodiments, the compound is comprised in a pharmaceutical composition or in a pharmaceutically acceptable excipient.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A, PK data for 1 in CD-1 mice. The drug was administered at 20 mg/kg via i.p. route in adult mice. Concentrations were recorded using blood draws at six time points and are displayed in red, green, and blue for each individual animal. FIG. 1B, Plasma stability data for 1. In CD-1 mouse plasma ex vivo, the drug is completely stable at room temperature over the course of two hours. Data expressed as mean±SEM for three samples; differences at 0 hr and 2 hr are statistically insignificant.

DESCRIPTION OF ILLUSTRATIVE EMBODIMENTS

Figure 1:
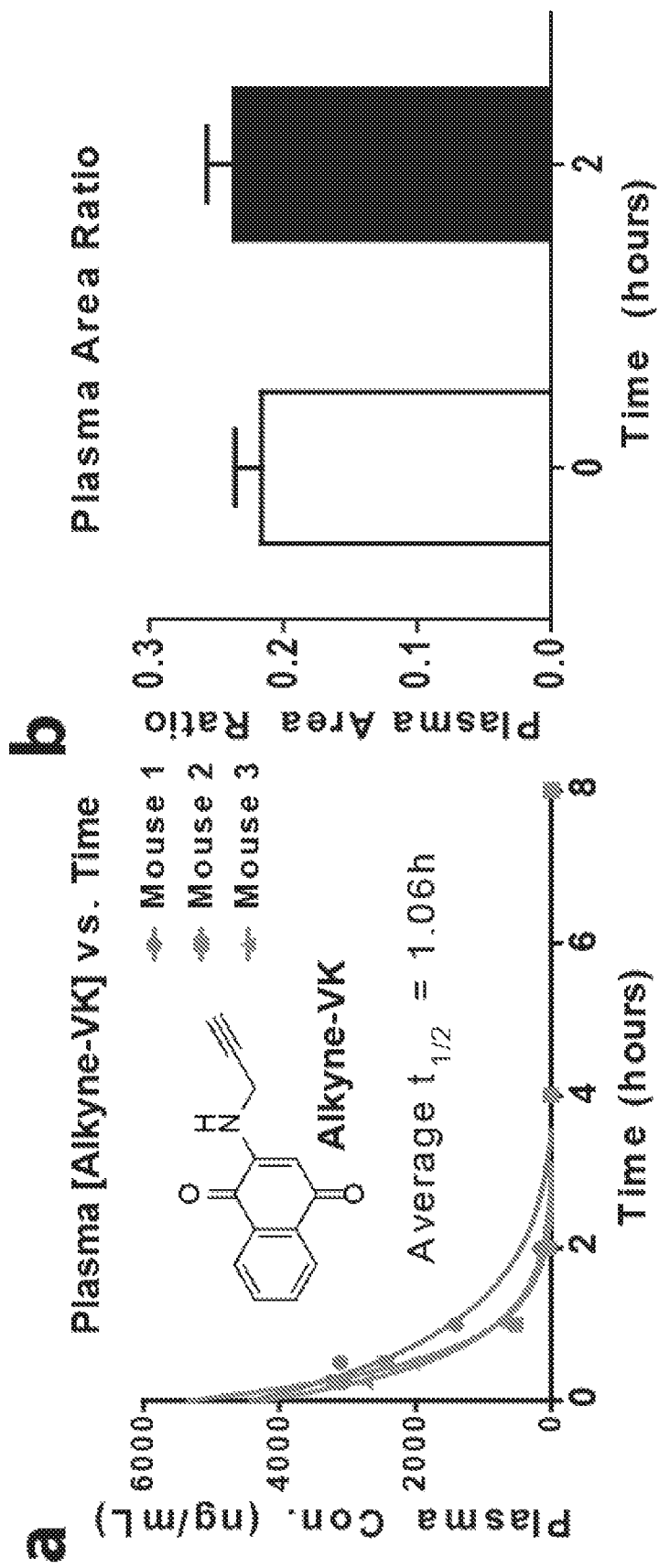
FIG. 1A-B.

In some aspects, the present disclosure provides compounds which contain a 1,4-napthoquinone core which may be used in the treatment of epilepsy and disorders of the mitochondria. These compounds may further comprise an additional unsaturated group such as an alkene or alkyne.

I. DEFINITIONS

When used in the context of a chemical group: "hydrogen" means —H; "hydroxy" means —OH; "oxo" means =O; "carbonyl" means —C(=O)—; "carboxy" means —C(=O)OH (also written as —COOH or —CO₂H); "halo" means independently —F, —Cl, —Br or —I; "amino" means —NH₂; "hydroxyamino" means —NHOH; "nitro" means —NO₂; imino means =NH; "cyano" means —CN; "isocyanate" means —N=C=O; "azido" means —N₃; in a monovalent context "phosphate" means —OP(O)(OH)₂ or a deprotonated form thereof; in a divalent context "phosphate" means —OP(O)(OH)O— or a deprotonated form thereof; "mercapto" means —SH; and "thio" means =S; "sulfonyl" means —S(O)₂—; "aminosulfonyl" means —S(O)₂NH₂; "sulfonyl" means —S(O)₂OH; and "sulfinyl" means —S(O)—.

In the context of chemical formulas, the symbol "—" means a single bond, "=" means a double bond, and "≡" means triple bond. The symbol "- - -" represents an optional bond, which if present is either single or double. The symbol "⌇" represents a single bond or a double bond. Thus, the formula

covers, for example,

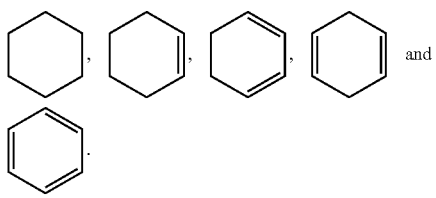

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "∼∼∼", " when drawn perpendicularly across a bond

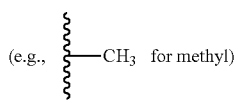

indicates a point of attachment of the group. It is noted that the point of attachment is typically only identified in this manner for larger groups in order to assist the reader in unambiguously identifying a point of attachment. The symbol "◀" means a single bond where the group attached to the thick end of the wedge is "out of the page." The symbol "⫽⫽⫽" means a single bond where the group attached to the thick end of the wedge is "into the page". The symbol "∼∼∼" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a variable is depicted as a "floating group" on a ring system, for example, the group "R" in the formula:

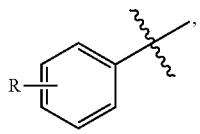

then the variable may replace any hydrogen atom attached to any of the ring atoms, including a depicted, implied, or expressly defined hydrogen, so long as a stable structure is formed. When a variable is depicted as a "floating group" on a fused ring system, as for example the group "R" in the formula:

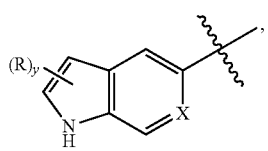

then the variable may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the R enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question, e.g., it is understood that the minimum number of carbon atoms in the group "alkenyl$_{(C\leq8)}$" or the class "alkene$_{(C\leq8)}$" is two. Compare with "alkoxy$_{(C\leq10)}$", which designates alkoxy groups having from 1 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous. When any of the chemical groups or compound classes defined herein is modified by the term "substituted", any carbon atom(s) in the moiety replacing a hydrogen atom is not counted. Thus methoxyhexyl, which has a total of seven carbon atoms, is an example of a substituted alkyl$_{(C1-6)}$. Unless specified otherwise, any chemical group or compound class listed in a claim set without a carbon atom limit has a carbon atom limit of less than or equal to twelve.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound or chemical group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" when used to modify a compound or a chemical group refers to a planar unsaturated ring of atoms with 4n+2 electrons in a fully conjugated cyclic π system.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH₃ (Me), —CH₂CH₃ (Et), —CH₂CH₂CH₃ (n-Pr or propyl), —CH(CH₃)₂ (i-Pr, ⁱPr or isopropyl), —CH₂CH₂CH₂CH₃ (n-Bu), —CH(CH₃)CH₂CH₃ (sec-butyl), —CH₂CH(CH₃)₂ (isobutyl), —C(CH₃)₃ (ten-butyl, t-butyl, t-Bu or ᵗBu), and —CH₂C(CH₃)₃ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH₂— (methylene), —CH₂CH₂—, and —CH₂C(CH₃)₂CH₂—, and —CH₂CH₂CH₂— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH₂, =CH(CH₂CH₃), and =C(CH₃)₂. An "alkane" refers to the class of compounds having the formula H—R, wherein R is alkyl as this term is defined above. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂. The following groups are non-limiting examples of substituted alkyl groups: —CH₂OH, —CH₂Cl, —CF₃, —CH₂CN, —CH₂C(O)OH, —CH₂C(O)OCH₃, —CH₂C(O)NH₂, —CH₂C(O)CH₃, —CH₂OCH₃, —CH₂OC(O)CH₃, —CH₂NH₂, —CH₂N(CH₃)₂, and —CH₂CH₂Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH₂Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH₂F, —CF₃, and —CH₂CF₃ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH₂)₂ (cyclopropyl), cyclobutyl, cyclopentyl, or cyclohexyl (Cy). As used herein, the term does not preclude the presence of one or more alkyl groups (carbon number limitation permitting) attached to a carbon atom of the non-aromatic ring structure. The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

is a non-limiting example of cycloalkanediyl group. A "cycloalkane" refers to the class of compounds having the formula H—R, wherein R is cycloalkyl as this term is defined above. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂.

The term "alkenyl" when used without the "substituted" modifier refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH₂ (vinyl), —CH=CHCH₃, —CH=CHCH₂CH₃, —CH₂CH=CH₂ (allyl), —CH₂CH=CHCH₃, and —CH=CHCH=CH₂. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH₃)CH₂—, —CH=CHCH₂—, and —CH₂CH=CHCH₂— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly, the terms "terminal alkene" and "α-olefin" are synonymous and refer to an alkene having just one carbon-carbon double bond, wherein that bond is part of a vinyl group at an end of the molecule. When any of these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂. The groups —CH=CHF, —CH=CHCl and —CH=CHBr are non-limiting examples of substituted alkenyl groups.

The term "alkynyl" when used without the "substituted" modifier refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH₃, and —CH₂C≡CCH₃ are non-limiting examples of alkynyl groups. An "alkyne" refers to the class of compounds having the formula H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aryl" when used without the "substituted" modifier refers to a monovalent unsaturated aromatic group with an aromatic carbon atom as the point of attachment, said carbon atom forming part of a one or more aromatic ring structure, wherein the ring atoms are all carbon, and wherein the group consists of no atoms other than carbon and hydrogen. If more than one ring is present, the rings may be fused or unfused. Unfused rings are connected with a covalent bond. As used herein, the term aryl does not preclude the presence of one or more alkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl (e.g., 4-phenylphenyl). The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term arenediyl does not preclude the presence of one or more alkyl groups (carbon number limitation permitting) attached to the first aromatic ring or any additional aromatic ring present. If more than one ring is present, the rings may be fused or unfused. Unfused rings are connected with a covalent bond. Non-limiting examples of arenediyl groups include:

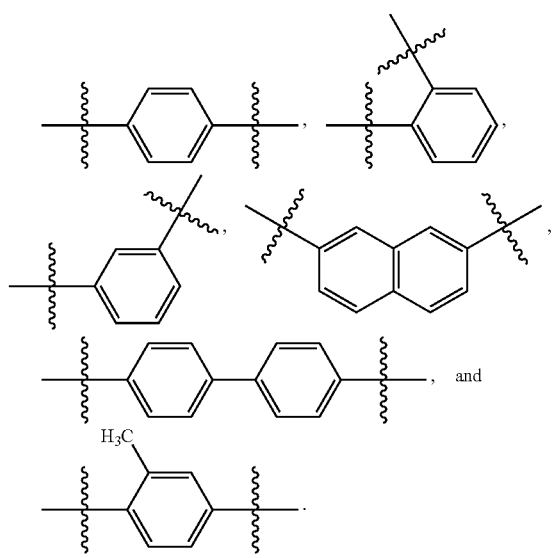

An "arene" refers to the class of compounds having the formula H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aralkyl" when used without the "substituted" modifier refers to the monovalent group-alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. Unfused rings are connected with a covalent bond. As used herein, the term heteroaryl does not preclude the presence of one or more alkyl or aryl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "acyl" when used without the "substituted" modifier refers to the group —C(O)R, in which R is a hydrogen, alkyl, cycloalkyl, or aryl as those terms are defined above. The groups, —CHO, —C(O)CH$_3$ (acetyl, Ac), —C(O)CH$_2$CH$_3$, —C(O)CH(CH$_3$)$_2$, —C(O)CH(CH$_2$)$_2$, —C(O)C$_6$H$_5$, and —C(O)C$_6$H$_4$CH$_3$ are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkyl group, as defined above, attached to a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), —OC(CH$_3$)$_3$ (tert-butoxy), —OCH(CH$_2$)$_2$, —O-cyclopentyl, and —O-cyclohexyl. The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkylamino" when used without the "substituted" modifier refers to the group —NHR, in which R is an alkyl, as that term is defined above. Non-limiting examples include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$ and —N(CH$_3$)(CH$_2$CH$_3$). The terms "cycloalkylamino", "alkenylamino", "alkynylamino", "arylamino", "aralkylamino", "heteroarylamino", "heterocycloalkylamino", "alkoxyamino", and "alkylsulfonylamino" when used without the "substituted" modifier, refers to groups, defined as —NHR, in which R is cycloalkyl, alkenyl, alkynyl, aryl, aralkyl, heteroaryl, heterocycloalkyl, alkoxy, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. When any of these terms is used with the "substituted" modifier one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —NHC(O)OCH$_3$ and —NHC(O)NHCH$_3$ are non-limiting examples of substituted amido groups.

An "active ingredient" (AI) (also referred to as an active compound, active substance, active agent, pharmaceutical agent, agent, biologically active molecule, or a therapeutic compound) is the ingredient in a pharmaceutical drug or a pesticide that is biologically active. The similar terms active pharmaceutical ingredient (API) and bulk active are also used in medicine, and the term active substance may be used for pesticide formulations.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating or preventing a disease, is an amount sufficient to effect such treatment or prevention of the disease.

An "excipient" is a pharmaceutically acceptable substance formulated along with the active ingredient(s) of a medication, pharmaceutical composition, formulation, or drug delivery system. Excipients may be used, for example, to stabilize the composition, to bulk up the composition (thus often referred to as "bulking agents," "fillers," or "diluents" when used for this purpose), or to confer a therapeutic enhancement on the active ingredient in the final dosage form, such as facilitating drug absorption, reducing viscosity, or enhancing solubility. Excipients include pharmaceutically acceptable versions of antiadherents, binders, coatings, colors, disintegrants, flavors, glidants, lubricants, preservatives, sorbents, sweeteners, and vehicles. The main excipient that serves as a medium for conveying the active ingredient is usually called the vehicle. Excipients may also be used in the manufacturing process, for example, to aid in the handling of the active substance, such as by facilitating powder flowability or non-stick properties, in addition to aiding in vitro stability such as prevention of denaturation or aggregation over the expected shelf life. The suitability of an excipient will typically vary depending on the route of administration, the dosage form, the active ingredient, as well as other factors.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

A "pharmaceutically acceptable carrier," "drug carrier," or simply "carrier" is a pharmaceutically acceptable substance formulated along with the active ingredient medication that is involved in carrying, delivering and/or transporting a chemical agent. Drug carriers may be used to improve the delivery and the effectiveness of drugs, including for example, controlled-release technology to modulate drug bioavailability, decrease drug metabolism, and/or reduce drug toxicity. Some drug carriers may increase the effectiveness of drug delivery to the specific target sites. Examples of carriers include: liposomes, microspheres (e.g., made of poly(lactic-co-glycolic) acid), albumin microspheres, synthetic polymers, nanofibers, protein-DNA complexes, protein conjugates, erythrocytes, virosomes, and dendrimers.

A "pharmaceutical drug" (also referred to as a pharmaceutical, pharmaceutical agent, pharmaceutical preparation, pharmaceutical composition, pharmaceutical formulation, pharmaceutical product, medicinal product, medicine, medication, medicament, or simply a drug) is a drug used to diagnose, cure, treat, or prevent disease. An active ingredient (AI) (defined above) is the ingredient in a pharmaceutical drug or a pesticide that is biologically active. The similar terms active pharmaceutical ingredient (API) and bulk active are also used in medicine, and the term active substance may be used for pesticide formulations. Some medications and pesticide products may contain more than one active ingredient. In contrast with the active ingredients, the inactive ingredients are usually called excipients (defined above) in pharmaceutical contexts.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

II. COMPOUNDS OF THE PRESENT INVENTION

The compounds of the present invention (also referred to as "compounds of the present disclosure") are shown, for example, above, in the summary of the invention section, and in the claims below. They may be made using the synthetic methods outlined in the Examples section. These methods can be further modified and optimized using the principles and techniques of organic chemistry as applied by a person skilled in the art. Such principles and techniques are taught, for example, in Smith, *March's Advanced Organic Chemistry: Reactions, Mechanisms, and Structure*, (2013), which is incorporated by reference herein. In addition, the synthetic methods may be further modified and optimized for preparative, pilot- or large-scale production, either batch of continuous, using the principles and techniques of process chemistry as applied by a person skilled in the art. Such principles and techniques are taught, for example, in Anderson, *Practical Process Research & Development—A Guide for Organic Chemists* (2012), which is incorporated by reference herein.

In some aspects, compounds are provided herein having the structure:

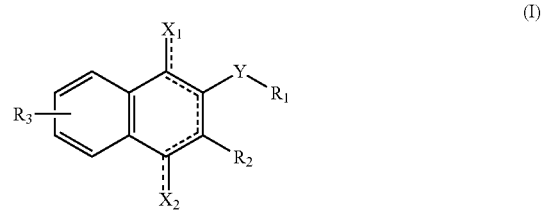

(I)

wherein:
$X_1$ and $X_2$ are each independently oxo or hydroxy;
$R_2$ is hydrogen, $C_{1-6}$ alkyl, $C_{6-12}$ aryl, $C_{5-12}$ heteroaryl, $C_{1-6}$ alkanediyl-$C_{6-12}$ aryl, —NH—CO—$C_{6-12}$ aryl, —$C_{1-4}$alkanediyl-O—$C_{6-12}$ aryl, halogen, or a substituted version thereof;
$R_3$ is hydrogen, amino, cyano, halo, hydroxy, nitro, aminosulfonyl, hydroxysulfonyl, $C_{1-6}$ alkyl, $C_{1-6}$ acyl, $C_{1-6}$ alkoxy, $C_{1-6}$ alkylamino, $C_{1-8}$ dialkylamino, or a substituted version of the last five groups;
Y is —NH— or —O—;
wherein when Y is —NH— and $R_2$ is hydrogen,
$R_1$ is $C_{6-18}$ alkenyl; —$(CH_2)_xC\equiv CR_a$; wherein: x is 1, 2, 3, or 4 and $R_a$ is $C_{1-8}$ alkyl, $C_{1-8}$ alkenyl, $C_{1-8}$ alkynyl, $C_{6-12}$ aryl, $C_{1-12}$ heteroaryl, or a substituted version of any of these groups;
a group of the formula:

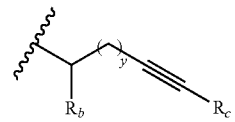

wherein:
$R_b$ is $C_{1-8}$ alkyl, substituted $C_{1-8}$ alkyl, $C_{6-12}$ aryl, substituted $C_{6-12}$ aryl, or —C(O)$R_d$;
wherein: $R_d$ is amino, hydroxy, —NHNH$_2$, $C_{1-6}$ alkoxy, $C_{1-6}$ alkylamino, or $C_{1-8}$ dialkylamino, or a substituted version of any of the last three groups; or
$R_c$ is hydrogen, $C_{1-8}$ alkyl, $C_{1-8}$ alkenyl, $C_{1-8}$ alkynyl, $C_{6-12}$ aryl, $C_{1-12}$ heteroaryl, or a substituted version of any of the last five groups; and
y is 0, 1, or 2; or
a group of the formula:

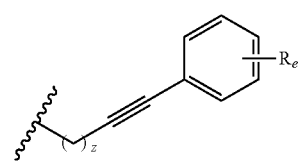

wherein:
z is 1, 2, or 3
$R_e$ is halo, $C_{1-6}$ alkyl, $C_{1-6}$ alkoxy, $C_{1-6}$ alkylsulfonylamino, or a substituted version of any of the last three groups; or a group of the formula:

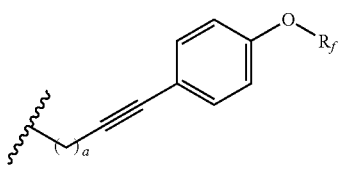

wherein:
a is 1, 2, or 3
$R_f$ is $C_{6-12}$ aryl, $C_{7-12}$ aralkyl, or a substituted version of any of either groups;
wherein when Y is —NH— and $R_2$ is not hydrogen; then:
$R_1$ is $C_{6-12}$ alkenyl, $C_{6-12}$ alkynyl, $C_{6-12}$ aryl, $C_{1-12}$ heteroaryl, or a substituted version of any of these groups, or —Y'—$X_3$—$R_5$, wherein:
Y' is $C_{1-6}$ alkynediyl, $C_{6-12}$ arenediyl, or a substituted version of either group;
$X_3$ is a covalent bond, —O—, —NHC(O)—, or —C(O)NH—; and
$R_g$ is $C_{1-6}$ alkyl $C_{1-8}$ alkenyl, $C_{1-8}$ alkynyl, $C_{6-12}$ aryl, $C_{1-12}$ heteroaryl, $C_{7-12}$ aralkyl, or a substituted version of either group; or
wherein when Y is —O—,
$R_1$ is $C_{1-18}$ alkyl, substituted $C_{1-18}$ alkyl, $C_{1-18}$ alkenyl, substituted $C_{1-18}$ alkenyl, $C_{1-18}$ alkynyl, and substituted $C_{1-18}$ alkynyl;
a group of the formula:

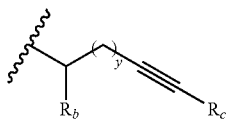

wherein:
$R_b$ is $C_{1-8}$ alkyl, substituted $C_{1-8}$ alkyl, $C_{6-12}$ aryl, substituted $C_{6-12}$ aryl, or —C(O)$R_d$;
wherein: $R_d$ is amino, hydroxy, —NHNH$_2$, $C_{1-6}$ alkoxy, $C_{1-6}$ alkylamino, or Cis dialkylamino, or a substituted version of any of the last three groups; or
$R_c$ is hydrogen, $C_{1-8}$ alkyl, $C_{1-8}$ alkenyl, $C_{1-8}$ alkynyl, $C_{6-12}$ aryl, $C_{1-12}$ heteroaryl, or a substituted version of any of the last five groups; and
y is 0, 1, 2, or 3; or
or a pharmaceutically acceptable salt thereof;

Compounds described herein may display improved properties as compared to previous compounds. For example, a compound including a 1,4-naphthoquinone scaffold (a structural feature in the Vitamin K cofactor family) was identified that protected neuronal mitochondrial health in vitro and demonstrated in vivo anti-seizure activity in mouse and zebrafish models: the toxicant-induced zebrafish seizure model (Baraban et al., 2005), the minimal clonic (6 Hz) mouse seizure model, and the corneal-kindled mouse model of medication-resistant epilepsy (Rahn et al., 2013). However, the compound's poor pharmacokinetic profile limits its potential as an AED (Rahn et al., 2013). In contrast and as shown in the below examples, several compounds are provided that with optimized anti-seizure activity in zebrafish and improved pharmacokinetic properties in mice, that include 2-pentynyl amine substituent or an isoamyloxy group on the 1,4-naphthoquinone scaffold. These promising results indicate that these new compounds warrant further development as potential AEDs.

All of the compounds of the present invention may be useful for the prevention and treatment of one or more diseases or disorders discussed herein or otherwise. In some embodiments, one or more of the compounds characterized or exemplified herein as an intermediate, a metabolite, and/or prodrug, may nevertheless also be useful for the prevention and treatment of one or more diseases or disorders. As such unless explicitly stated to the contrary, all of the compounds of the present invention are deemed "active compounds" and "therapeutic compounds" that are contemplated for use as active pharmaceutical ingredients (APIs). Actual suitability for human or veterinary use is typically determined using a combination of clinical trial protocols and regulatory procedures, such as those administered by the Food and Drug Administration (FDA). In the United States, the FDA is responsible for protecting the public health by assuring the safety, effectiveness, quality, and security of human and veterinary drugs, vaccines and other biological products, and medical devices.

In some embodiments, the compounds of the present invention have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

Compounds of the present invention may contain one or more asymmetrically-substituted carbon or nitrogen atoms and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration.

Chemical formulas used to represent compounds of the present invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

Compounds of the present invention may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It will be appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present invention.

The above methods can be further modified and optimized for preparative, pilot- or large-scale production, either batch of continuous, using the principles and techniques of process chemistry as applied by a person skilled in the art. Such principles and techniques are taught, for example, in *Practical Process Research & Development* (2012), which is incorporated by reference herein.

III. TREATMENT OF DISEASES

In some aspects, the compounds of the present invention may be used to treat a disease such as, e.g., a neurological disease or injury (e.g., epilepsy, medication-resistant epilepsy, bipolar disorder or the manic phase of bipolar disorder, headaches, migraines, or a traumatic brain injury) or a mitochondrial disease (e.g., mitochondrial DNA (mtDNA) depletion syndrome (MDS), or dysfunctional mitochondrial respiratory chain disorder). In some aspects, the compound may be used to treat a metabolic disease or a mitochondrial disease in a mammalian subject, such as a human.

In some embodiments, the disease is a neurological disease such as, e.g., epilepsy, medication-resistant epilepsy, bipolar disorder or the manic phase of bipolar disorder, headaches, migraines, a traumatic brain injury, Parkinson's disease, Alzheimer's disease, Huntington's disease, Friedereich's Ataxia, or optic atrophy. As shown in the below examples, compounds provided herein displayed anti-seizure activity in zebrafish and improved pharmacokinetic properties in mice. In some embodiments, compounds provided herein may be used to treat epilepsy or as an AED.

Mitochondrial DNA depletion syndrome (also called MDS) are a group of autosomal recessive disorders that are characterized by a significant drop in mtDNA. The condition is often fatal in infancy and early childhood, and no approved therapies currently exist to treat the disease. Particular forms of MDS include: myopathic form (typically involving mutations in the TK2 gene), encephalomyopathic form (typically involving mutations in SUCLA2 or RRM2B), the hepatopathic form (typically involving mutations in DGUOK, POLG, or MPV17), and the neurogastrointestinal form. In some embodiments, efficacy of a compound disclosed herein may be tested using an Optic Atrophy 1 gene (OPA1) model of MDS.

Mitochondrial respiratory chain (MRC) function generally depends on the coordinated expression of both nuclear (nDNA) and mitochondrial (mtDNA) genomes. Thus, mitochondrial diseases can for example be caused by genetic defects in either the mitochondrial or the nuclear genome, or in the cross-talk between the two. This impaired cross-talk can result in nuclear-mitochondrial intergenomic communication disorders, which are typically characterized by loss or instability of the mitochondrial genome and, in turn, impaired maintenance of qualitative and quantitative mtDNA integrity. In children, most MRC disorders are associated with nuclear gene defects rather than alterations in the mtDNA itself. The MDSs are a clinically heterogeneous group of disorders with an autosomal recessive pattern of transmission that have onset in infancy or early childhood and are characterized by a reduced number of copies of mtDNA in affected tissues and organs. The MDSs include at least four clinical presentations: hepatocerebral, myopathic, encephalomyopathic and neurogastrointestinal. MDS is further described in, e.g., Nogueira et al. (2014).

In some embodiments, a compound of the present disclosure may be used to treat a mitochondrial disease, such as MDS, Alpers syndrome, Leigh's Disease, autism, Parkinson's disease, Huntington's disease, Alzheimer's disease, amyotrophic lateral sclerosis (ALS) or Lou Gehrig's disease, optic atrophy, cardiomyopathy, muscular dystrophy, chronic fatigue, Friedreich ataxia, a progressive palsy, Charcot-Marie-Tooth disease, an acute kidney injury (AKI), a chronic kidney injury or disease, obesity, or diabetes mellitus. In some embodiments, the metabolic disease is characterized by a deficiency in the subject of metabolizing vitamin $K_3$ into vitamin $K_2$. The mitochondrial disease may be, e.g., a mitochondrial myopathy, Kearns-Sayre syndrome (KSS), chronic progressive external ophthalmoplegia (CPEO), diabetes mellitus and deafness (DAD), Leber's hereditary optic neuropathy (LHON), Leigh syndrome, "neuropathy, ataxia, retinitis pigmentosa, and ptosis" (NARP), "myoneurogenic gastrointestinal encephalopathy" (MNGIE), MERRF, "mitochondrial myopathy, encephalomyopathy, lactic acidosis, or stroke-like symptoms" (MELAS). In some preferred embodiments, the mitochondrial disease is Friedreich's ataxia. Without wishing to be bound by any theory, data is provided herein that is consistent with the idea that some of the compounds of the present invention may affect or target mitochondrial function.

IV. PHARMACEUTICAL FORMULATIONS AND ROUTES OF ADMINISTRATION

For the purpose of administration to a patient in need of such treatment, pharmaceutical formulations (also referred to as a pharmaceutical preparations, pharmaceutical compositions, pharmaceutical products, medicinal products, medicines, medications, or medicaments) comprise a therapeutically effective amount of a compound of the present invention formulated with one or more excipients and/or drug carriers appropriate to the indicated route of administration. In some embodiments, the compounds of the present invention are formulated in a manner amenable for the treatment of human and/or veterinary patients. In some embodiments, formulation comprises admixing or combining one or more of the compounds of the present invention with one or more of the following excipients: lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol. In some embodiments, e.g., for oral administration, the pharmaceutical formulation may be tableted or encapsulated. In some embodiments, the compounds may be dissolved or slurried in water, polyethylene glycol, propylene glycol, ethanol, corn oil, cottonseed oil, peanut oil, sesame oil, benzyl alcohol, sodium chloride, and/or various buffers. Pharmaceutical formulations may be subjected to conventional pharmaceutical operations, such as sterilization and/or may contain drug carriers and/or excipients such as preservatives, stabilizers, wetting agents, emulsifiers, encapsulating agents such as lipids, dendrimers, polymers, proteins such as albumin, or nucleic acids, and buffers, etc.

Pharmaceutical formulations may be administered by a variety of methods, e.g., orally or by injection (e.g. subcutaneous, intravenous, intraperitoneal, etc.). Depending on the route of administration, the compounds of the present invention may be coated in a material to protect the compound from the action of acids and other natural conditions which may inactivate the compound. To administer the active compound by other than parenteral administration, it may be necessary to coat the compound with, or co-administer the compound with, a material to prevent its inactivation. For example, the active compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The compounds of the present invention may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

The compounds of the present invention can be administered orally, for example, with an inert diluent or an assimilable edible carrier. The compounds and other ingredients may also be enclosed in a hard or soft shell gelatin capsule, compressed into tablets, or incorporated directly into the subject's diet. For oral therapeutic administration, the compounds of the present invention may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such pharmaceutical formulations is such that a suitable dosage will be obtained.

In some embodiments, the therapeutic compound may also be administered topically to the skin, eye, or mucosa. Alternatively, if local delivery to the lungs is desired the therapeutic compound may be administered by inhalation in a dry-powder or aerosol formulation.

In some embodiments, it may be advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. In some embodiments, the specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient. In some embodiments, active compounds are administered at a therapeutically effective dosage sufficient to treat a condition associated with a condition in a patient. For example, the efficacy of a compound can be evaluated in an animal model system that may be predictive of efficacy in treating the disease in a human or another animal.

In some embodiments, the effective dose range for the therapeutic compound can be extrapolated from effective doses determined in animal studies for a variety of different animals. In general a human equivalent dose (HED) in mg/kg can be calculated in accordance with the following formula (see, e.g., Reagan-Shaw et al., FASEB J., 22(3): 659-661, 2008, which is incorporated herein by reference):

$$HED(mg/kg)=\text{Animal dose (mg/kg)} \times (\text{Animal } K_m/\text{Human } K_m)$$

Use of the $K_m$ factors in conversion results in more accurate HED values, which are based on body surface area (BSA) rather than only on body mass. $K_m$ values for humans and various animals are well known. For example, the $K_m$ for an average 60 kg human (with a BSA of 1.6 m$^2$) is 37, whereas a 20 kg child (BSA 0.8 m$^2$) would have a $K_m$ of 25. $K_m$ for some relevant animal models are also well known, including: mice $K_m$ of 3 (given a weight of 0.02 kg and BSA of 0.007); hamster $K_m$ of 5 (given a weight of 0.08 kg and BSA of 0.02); rat $K_m$ of 6 (given a weight of 0.15 kg and BSA of 0.025) and monkey $K_m$ of 12 (given a weight of 3 kg and BSA of 0.24).

Precise amounts of the therapeutic composition depend on the judgment of the practitioner and are peculiar to each individual. Nonetheless, a calculated HED dose provides a general guide. Other factors affecting the dose include the physical and clinical state of the patient, the route of administration, the intended goal of treatment and the potency, stability and toxicity of the particular therapeutic formulation.

The actual dosage amount of a compound of the present disclosure or composition comprising a compound of the present disclosure administered to a subject may be determined by physical and physiological factors such as type of animal treated, age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

In some embodiments, the therapeutically effective amount typically will vary from about 0.001 mg/kg to about 1000 mg/kg, from about 0.01 mg/kg to about 750 mg/kg, from about 100 mg/kg to about 500 mg/kg, from about 1 mg/kg to about 250 mg/kg, from about 10 mg/kg to about 150 mg/kg in one or more dose administrations daily, for one or several days (e.g., depending of the mode of administration and the factors discussed above). Other suitable dose ranges include 1 mg to 10,000 mg per day, 100 mg to 10,000 mg per day, 500 mg to 10,000 mg per day, and 500 mg to 1,000 mg per day. In some particular embodiments, the amount is less than 10,000 mg per day with a range of 750 mg to 9,000 mg per day.

In some embodiments, the amount of the active compound in the pharmaceutical formulation is from about 2 to about 75 weight percent. In some of these embodiments, the amount if from about 25 to about 60 weight percent.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may be taken orally and that the timing of which is or is not dependent upon food intake. Thus, for example, the agent can be taken every morning and/or every evening, regardless of when the subject has eaten or will eat.

Pharmaceutical compositions of the present invention comprise an effective amount of one or more compounds of the present invention or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one compound of the present invention or additional active ingredient will be known to those of skill in the art in light of the present disclosure, as exemplified by Remington: The Science and Practice of Pharmacy, 21$^{st}$ Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The compound of the present invention may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The compound of the present invention may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include a compound of the present invention, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the compound of the present invention may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

A. Alimentary Compositions and Formulations

In preferred embodiments of the present invention, the compound of the present invention are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

B. Parenteral Compositions and Formulations

In further embodiments, a compound of the present invention may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,613,308, 5,466,468, 5,543,158; 5,641, 515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580, 1975). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

C. Miscellaneous Pharmaceutical Compositions and Formulations

In other preferred embodiments of the invention, the active compound may be formulated for administration via various miscellaneous routes, for example, topical or transdermal administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Development of Vitamin K Analog 2-amino- and 2-alkoxy-1,4-napthoquinone Compounds as Potential Therapeutics for Medication-Resistant Epilepsy A. Results
  i. Study Rationale and Medicinal Chemistry.

Previous studies of synthetic VK analogs identified several highly neuroprotective 1,4-naphthoquinone derivatives with substituted amino groups attached at the 2-position. In vivo screening of these compounds in the PTZ-induced zebrafish seizure model identified the alkyne-containing derivative, 1 (Table 1), as possessing highly potent antiseizure activity in zebrafish and mouse seizure models [Rahn] (Stables et al., 2003; Stables and Kupferberg, 1997). The compound showed efficacy in both the 6 Hz psychomotor (minimal clonic) seizure model—the only acute model for medication-resistant epilepsy (Barton et al., 2001; Metcalf et al., 2017)—and the mouse corneal kindling model, a chronic model for medication-resistant epilepsy (Rowley and White, 2010; Matagne and Klitgaard, 1998). In the 6 Hz model, 4/4 animals were protected from seizures after 0.25 hr, however protection dropped to zero by 4 hr (Rahn et al., 2014). While the compound is stable, displaying no catabolic conversion even after 2 hr in mouse serum, 1 displays a short half-life of ~1 hr when administered by intraperitoneal injection (20 mg/kg) to adult mice (FIG. 1). The rapid decrease in plasma concentration in vivo compared to the lack of degradation in plasma ex vivo suggests either rapid hepatic metabolism or diminished renal reuptake. This finding is not surprising, as terminal alkynes are known to be oxidized and excreted rapidly by the liver and kidney. The clearance rate of 1 in mice correlates with the short protective timeframe in the mouse models of epilepsy.

Figure 2:
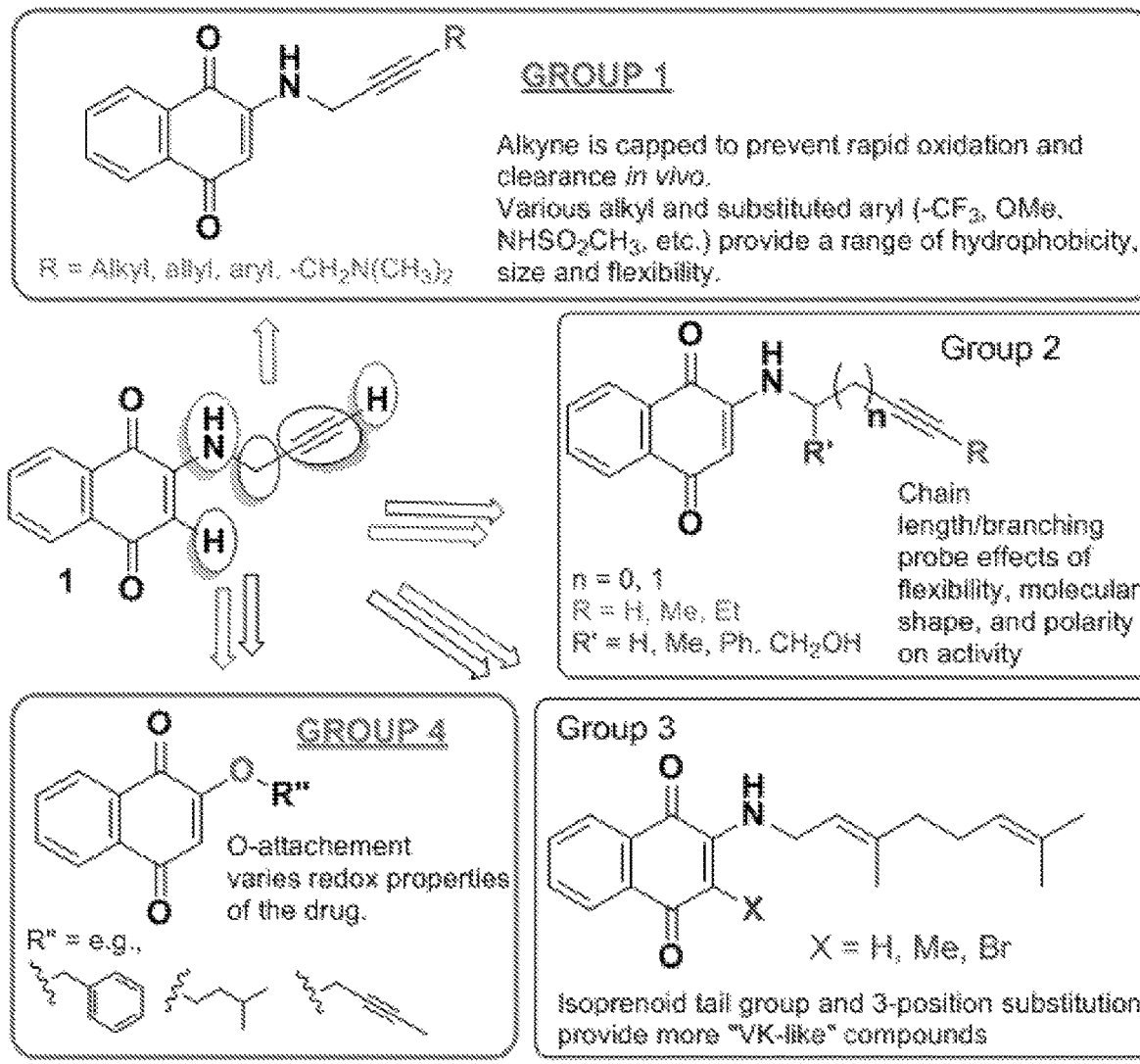
FIG. 2: Classes of compounds examined as potential AEDs.

Thus, improving 1's drug-like properties and optimizing protection in the PTZ-induced zebrafish seizure model could lead to an AED with prolonged efficacy in vivo. FIG. 2 illustrates the rationale behind the medicinal chemistry. All of the compounds synthesized for this study maintain the 1,4-naphthoquinone pharmacophore. The primary targets (Group 1) possessed 1's 2-propargylamino group plus an end-capping organic group appended to the alkyne. Without wishing to be bound by any theory, it is believed that substituting the terminal alkyne would prolong in vivo half-life. A second set (Group 2) introduced structural alterations closer to the naphthoquinone core, either with branching alpha to the nitrogen or lengthening the spacer between nitrogen and alkyne to two carbons, or both of these modifications. The goal was to probe effects of variations in polarity, flexibility, and molecular shape on activity. Several compounds (Group 3) incorporated an isoprenoid chain to the nitrogen, to model the hydrophobic four isoprenoid-repeat tail found in MK4. One derivative with a 3-methyl group, as found in MK4, was synthesized.

Figure 3:
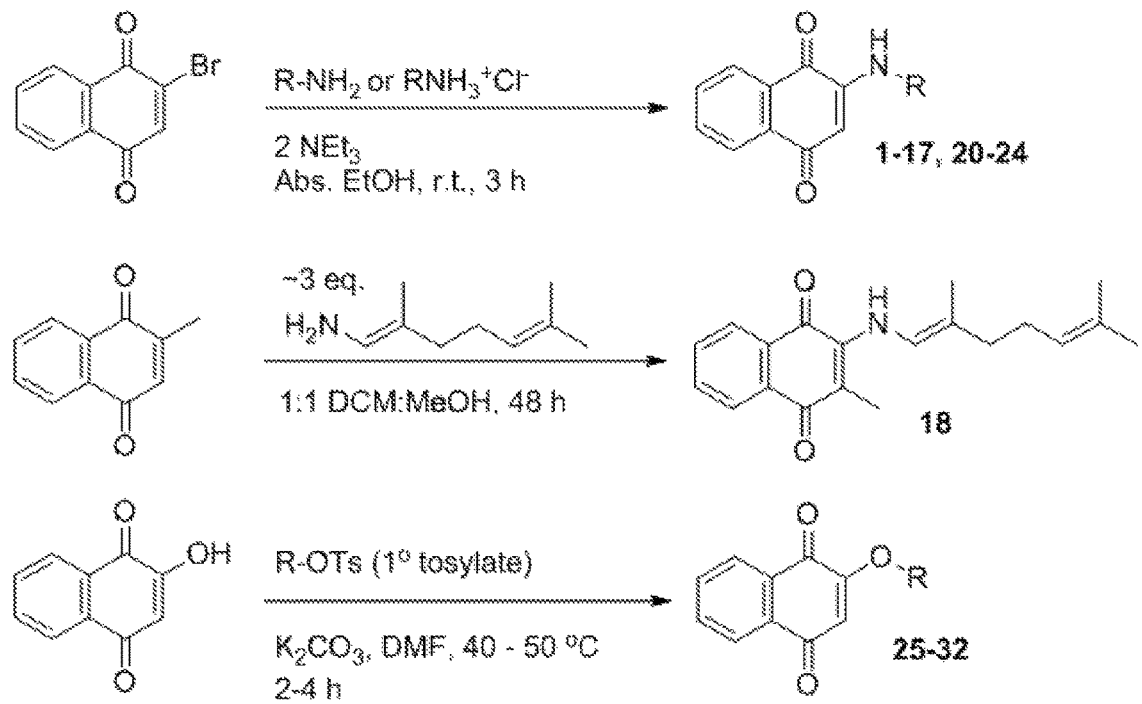
FIG. 3: Chemical syntheses of compounds examined as potential AEDs.

These 2-amino-substituted 1,4-napthoquinones were prepared by previously published methods (Josey et al., 2013), or using modifications of reported preparations (Valente et al., 2007; Tandon et al., 2004), involving addition of the appropriate amine as either free base or ammonium chloride salt to an ethanolic solution of 2-bromo-1,4-naphthoquinone in the presence of triethylamine. The amine reactants were obtained from commercial sources or prepared from the corresponding commercial alcohols, which were tosylated and subjected to classical Gabriel synthesis: The tosylate converted to a phthalimide derivative, and the amine generated by heating in the presence of hydrazine (FIG. 3). Final products were isolated in modest yields (typically, 20-50% one-step yields) as yellow, orange, or deep red solids after purification by reversed-phase chromatography on pre-packed C18 silica columns. A byproduct observed in the preparation of these compounds was the 3-bromo derivative, as evidenced by LC-MS (with clear [M+H]$^+$ peaks corresponding to the compounds, as well as high intensity [M+H+2]$^+$ peaks corresponding to the 81Br-containing molecules). These bromo-substituted compounds likely formed via oxidation of the Michael addition intermediate of amine reacted with 2-bromo-1,4-napthoquinone, rather than by elimination of bromide.

A number of 2-alkoxy-1,4-naphthoquinone targets (Group 4, FIG. 2) were also prepared. Replacement of the nitrogen attachment to the naphthoquinone scaffold with oxygen alters the redox properties, and thus mitochondrial electron-carrying properties, of the naphthoquinone moiety. Without wishing to be bound by any theory, it is believed that redox potential should tune drug activity based on a mitochondrial mode of action. Thus, the 2-alkoxy compounds were prepared to directly interrogate the necessity of the amino attachment for seizure suppression. The compounds were synthesized by reacting 2-hydroxy-1,4-naphthoquinone with tosylated commercial alcohols in DMF stirred over solid $K_2CO_3$, which renders the compound nucleophilic. The dark red reaction mixtures were heated at 60° C. for 2-4 hr, at which point TLC indicated complete consumption of the tosylate reactant. The reaction mixture remains deep red due to the presence of a deprotonated side product, which forms by C-substitution as opposed to the desired O-alkylation. Extraction with basic aqueous solution following dilution of the reaction mixture into dichloromethane removes most of the side product. The target 2-alkoxy compounds are then purified by reversed-phase chromatography and isolated as off-white to pale yellow solids, generally in low (10-30%) yield.

ii. In Vitro Screening for Neuroprotection.

The HT22 murine hippocampal cell system was chosen as an initial phenotypic screen for neuroprotective efficacy (Andreux et al., 2013; Andreux et al., 2014; Ohlow et al., 2017; Schubert and Maher, 2012). HT22 cells exposed to high extracellular Glu (>5 µM) undergo oxytosis, a non-apoptotic programmed cell death involving glutathione (GSH) depletion followed by ROS accumulation, oxidative damage, and a cytotoxic signaling cascade (Tan et al., 2001). Glu blocks the -xC cystine antiporter, causing (Tan et al., 2001) cells to accumulate severe oxidative stress, mitochondrial depolarization, disrupted mitochondrial morphology, and $Ca^{2+}$ influx (Tan et al., 2001; Yang et al., 2011; Cheng et al., 2013—cellular events that may occur in neurological diseases, including epilepsy. Thus, the immortalized HT22 cell line is a well-established model of neuronal oxidative stress (Sagara and Schubert, 1998; Matsumoto et al., 1996; Albrecht et al., 2010; Ha and Park, 2006; van Leyen et al., 2005; Tobaben et al., 2011), and a verified model of neurodegeneration to screen for potential neuroprotective drugs (Albrecht et al., 2010; van Leyen et al., 2008; Lewerenz et al., 2009; Lewerenz et al., 2003).

The substituted naphthoquinones were previously shown to protect HT22 from oxytosis by restoring or protecting mitochondrial function, mitochondrial morphology, and dampening production of ROS via mechanisms that do not involve GSH restoration or upregulation of oxidant clearance enzymes (Josey et al., 2013). Consistent with that work, most of the 2-amino compounds achieved protection of HT22 cells against glutamate-induced oxytosis in the nM to µM range. Cells exposed to 10 mM Glu were treated compounds from 0.1 nM to 10 µM to detect EC50s in the 10-1000 nM range, in order to rapidly identify compounds with neuroprotective potency equal to or greater than compounds screened previously. Neuroprotection based on relative cell viability compared to +Glu and –Glu control cells was measured.

Figure 4:
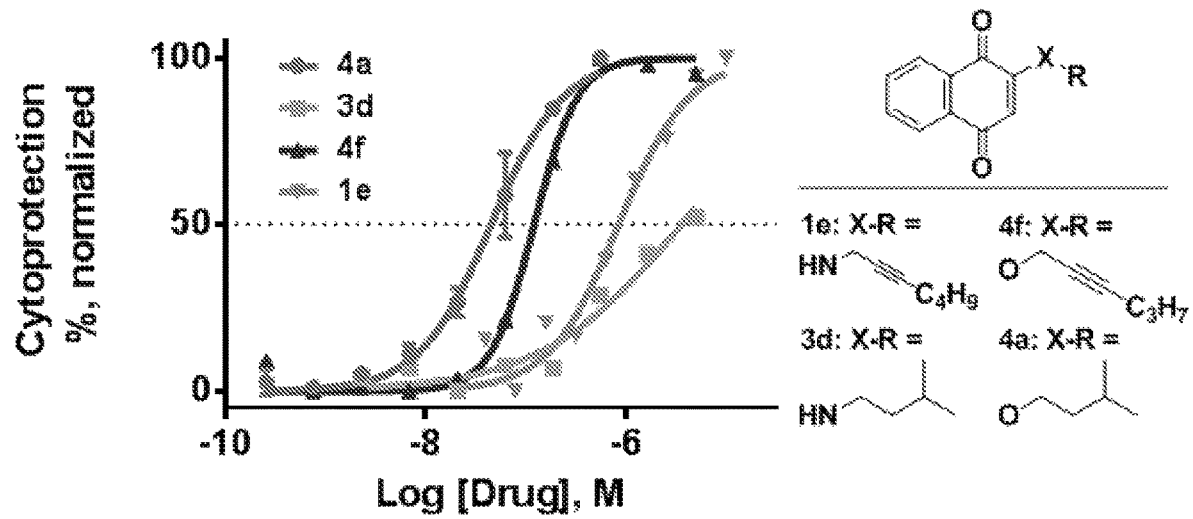
FIG. 4: Dose-response curves for selected compounds, demonstrating their ability to protect HT22 cells from Glu-induced oxytocic cell death. Cytoprotection data are expressed as percentage of viable Glu- and drug-treated cells as determined by relative resorufin fluorescence data normalized to fluorescence measured for untreated cells (100% viability) and Glu-treated cells unexposed to drug compounds (0% viability). Curves were fitted from 8-10 point titrations (n=2-4) with data points showing mean cytoprotection %±SEM.

FIG. 4 shows dose-response curves for representative compounds of the four structural groups studied. Among the 2-amino compounds (1-24), the most potent had aromatic alkyne capping groups (8-11, $EC_{50}$s: 100-300 nM). Trifluoromethyl substitution in 12 and 13 slightly dampened potency ($EC_{50}$s: ~500 nM), and substitution with the polar sulfonamide group in 14 substantially decreased efficacy ($EC_{50}$: ~2 µM). Less protective were structurally similar analogs with alkyl-chain groups (2-6, $EC_{50}$s: ≥~1 µM). Data for 7 (see in vivo toxicity, below), with an amine-containing capping group, was poorly reproducible and showed poor protection. Compounds with lengthened chains between nitrogen and alkyne (15,16,18,20,21) and/or branching of that chain (18-21) were also less potent, with $EC_{50}$s typically >2 µM. The most potent of the branched compounds, 19 (~1.5 µM), retained the single carbon linker between nitrogen and triple bond, while the least protective, 21 (~6 µM), possessed a bulky phenyl branching group. The "MK-like" compounds 22 and 24, with an isoprenoid tail attached to the nitrogen, were not as potent ($EC_{50}$s: ~9.2 and 2.7 µM, respectively), though the bromine-containing 23 showed a potent $EC_{50}$ of 133 nM, albeit with poorly shaped titration data.

The alkoxy compounds 25-31 showed markedly improved potency compared to all but the most potent amino compounds. $EC_{50}$s for the alkoxy compounds ranged from ~300 nM (29) to ~24 nM (25). Though fewer alkoxy than amino compounds were prepared and screened, the data does not seem to indicate large effects on neuroprotection based on the nature of the O-capping group. To support the hypothesis that the replacement of N with O was the primary factor leading to improved neuroprotection, compound 17 was prepared: an amine-substituted naphthoquinone with the same isoamyl substituent as 25. This amine analog of 25 displayed poor HT22 data but indicating an $EC_{50}$ at least >12 µM.

iii. In Vivo Toxicology in Zebrafish.

Prior to anti-seizure activity screening, compounds were tested for toxicity in the animal model. Zebrafish, like rodents, possess homologs for ~82-84% of genes associated with human disease (Howe et al., 2013; Schriml et al., 2003), and are good models for comparative mitochondrial toxicology (Broughton et al., 2001; Artuso et al., 2012). Good concordance between mammalian and zebrafish models has been verified for many developed drugs (Nadanaciva et al., 2013). The route of drug exposure (absorption from media) precludes direct correlations between zebrafish toxicology and patient ADME profiles; nevertheless, zebrafish toxicity provides a convenient first-pass characterization of the safety threshold for each compound.

Zebrafish larvae, 7 days post-fertilization (dpf), were exposed to compounds at 20, 15, 10, and 5 µM, six larvae per compound. Animals were observed 1, 5, and 24 hr after dosing for overt toxicity (altered survival, morbidity, morphological deformity). Heart rate, behavior, and startle response were monitored at each time point. If substantial toxicity was observed at these concentrations, compounds were subsequently tested at 1 and 0.1 µM. Alkyl-capped propargylamino compounds (2-5), and uncapped 1, showed little-to-no toxicity at 5 hr of treatment for all concentrations tested. For some of these compounds (2, 5), lethal toxicity was observed at 24 hr, particularly at higher concentrations (15-20 µM) and roughly correlated with length of the alkyl chain substituent: the shorter the chain, the more toxic. At 24 hr, 1 was lethal to all fish at 20 µM, but not at lower concentrations; 2 was lethal to all fish at 10 µM or above, and to ⅚ fish at 5 µM; 3 was lethal above 5 µM, while 4 was only lethal to ⅙ fish at 10 µM after 24 hr. Compound 5, with the longest (butyl) alkyl substituent only displayed toxicity when dosed at 20 µM, and no toxicity at shorter exposure times. Phenyl-capped congeners displayed little toxicity. 8 was not lethal at any concentration; 9, 10, 12, and 13 induced only modest morbidity (e.g., a single fish lying on its side) even at high concentrations. Analogs with additional nitrogen-containing groups were exceptions: 11, with a pyridyl-capped alkyne, induced convulsive swim behavior even at short exposure times (1-5 hr), and 14, with a sulfonamide group off the phenyl ring was lethal at 10 µM to all fish after 5 hr. 7, with and additional amino group, was lethal at most concentrations. These three compounds were not studied further.

Longer-chain and branched-chained amino compounds exhibited more prominent toxic effects, some even in spite of modest structural differences compared to other, non-toxic compounds tested. 15 and 16, which differ from 2 and 3 only by a second carbon between the nitrogen and alkyne, were acutely lethal to most fish at the lowest concentration after 1 hr. Exposure to 16 was reduced to 0.1 µM to alleviate the toxicity observed at 24 hr. As a result, synthesis of additional structural derivatives of this type was abandoned.

The branched compound 19 was toxic after 5 hr at 10 μM (⅙ fish dead) or higher. 22, with the MK-like isoprenoid tail attached to the nitrogen, displayed sedative effects at low concentrations and short time periods. However 23, with a 3-bromo substituent, showed little toxicity.

The alkoxy-substituted naphthoquinone, 25, was representative of the alkoxy class of compounds. No acute toxicity at high concentrations was observed and modest toxicity (⅔ survival) at 24 hr at the highest concentrations. No overt toxicity was observed at 10 μM or lower at any exposure time. While some in vitro HT-22 cytotoxicity was observed for compounds 25-31 at concentrations >10 μM, in vivo toxicity in these toxicological studies was not detected, or in subsequent zebrafish anti-seizure experiments.

iv. In Vivo Efficacy Studies in a Zebrafish Seizure Model

The zebrafish PTZ-induced seizure model was used to determine the most promising compounds' in vivo efficacy. Zebrafish larvae (7 dpf) were treated with the compound for 1 hr prior to inducing seizures with PTZ. As established by previous larval zebrafish anti-seizure studies (Rahn et al., 2014; Hansen et al., 2004; Baraban et al., 2005), total distance traveled by each fish after seizure induction was measured and used as a proxy for seizure activity. Following collection of locomotor data, observation of a startle response and visual inspection for abnormal morphology confirmed that alterations in swim activity were not caused by compound toxicity. Both 20 and 17 displayed sedative effects, so those compounds (along with 7, 11, 14-16; see above) were excluded from the screening.

Table 1 summarizes the effective doses of each compound for decreasing PTZ-induced seizure activity. The most effective compounds significantly decreased PTZ-induced seizure-like locomotor activity at low doses (5 or 2.5 μM) to distances statistically indistinguishable from control (fish in untreated tank water). For 1, the lead at the outset of this study, a minimum active dose of 20 μM was identified with a significant (p=0.0053) 50% decline in locomotor activity, which was greater than untreated control (p=0.0004). Therefore, a minimum active dose of 10 μM was elected as the 'go' criterion for identifying superior compounds in terms of efficacy in reducing seizures.

Figure 5:
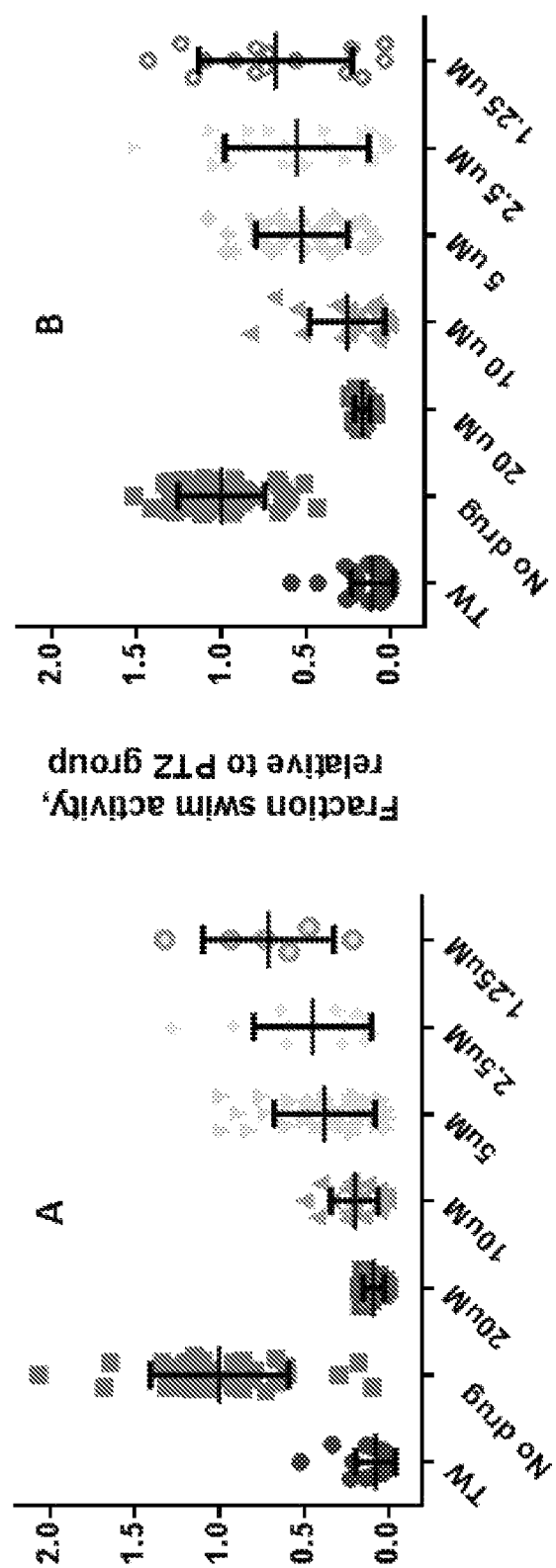
FIGS. 5A-B: Compounds 3 (FIG. 5A) and 25 (FIG. 5B) decrease seizures in a zebrafish model of epilepsy in a dose-dependent manner, and have better efficacy than our previous lead, 1. Zebrafish at 7 dpf were treated with 1.25-20 µM of 3 or 25 with pentylenetetrazole (PTZ, a convulsant agent). Seizure activity is expressed as a fraction of monitored fish swim distance relative to mean swim distance of fish treated with 10 mM PTZ alone. Data points represent individual zebrafish; bars shown mean±SD for each treatment group. P values at the top of each graph show statistical significance for comparison of treatment groups to PTZ-only group as determined by Kruskal-Wallis nonparametric ANOVA with Dunn's post-hoc correction for multiple comparisons; p values over horizontal bars are for comparisons of treatment groups to zebrafish untreated with PTZ or drug (**: p<0.0001; *: p<0.001; **: p<0.01).

Most of the branched or longer-chain amino compounds (18-20) were ineffective up to at least 10 μM. Compound 22 displayed activity at 20 and 40 μM that resulted from sedation, based on decreased startle response; 23 and 24, also with isoprenoid chains, were ineffective. Interestingly, 21, with a phenyl branch alpha to the nitrogen atom, was effective at 5 (p=0.0109), reducing PTZ-induced locomotor activity to that of control (ns difference, p>0.99). Among 2-14 (Group 1 compounds), the structure of the alkyne capping group affected anti-seizure activity. None of the phenyl-capped compounds tested (8-10, 12, 13) showed significant activity at 10 μM. Several compounds were tested at higher doses, to no effect: 10 was ineffective at 20 μM, 8 and 9 up to 40 μM. In contrast, a number of compounds with alkyl capping groups showed significant anti-seizure activity. Compound 2 reduced swim activity (p=0.0026) 89% at 40 μM to levels indistinguishable from untreated fish, but was not effective at 20 μM or lower. Compound 4 decreased PTZ-induced locomotor activity ~80% at 20 and 10 μM, but without statistical significance (p=0.0678 and 0.0847, respectively). Compound 6 showed significant activity at 10 μM (p=0.0060), reducing swim distance 85% (ns compared to control, p=0.9499); at 5 μM, seizure locomotion was reduced ~65%, though this activity was not significant compared to PTZ-treatment only (p=0.2381). Of this set of compounds, 3 and 5—with ethyl and butyl capping groups, respectively—demonstrated convincing anti-seizure activity. 5 completely attenuated PTZ-induced locomotor activity (ns compared to control, p>0.9999 at 10 μM, p=0.1901 at 5 μM) at doses as low as 5 μM. The reduction in swim activity was 84% at 5 μM (p<0.0001) and 77% at 10 μM (p=0.0069). Treatment with compound 3 also induced significant locomotor reduction across a range of doses: 20 μM (91% reduction, p<0.0001), 10 μM (80% reduction, p<0.0001), and 5 μM (62% reduction, p=0.0002). FIG. 5a depicts the apparent dose-response behavior of induced seizure activity to treatment with 3.

Several of the alkoxy-substituted naphthoquinones were tested (25, 29-31) as well. Compound 29 elicited significant reductions in PTZ-induced swim distances at 10 μM (53%, p=0.0226) and 5 μM (60%, p=0.0016; ns compared to control). 30 had significant efficacy at 10 μM (p=0.0010; 68% reduction, ns compared to control) and at 5 μM (p=0.0064, 53% reduction, ns compared to control). The 5 μM treatment elicited a 53% reduction in locomotor activity (p=0.0891) compared to control (no PTZ treatment, 83% lower swim distance than PTZ-only treatment). At 10 μM, 31 reduced swim distance to control levels (ns, p>0.9999) with a highly significant (p<0.0001) difference compared to PTZ treatment only; treatment effects at 5 μM were not significant (48% decrease in swim activity, p=0.1222). Treatment with 31 also led to higher-than-normal occurrences of toxic effects (either lack of survival or behavioral impairments) during PTZ-induced seizure experiments.

FIG. 5b displays anti-seizure data for compound 25, which proved to be the most effective compound tested: significant reduction (45%, p=0.0038) of locomotor activity at a dose of 2.5 μM, though not reduced to control (p=0.0005). The high activity and good apparent dose-response behavior of this compound led us to select 25, along with 3, for PK studies.

v. In Vivo Pharmacokinetic Studies in Mice

PK studies on 3 and 25 were carried out in CD-1 mice. Three males were dosed via oral gavage needle for oral administration at 20 mg/kg (10 mL/kg) or via intravenous administration at 5 mg/kg (10 mL/kg). Blood samples were taken at time intervals between 5 min and 24 hr from each animal. Animals treated with either compound displayed no abnormal clinical symptoms during the IV study. For 25, plasma concentrations declined in a multiphasic manner after IV administration at 5 mg/kg with a mean initial concentration ($C_0$) of 1,603 ng/mL. The compound displayed a high systemic clearance (CLp) of 68.8 mL/min/kg and a high steady-state volume of distribution ($V_{ss}$) of 13.2 L/kg, suggesting an extensive tissue distribution. The total systemic exposure ($AUC_{inf}$) was low at 1,211 h*ng/mL with a moderate terminal half-life ($t_{1/2}$) of 4.31 h. For 3, $C_0$ was 1,523 ng/mL. The compound displayed a high CLp of 188 mL/min/kg and a high Vss of 48.6 L/kg, also suggestive of extensive tissue distribution. A low $AUC_{inf}$ of 448 h*ng/mL was determined, with a long $t_{1/2}$ of 14.7 hr.

Initial PO experiments encountered difficulties. A formulation of 20% DMA—40% PEG300-40% $H_2O$ for the 20 mg/kg dosing led to labored breathing and significantly reduced activity in all animals within 30 min; all mice died between the 8 and 24 hr time points. 25 rapidly reached a high $C_{max}$ of 2,083 ng/mL within 30 min. Plasma concentrations then declined with a moderate $t_{1/2}$ of 5.56 hr. $AUC_{inf}$ was high at 11,521 hr*ng/mL with a high oral bioavailability (F) of greater than 100%, suggesting some saturation of clearance mechanisms. 3 reached a $C_{max}$ of 394 ng/mL within 15 min. Plasma concentrations then declined with a moderate $t_{1/2}$ of 5.27 hr. A modest $AUC_{inf}$ (992 h*ng/mL)

and good oral bioavailability (F, 55.3%) were determined. PO PK experiments were repeated for 25, with oral dosing at 20 mg/kg and 10 mL/kg of a suspension with 1% Tween 80:1% carboxymethylcellulose in water. No abnormal clinical symptoms were observed following administration of this formulation. The test compound rapidly reached a moderate $C_{max}$ of 282 ng/mL within 1 hr. After that, its plasma concentrations declined with a moderate $t_{1/2}$ of 3.49 hr. $AUC_{inf}$ was moderate at 1,953 hr*ng/mL, with a good oral bioavailability (F) of 40.3%.

B. Discussion

There is a critical unmet clinical need for new AEDs for patients with medication-resistant epilepsy. Prior work identified compound 1 as a potential AED based on anti-seizure activity in three vertebrate animal seizure models. These previous studies demonstrated that the 2-propargylamino-substituted 1,4-naphthoquinone was a promising scaffold for an AED. However, anti-seizure effects rapidly diminished within 1 hr in mouse seizure models. It is hypothesized that the short half-life ($t_{1/2}$=0.35 hr, 20 mg/kg i.p. injection) of 1 could at least partly explain the drop-off in protection over time.

In this study, the PK parameters were optimized and efficacy of the prior lead by synthesizing a series of 2-substituted naphthoquinone derivatives with capped amino or alkoxy substituents. These compounds were screened for in vitro neuroprotection and for in vivo mitigation of PTZ-induced seizure activity in zebrafish. Two compounds, with in vivo micromolar efficacy were selected and dose responsiveness in zebrafish for PK studies in mice. Capping the terminal alkyne of 1 with an alkyl or aryl group was intended to halt rapid in vivo drug oxidation and excretion. Additional variations in structure led to compounds with altered chain lengths between nitrogen and alkyne, variable group sizes and functional groups present in the alkyne-capping moiety, branching at the amino alpha carbon, and introduction of alternate unsaturated groups in place of alkyne (FIG. 2). These compounds provided a range of drug-like properties (e.g., lipophilicity, molecular shape, and structural rigidity) for optimization. Derivatives with the amine group replaced with an ether group were also synthesized, based on the hypothesis that altering the redox properties of the naphthoquinone pharmacophore would in turn affect activity. Earlier studies, which identified aminonaphthoquinones as promising neuroprotectants in HT22 cells, indicated that 2-hydroxynaphthoquinone as a much less potent compound for protecting neurons from oxytosis (Josey et al., 2013). However, unlike the amino compounds, 2-hydroxynaphthoquinone has a low pKa and likely exists in its deprotonated, anionic state to a significant extent in vitro and in vivo (Petrova et al., 1990). Deprotonation substantially alters its reduction potential and drug-like properties. Capping the oxygen with an alkyl substituent prevents deprotonation, potential tautomerization to toxic 1,2-naphthoquinone, and opens synthetic space for tuning drug-like properties. Thus, it was investigated if naphthoquinone redox potential, modulated by N- vs. O-substitution, has an effect on anti-seizure activity and neuroprotection, as might be expected for a drug with a mitochondrial modulation mode of action (Ohlow et al., 2017; Vafai et al., 2016; Wen et al., 2011; Poteet et al., 2012).

Although several of the compounds tested in this study have been reported previously (Fei et al., 2011; Fei et al., 2010; Google Patents, assignee. Synthesis method of azepine anthraquinone 2010; Jiang et al., 2010; Jiang and Wang, 2009; Wang et al., 2014; Gornostaev et al., 2016; Novel tetracyclonaphthooxazole derivative and preparation method thereof, 2015; Adin and Fleming, 1980; Fieser, 1926; Wang et al., 2015; Kumar et al., 2017; Ogata et al., 2016; Lien et al., 2002), none has been studied as a potential AED to the inventor's knowledge. The majority of the targets are new compounds. While the yields of the reactions were modest, the short synthetic routes and ease of preparation lend themselves to scaled-up synthesis.

Among the amino compounds (1-24) screened In the HT22 oxytosis assay, propargylamino compounds (1-13) were more protective in general than the compounds with branching between nitrogen and alkyne (18-21) or even compounds with a chain between nitrogen and alkyne lengthened by a single carbon (15, 16). In particular, the compounds (8-13) with aryl substitution of the alkyne were more effective neuroprotectants in the HT22 assay than the other amino compounds. An exception was 14, with a highly polar sulfonamide moiety on the phenyl ring. The more "MK-like" compounds (22, 24) with isoprenoid groups did not show enhanced neuroprotective activity compared to other compounds tested; 22 was one of the least effective compounds screened (EC50: ~9 μM). The greater rigidity (i.e., fewer rotatable bonds) of aryl groups may enhance the drug-like properties of the compounds, or the aryl groups may allow for better interaction with an as-yet identified target in the cells. But with the $EC_{50}$s spanning little more than an order of magnitude with overlaps between structural classes, the in vitro data preclude drawing broad conclusions correlating subtle structural differences to neuroprotective efficacy. Several of the alkoxy compounds were more potent than any of the amino compounds tested, and all were roughly as protective as the most potent amino compounds. Without wishing to be bound by any theory, it is believed that the large change in redox potential that an O- vs. N-substituent imparts on the naphthoquinone ring, with the alkoxy compounds predicted to have a more positive potential including more capable of accepting electrons from cellular reducing agents or enzymes (Milton et al., 2015; Fieser and Fieser, 1935). The alkoxy compounds also lack the additional hydrogen bond donor provided by an NH (group, which may alter potency in the HT22 oxytosis system. However, in the previous study, capping the amine was found with a second, small substituent (e.g., methyl) and thereby removing that H-bond donor tended to show little effect on compounds' efficacy in this assay (Josey et al., 2013).

In the zebrafish PTZ-induced seizure model, several of the compounds that displayed neuroprotection in HT22 failed to protect against seizures. For example, the phenyl-capped compounds (8-13) displayed little anti-seizure activity. These results are consistent with the previous studies, which demonstrated that greater efficacy in the HT22 oxytosis assay does not necessarily correlate with efficacy in the zebrafish seizure model. Initial results indicated that 22, which most closely resembles the structure of MK4, potently reduced swim activity; however, on further investigation, this result originated from a general sedative effect rather than specific anti-seizure activity. The compounds proved to be compounds similar in structure to 1 but with short (2,3,5,6) alkyl capping groups on the alkyne, as well as several of the alkoxy compounds, particularly 25, with a five-carbon alkyl chain attached to the oxygen. Apart from the naphthoquinone core, 25 is structurally distinct from 1. Of these active compounds, 3, 5, 25, 29, and 3 displayed significant efficacy at doses as low as 5 μM. Interestingly, 21—with phenyl branching and an elongated chain—was also effective at 5 μM; no other compound in that structural class showed any anti-seizure activity. However, the uncapped alkyne moiety would be a liability in PK studies; thus, derivative of this compound will be a focus of future studies.

25 was the only compound to show significant anti-seizure activity at 2.5 µM. In the specific case of 25, the potent in vitro neuroprotectant proved to be an effective in vivo anti-seizure compound tested. Yet 3 had an in vitro neuroprotective efficacy several hundred times less than that of 25. The mechanisms of compound uptake from tank water may explain some difference between activity in zebrafish and in cells. Without wishing to be bound by any theory, some of this difference to compounds' blood-brain barrier (BBB) permeability in vivo, but certainty of the role of the zebrafish BBB in these studies cannot be determined at this time. While zebrafish may begin to develop a BBB with structural and functional similarities to that of higher-vertebrates at 3 dpf, the BBB may not be fully mature until 10 dpf or later (Watanabe et al., 2012; Xie et al., 2010; Jeong et al., 2008; Fleming et al., 2013). 7 dpf larvae were used in these experiments.

PK studies were carried out in mice treated both compounds 3 and 25 intravenously and per os. As hypothesized, these two compounds displayed dramatically improved PK properties compared to 1. IV-administered half-life increased from ~20 min for 1 to nearly 15 hr for 3 on capping the terminal alkyne with the ethyl group, data that clearly demonstrates the PK liability of 1's oxidizable terminal alkyne. Despite the toxicity effects observed for PO dosing in a high DMA cosolvent solution formulation, 25 in particular showed excellent oral systemic exposure ($C_{max}$=2,083 ng/mL, AUC=11,521 hr*ng/mL), sustained high oral concentrations (C=531 ng/mL at 8 hr post-dose), and good oral terminal half-life ($t_{1/2}$=5.6 hr), with acceptable systemic clearance ($C_L$=69 mL/min/kg) and volume of distribution ($V_{ss}$=13 L/kg), and high oral bioavailability (>100%, likely due to saturation of clearance mechanisms). Repeating the oral PK studies at 20 mg/kg in a suspension formulation led to reduced systemic exposure and therefore oral bioavailability, as expected: $C_{max}$ and AUC were significantly decreased (6-7 fold) and the oral bioavailability was 40%. It is likely that a suspension formulation would need to be used for a general toxicology study (GLP or non-GLP). In addition to the problems observed with a solution formulation for these compounds, much higher oral doses are required to reach the maximum tolerated dose in toxicology studies in mammals. The PK parameters observed for 25 when administered in a suspension are within acceptable ranges for druggable compounds, depending upon the potency of the molecule. Thus, the efficacy of 25 is still being tested as an orally administered drug in multiple rodent epilepsy models. Further, full metabolic stability studies, aqueous solubility studies, P450 inhibition experiments, and determining plasma protein binding in mouse and human plasma are being carried out. Studies to determine brain permeation of these compounds in mice are also being carried out.

TABLE 1

Substituted 1,4-naphthoquinones included in this study

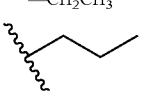

Compounds 1-14

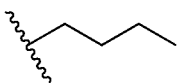 [SMILES: *CCCC]

Compounds 15-24

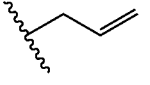 [SMILES: *CC=C]

Compounds 25-32

| Compound | R | Neuroprotection[a] $EC_{50}$ (nM) | Anti-seizure[b] activity |
|---|---|---|---|
| 1 | —H | 694[c] | 20 µM (50%)** |
| 2 | —CH₃ | 1219 (1062-1398) | 40 µM (89%)**, + |
| 3 | —CH₂CH₃ | 1011 (911-1123) | 5 µM (62%)*** |
| 4 | 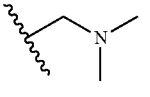 [SMILES: *CN(C)C] | 989 (878-1115) | >20 µM |
| 5 | (n-butyl) | 1569 (1461-1684) | 5 µM (84%)***, + |
| 6 | (allyl-like) | 2640 (2318-3007) | 10 µM (85%)**, + |
| 7 | (CH₂N(CH₃)₂) | N/A[d] | N/A[e] |

TABLE 1-continued

Substituted 1,4-naphthoquinones included in this study

Compounds 1-14 | Compounds 15-24 | Compounds 25-32

| Compound | R | Neuroprotection[a] EC$_{50}$ (nM) | Anti-seizure[b] activity |
|---|---|---|---|
| 8 | phenyl | 162 (130-202) | >40 μM |
| 9 | 3-fluorophenyl | 216 (175-267) | >40 μM |
| 10 | 3-methoxyphenyl | 215 (187-246) | >20 μM |
| 11 | pyridin-3-yl | 290 (258-327) | N/A[e] |
| 12 | 4-(trifluoromethyl)phenyl | 566 (419-766) | >10 μM |
| 13 | 3-(trifluoromethyl)phenyl | 584 (511-667) | >10 μM |
| 14 | 3-(methylsulfonamido)phenyl | 1941 (1639-2300) | N/A[e] |
| 15 | but-2-yn-1-yl | 2911 (2589-3273) | N/A[e] |
| 16 | pent-2-yn-1-yl | 5603 (4952-6340) | N/A[e] |

TABLE 1-continued

Substituted 1,4-naphthoquinones included in this study

Compounds 1-14 / Compounds 15-24 / Compounds 25-32

| Compound | R | Neuroprotection[a] EC$_{50}$ (nM) | Anti-seizure[b] activity |
|---|---|---|---|
| 17 | (4-methylpentyl) | N/A[d] | 5 μM (76%)**, +, # |
| 18 | (2-(hydroxymethyl)pent-3-ynyl) | 2168 (1497-3140) | >10 μM |
| 19 | (but-3-yn-2-yl) | 2145 (1767-2605) | >10 μM |
| 20 | (pent-4-yn-2-yl) | 3691 (3283-4149) | >10 μM |
| 21 | (1-phenylbut-3-ynyl) | 6151 (5763-6565) | 5 μM (86%)*, + |
| 22 | geranyl, X = H | 9222 (9464-11240) | 20 μM (96%)*, +, # |
| 23 | geranyl, X = Br | 133 (106-166) | >10 μM |
| 24 | geranyl, X = CH$_3$ | 2738 (2301-3259) | >10 μM |

TABLE 1-continued

Substituted 1,4-naphthoquinones included in this study

Compounds 1-14 | Compounds 15-24 | Compounds 25-32

| Compound | R | Neuroprotection[a] EC$_{50}$ (nM) | Anti-seizure[b] activity |
|---|---|---|---|
| 25 | isobutyl (–CH$_2$CH(CH$_3$)$_2$) | 23.9 (17.1-32.2) | 2.5 μM (450)** |
| 26 | n-butyl | 78.0 (51.7-118) | N/A[e] |
| 27 | benzyl | 168 (151-188) | N/A[e] |
| 28 | –CH$_2$C≡CCH$_3$ | 168 (127-222) | N/A[e] |
| 29 | –CH$_2$C≡CCH$_2$CH$_3$ | 307 (144-651) | 5 μM (60%)**, + |
| 30 | –CH$_2$C≡CCH$_2$CH$_2$CH$_3$ | 249 (235-263) | 5 μM (53%)**, + |

TABLE 1-continued

Substituted 1,4-naphthoquinones included in this study

Compounds 1-14   Compounds 15-24   Compounds 25-32

| Compound | R | Neuroprotection[a] EC$_{50}$ (nM) | Anti-seizure[b] activity |
|---|---|---|---|
| 31 | (hex-2-yn-1-yl) | 76.1 (66.6-87.0) | 10 μM (89%)***, + |
| 32 | (3-phenylprop-2-yn-1-yl) | N/A[e] | N/A[e] |

[a]In vitro neuroprotection assessed by the HT22 oxytosis assay.
Cell viability was estimated by CellTiter Blue treatment with fluorescence measurements at 490 nm.
EC$_{50}$ (drug concentration protecting 50% of cells from death) values were calculated using GraphPad Prism log(dose)-response curve fitting, based on ≥8-point by the zebrafish PTZ-induced titrations, n ≥ 2.
95% CI in parentheses.
[b]Anti-seizure activity by the zebrafish PTZ-induced seizure model based on distance traveled (mm) as tracked by DanioVision.
Concentration given is the lowest tested dose at which the drug treatment group showed significant difference compared to normalized PTZ treatment-only groups.
In parentheses, the percent reduction in mean swim activity at that dose, compared to PTZ control fish (100% = reduction to tank water-only control swim distance).
The Kruskal-Wallis nonparametric test for one-way analysis of variance (ANOVA) followed by Dunn's Method for multiple comparisons was used to compare groups.
*p <0.05, p <0.01, *p <0.001.
+Treatment group statistically indistinguishable from untreated (no PTZ) control group, p >0.05.
Swim activity reduction likely non-specific result of sedative or other drug effect.
[c]Previously reported.
[d]Not tested.
[e]Results gave poor EC50 curve fits.

TABLE 2

| | PK Summary | | | | | |
|---|---|---|---|---|---|---|
| | 1 | | 3 | | 25 | |
| Parameter | Mean | Standard deviation | Mean | Standard deviation | Mean | Standard deviation |
| Intravenous Administration | | | | | | |
| $t_{1/2}$ (hr) | 0.349 | 0.128 | 14.7 | 3.78 | 4.31 | 0.46 |
| $C_0$ (ng/mL) | 2017 | 570 | 1523 | 254 | 1603 | 668 |
| $C_{last}$ (ng/mL) | | | 1.37 | 0.167 | 2.26 | 0.42 |
| $T_{last}$ (hr) | | | 24 | 0 | 24 | 0 |
| AUC$_{last}$ (hr*ng/mL) | 404 | 58.7 | 421 | 64.8 | 1197 | 16.9 |
| AUC$_{inf}$ (hr*ng/mL) | 404 | 58.2 | 448 | 69 | 1211 | 20.3 |
| MRT$_{inf}$ (hr) | 0.282 | 0.0382 | 4.28 | 1.14 | 3.2 | 0.03 |
| AUC$_{inf}$/D (hr*mg/mL) | | | 89.6 | 13.7 | 242 | 3.6 |
| CL (mL/min/kg) | 83.6 | 11.6 | 188 | 27.3 | 68.8 | 1.14 |
| $V_{ss}$ (L/kg) | 1.43 | 0.387 | 48.6 | 15.9 | 13.2 | 0.21 |
| Oral Administration | | | | | | |
| $T_{1/2}$ (hr) | | | 5.27 | 0.27 | 5.56 | 0.643 |
| $C_{max}$ (ng/mL) | | | 394 | 98.3 | 2083 | 362 |

TABLE 2-continued

PK Summary

| Parameter | 1 | | 3 | | 25 | |
|---|---|---|---|---|---|---|
| | Mean | Standard deviation | Mean | Standard deviation | Mean | Standard deviation |
| $T_{max}$ (hr) | | | 0.139 | 0.096 | 0.333 | 0.144 |
| $C_{last}$ (ng/mL) | | | 33.1 | 4.93 | 531 | 37.8 |
| $T_{last}$ (hr) | | | 8 | 0 | 8 | 0 |
| $AUC_{last}$ (hr*ng/mL) | | | 738 | 49 | 7360 | 294 |
| $AUC_{inf}$ (hr*ng/mL) | | | 992 | 59.4 | 11521 | 482 |
| $MRT_{inf}$ (hr) | | | 5.82 | 0.53 | 7.84 | 0.88 |
| $C_{max}/D$ (mg/mL) | | | 19.8 | 4.92 | 104 | 18.1 |
| $AUC_{inf}/D$ (hr*mg/mL) | | | 49.6 | 3 | 576 | 24.2 |
| F (%) | | | 55.3 | 3.31 | 238 | 9.96 |

Example 2

A. Methods i. General Chemistry

Unless otherwise noted, chemicals and solvents were acquired from commercial sources and used as received without further purification. Yields refer to chromatographically and spectroscopically ($^1$H NMR) homogeneous material, unless otherwise stated. Reactions were monitored by thin layer chromatography (TLC) carried out on precoated silica gel PE SIL G/UV plates (Whatman), using UV light to visualize spots. Flash silica gel chromatography was carried out using prepacked silica columns on a Teledyne Isco Combiflash 200 eluting with ethyl acetate:hexane and reverse phase chromatography was performed using prepacked. C18 columns and a Teledyne Isco Combiflash 200 eluting with water:acetonitrile. All target compounds were at least 95% pure, confirmed via UV detection ($\lambda$=254 nm) on a Thermo LCQ Fleet HPLC-MS using an Accucore RP-MS HPLC column, 2.6 μm particle size, 30 mm×4.6 mm. Mobile phase was a gradient of water:methanol, each solvent containing 0.1% formic acid (v/v). [Agilent 1100 HPLC instrument using an ODS HYPERSIL column (5 μm, 4.6 mm×250 mm) using a gradient of water/methanol with 0.1% formic acid added.] Mass spectral data were gathered using a Thermo LCQ Fleet mass spectrometer with electrospray ionization. $^1$H NMR and $^{13}$C NMR data were collected in deuterated solvent with a Bruker 400 MHz and referenced to residual protio solvent or solvent carbon, respectively. Chemical shifts are given in parts per million ($\delta$). NMR descriptions use the following abbreviations: s=singlet, d=doublet, t=triplet, q=quartet, m=multiplet, and br=broad peak. Coupling constants (J) reported in Hz. Chemical names that are followed by footnotes indicate that those compounds have been previously reported.

ii. Synthesis of 2-Amino-1,4-Naphthoquinone Derivatives: General Procedure

One equiv. of the appropriate amine as free base or ammonium chloride salt was added to a solution of 2-bromo-1,4-naphthoquinone (typically, 150 mg, 0.633 mmol) in absolute EtOH (20 mL) in the presence of 2.2 equiv. triethylamine (194 μL, 1.39 mmol), resulting in color changes from yellow to deep red to brown. The reaction was stirred at room temperature for time periods of three hours to overnight, with reaction completion determined by TLC monitoring based on the absence of starting bromonaphthoquinone. Volatiles were removed by rotary evaporation and the crude residue redissolved in 2-4 mL of solvent for purification on a Teledyne Isco Combiflash automated chromatography system using pre-packed C18 silica gel columns and eluting with a water:acetonitrile gradient, unless otherwise indicated. Fractions monitored at 254 nm UV were collected. Amine precursors were either commercially available free bases or ammonium chloride salts, or were prepared as ammonium chloride salts from commercially available alcohol precursors as described previously. Compound 1 had been prepared and purified as part of a prior study.

2-(But-2-yn-1-ylamino)naphthalene-1,4-dione (2)

(Fei et al., 2011; Fei et al., 2010; Google Patents, assignee. Synthesis method of azepine anthraquinone 2010; Jiang et al., 2010; Jiang and Wang, 2009) Yield: 91 mg (64%) of yellow powder. ESI-MS m/z: 226.17 [M+H]$^+$. $^1$H NMR (400 MHz, DMSO-d$_6$) $\delta$ 7.98 (dd, J=7.7, 1.3 Hz, 1H), 7.95 (dd, J=7.7, 1.3 Hz, 1H), 7.83 (td, J=7.5, 1.4 Hz, 1H), 7.79 (t, J=6.0 Hz, 1H), 7.74 (td, J=7.5, 1.4 Hz, 1H), 5.75 (s, 1H), 3.99 (dq, J=5.0, 2.4 Hz, 2H), 1.79 (t, J=2.4 Hz, 3H). $^{13}$C NMR (101 MHz, DMSO-d$_6$) $\delta$ 182.04, 181.94, 148.41, 135.32, 133.35, 132.81, 130.81, 126.36, 125.84, 101.47, 80.00, 74.62, 31.92, 3.53.

2-(Pent-2-yn-1-ylamino)naphthalene-1,4-dione (3)

Yield: 51.6 mg (34%) of yellow-orange powder. ESI-MS m/z: 240.10 [M+H]$^+$. $^1$H NMR (400 MHz, DMSO-d$_6$) $\delta$ 7.97 (dd, J=7.7, 1.3 Hz, 1H), 7.94 (dd, J=7.6, 1.3 Hz, 1H), 7.83 (td, J=7.5, 1.3 Hz, 1H), 7.78 (t, J=6.0 Hz, 1H), 7.73 (td, J=7.5, 1.4 Hz, 1H), 5.75 (s, 1H), 4.00 (dt, J=5.9, 2.2 Hz, 2H), 2.18 (qt, J=7.5, 2.2 Hz, 2H), 1.04 (t, J=7.5 Hz, 3H). $^{13}$C NMR (101 MHz, DMSO-d$_6$) $\delta$ 182.02, 181.94, 148.36, 135.30, 133.33, 132.79, 130.80, 126.34, 125.84, 101.52, 85.68, 74.78, 31.95, 14.18, 12.10.

2-(Hex-2-yn-1-ylamino)naphthalene-1,4-dione (4)

(Fei et al., 2011; Fei et al., 2010; Jiang et al., 2010) Yield: 28.8 mg (17.9%) of yellow powder. ESI-MS m/z: 254.19 [M+H]$^+$. $^1$H NMR (400 MHz, DMSO-d$_6$) $\delta$ 7.98 (dd, J=7.6, 1.3 Hz, 1H), 7.94 (dd, J=7.7, 1.3 Hz, 1H), 7.83 (td, J=7.6, 1.4 Hz, 1H), 7.79 (d, J=6.0 Hz, 1H), 7.74 (td, J=7.5, 1.4 Hz, 1H), 5.77 (s, 1H), 4.01 (dt, J=6.0, 2.2 Hz, 2H), 2.15 (tt, J=7.0, 2.2 Hz, 2H), 1.42 (h, J=7.2 Hz, 2H), 0.90 (t, J=7.4 Hz, 3H). $^{13}$C NMR (101 MHz, DMSO-d$_6$) $\delta$ 181.99, 181.97, 148.35, 135.32, 133.33, 132.80, 130.80, 126.36, 125.85, 101.61, 84.19, 75.58, 31.97, 31.16, 22.02, 20.32, 13.67.

2-(Hept-2-yn-1-ylamino)naphthalene-1,4-dione (5)

This synthesis was carried out on a 176 mg (0.743 mmol) scale. Yield: 120.4 mg (60.7%) of orange-yellow powder.

ESI-MS m/z: 268.25 [M+H]⁺. ¹H NMR (400 MHz, DMSO-d₆) δ 7.97 (dd, J=7.7, 1.3 Hz, 1H), 7.94 (dd, J=7.7, 1.3 Hz, 1H), 7.83 (td, J=7.6, 1.4 Hz, 1H), 7.78 (t, J=6.0 Hz, 1H), 7.73 (td, J=7.5, 1.4 Hz, 1H), 5.76 (s, 1H), 4.01 (dt, J=6.1, 2.2 Hz, 2H), 2.17 (tt, J=6.8, 2.2 Hz, 2H), 1.45-1.25 (m, 4H), 0.82 (t, J=7.2 Hz, 3H). ¹³C NMR (101 MHz, DMSO-d₆) δ 181.97, 148.33, 135.30, 133.33, 132.78, 130.79, 126.34, 125.84, 101.64, 84.31, 75.44, 31.98, 30.61, 21.73, 18.03, 13.84.

2-(Hex-5-en-2-yn-1-ylamino)naphthalene-1,4-dione (6)

Synthesis of this compound was carried out on a 0.545 mmol scale. Yield: 24 mg (17.6%) of yellow powder. ESI-MS m/z: 252.25 [M+H]⁺. ¹H NMR (400 MHz, DMSO-d₆) δ 7.98 (dd, J=7.6, 1.3 Hz, 1H), 7.95 (dd, J=7.6, 1.3 Hz, 1H), 7.88-7.81 (m, 2H), 7.74 (td, J=7.5, 1.4 Hz, 1H), 5.79 (ddd, J=22.0, 10.1, 5.1 Hz, 1H), 5.79 (s, 1H), 5.28 (dq, J=17.0, 1.9 Hz, 1H), 5.07 (dq, J=10.0, 1.8 Hz, 1H), 4.07 (dt, J=6.1, 2.2 Hz, 2H), 3.01 (dp, J=6.0, 2.0 Hz, 2H). ¹³C NMR (101 MHz, DMSO-d₆) δ 182.03, 181.95, 148.38, 135.34, 133.32, 133.24, 132.84, 130.81, 126.38, 125.85, 116.34, 101.62, 80.75, 78.05, 31.92, 31.16, 22.70.

2-((4-(Dimethylamino)but-2-yn-1-yl)amino)naphthalene-1,4-dione (7)

Yield: 62.2 mg (36.3%) of yellow powder. ESI-MS m/z: 269.17 [M+H]⁺. ¹H NMR (400 MHz, DMSO-d₆) δ 7.98 (dd, J=7.6, 1.3 Hz, 1H), 7.95 (dd, J=7.7, 1.3 Hz, 1H), 7.89-7.79 (m, 1H), 7.74 (td, J=7.5, 1.4 Hz, 1H), 5.80 (s, 1H), 4.09 (dt, J=6.2, 2.0 Hz, 2H), 3.21 (t, J=2.0 Hz, 1H), 2.13 (s, 6H). ¹³C NMR (101 MHz, DMSO-d₆) δ 182.00, 181.96, 148.28, 135.33, 133.29, 132.84, 130.80, 126.37, 125.86, 101.87, 80.14, 79.37, 47.60, 44.07, 31.83.

2-((3-Phenylprop-2-yn-1-yl)amino)naphthalene-1,4-dione (8)

(Fei et al., 2011; Fei et al., 2010; Jiang et al., 2010) This reaction was carried out on a 1.20 mmol scale. Yield: 72.4 mg (20.9%) of orange powder. ESI-MS m/z: 288.25 [M+H]⁺. ¹H NMR (400 MHz, DMSO-d₆) δ 8.00 (dd, J=7.7, 1.3 Hz, 1H), 7.95 (ddd, J=9.7, 6.8, 3.5 Hz, 2H), 7.84 (td, J=7.5, 1.4 Hz, 1H), 7.75 (td, J=7.5, 1.4 Hz, 1H), 7.47-7.31 (m, 5H), 5.89 (s, 1H), 4.31 (d, J=5.9 Hz, 2H). ¹³C NMR (101 MHz, DMSO-d₆) δ 182.16, 181.93, 148.44, 135.32, 133.32, 132.86, 131.87, 130.86, 129.19, 129.16, 126.39, 125.87, 122.39, 101.81, 85.28, 83.55, 32.40.

2-((3-(3-Fluorophenyl)prop-2-yn-1-yl)amino)naphthalene-1,4-dione (9)

This reaction was carried out on a 1.25 mmol scale. Yield: 94 mg (24.6%) of bright orange powder. ESI-MS m/z: 306.17 [M+H]⁺. ¹H NMR (400 MHz, DMSO-d₆) δ 7.98 (dd, J=7.6, 1.3 Hz, 1H), 7.96-7.90 (m, 2H), 7.83 (td, J=7.5, 1.3 Hz, 1H), 7.73 (td, J=7.5, 1.3 Hz, 1H), 7.44-7.35 (m, 1H), 7.30-7.18 (m, 3H), 5.88 (s, 1H), 4.32 (d, J=5.9 Hz, 2H). ¹³C NMR (101 MHz, DMSO-d₆) δ 182.18, 181.88, 162.23 (d, J=244.7 Hz), 148.39, 135.29, 133.29, 132.84, 131.28 (d, J=8.9 Hz), 130.83, 128.28 (d, J=2.9 Hz), 126.37, 125.86, 124.33 (d, J=9.6 Hz), 118.44 (d, J=22.8 Hz), 116.52 (d, J=21.1 Hz), 101.84, 86.50, 82.29 (d, J=3.3 Hz), 32.34.

2-((3-(3-Methoxyphenyl)prop-2-yn-1-yl)amino)naphthalene-1,4-dione (10)

Yield: 92.4 mg (46.2%) of bright orange powder. ESI-MS m/z: 318.25 [M+H]⁺. ¹H NMR (400 MHz, DMSO-d₆) δ 8.04-7.89 (m, 3H), 7.84 (td, J=7.5, 1.4 Hz, 1H), 7.75 (td, J=7.5, 1.3 Hz, 1H), 7.32-7.22 (m, 1H), 7.03-6.92 (m, 3H), 5.88 (s, 1H), 4.31 (d, J=6.0 Hz, 2H), 3.74 (s, 3H). ¹³C NMR (101 MHz, DMSO-d₆) δ 182.17, 181.92, 159.55, 148.43, 135.33, 133.31, 132.87, 130.85, 130.32, 126.39, 125.87, 124.26, 123.45, 116.65, 115.60, 101.80, 85.15, 83.48, 55.63, 32.38.

2-((3-(Pyridin-3-yl)prop-2-yn-1-yl)amino)naphthalene-1,4-dione (11)

Yield: 86 mg (46.9%) of yellow powder. ESI-MS m/z: 289.25 [M+H]⁺. ¹H NMR (400 MHz, DMSO-d₆) δ 8.65-8.59 (m, 1H), 8.55 (dd, J=4.9, 1.7 Hz, 1H), 8.03-7.89 (m, 3H), 7.88-7.79 (m, 2H), 7.74 (td, J=7.5, 1.3 Hz, 1H), 7.40 (ddd, J=8.0, 4.9, 0.9 Hz, 1H), 5.89 (s, 1H), 4.35 (d, J=5.9 Hz, 2H). ¹³C NMR (101 MHz, DMSO-d₆) δ 182.20, 181.89, 152.12, 149.48, 148.42, 139.16, 135.31, 133.30, 132.87, 130.85, 126.39, 125.87, 124.04, 119.48, 101.87, 88.66, 80.46, 32.41.

2-((3-(4-(Trifluoromethyl)phenyl)prop-2-yn-1-yl)amino)naphthalene-1,4-dione (12)

This synthesis was carried out on a 100 mg (0.422 mmol) scale. Yield: 19.8 mg (13.2%) of yellowish-brown powder. ESI-MS m/z: 356.17 [M+H]⁺. ¹H NMR (400 MHz, DMSO-d₆) δ 8.04-7.90 (m, 3H), 7.85 (td, J=7.5, 1.4 Hz, 1H), 7.80-7.70 (m, 3H), 7.64 (d, J=8.1 Hz, 2H), 5.90 (s, 1H), 4.36 (d, J=6.0 Hz, 2H). ¹³C NMR (101 MHz, DMSO-d₆) δ 182.21, 181.90, 148.44, 137.34-128.87 (m), 128.40-123.88 (m), 101.89, 88.28, 82.21, 32.39.

2-((3-(3-(Trifluoromethyl)phenyl)prop-2-yn-1-yl)amino)naphthalene-1,4-dione (13)

Yield: 63.3 mg (28.2%) of greenish-yellow powder. ESI-MS m/z: 356.17 [M+H]⁺. ¹H NMR (400 MHz, DMSO-d₆) δ 8.00 (dd, J=7.6, 1.3 Hz, 1H), 7.98-7.92 (m, 2H), 7.84 (td, J=7.5, 1.4 Hz, 1H), 7.78-7.70 (m, 4H), 7.65-7.57 (m, 1H), 5.89 (s, 1H), 4.34 (d, J=5.9 Hz, 2H). ¹³C NMR (101 MHz, DMSO-d₆) δ 182.21, 181.89, 148.43, 137.84-121.51 (m), 101.85, 87.25, 81.97, 32.36.

N-(3-(3-((1,4-dioxo-1,4-dihydronaphthalen-2-yl)amino)prop-1-yn-1-yl)phenyl)methanesulfonamide (14)

This synthesis was carried out on a 125 mg (0.527 mmol) scale. Yield: 39.3 mg (19.6%) of yellowish powder. ESI-MS m/z: 381.25 [M+H]⁺. 114 NMR (400 MHz, DMSO-d₆) δ 9.87 (s, 1H), 8.00 (dd, J=7.7, 1.3 Hz, 1H), 7.96 (dd, J=7.7, 1.3 Hz, 1H), 7.92 (t, J=6.0 Hz, 1H), 7.84 (td, J=7.5, 1.4 Hz, 1H), 7.75 (td, J=7.5, 1.4 Hz, 1H), 7.38-7.28 (m, 1H), 7.25-7.20 (m, 2H), 7.15 (dt, J=7.6, 1.3 Hz, 1H), 5.88 (s, 1H), 4.32 (d, J=6.0 Hz, 2H), 2.99 (s, 3H). ¹³C NMR (101 MHz, DMSO-d₆) δ 182.17, 181.91, 148.46, 139.17, 135.33, 133.32, 132.88, 130.87, 130.27, 127.20, 126.41, 125.87, 123.28, 122.36, 120.28, 101.79, 85.68, 83.04, 39.82, 32.36.

2-(Pent-3-yn-1-ylamino)naphthalene-1,4-dione (15)

This synthesis was carried out on a 281 mg (1.20 mmol) scale. Yield: 112 mg (39.1%) of yellow powder. ESI-MS m/z: 240.17 [M+H]$^+$. $^1$H NMR (400 MHz, DMSO-d$_6$) δ 7.98 (dd, J=7.6, 1.3 Hz, 1H), 7.94 (dd, J=7.6, 1.3 Hz, 1H), 7.83 (td, J=7.6, 1.3 Hz, 1H), 7.72 (td, J=7.5, 1.4 Hz, 1H), 7.50 (t, J=6.1 Hz, 1H), 5.72 (s, 1H), 3.30 (q, J=6.8 Hz, 2H), 2.45 (tq, J=7.3, 2.5 Hz, 2H), 1.74 (t, J=2.6 Hz, 3H). $^{13}$C NMR (101 MHz, DMSO-d$_6$) δ 181.92, 181.85, 148.66, 135.32, 133.49, 132.67, 130.77, 126.35, 125.79, 100.25, 77.72, 77.12, 41.64, 18.07, 3.63.

2-(Hex-3-yn-1-ylamino)naphthalene-1,4-dione (16)

This synthesis was carried out on a 303 mg (1.28 mmol) scale. Yield: 51.2 mg (24.0%) of yellow powder. ESI-MS m/z: 254.17 [M+H]$^+$. $^1$H NMR (400 MHz, DMSO-d$_6$) δ 7.98 (dd, J=7.6, 1.3 Hz, 1H), 7.94 (dd, J=7.7, 1.3 Hz, 1H), 7.83 (td, J=7.5, 1.4 Hz, 1H), 7.73 (td, J=7.5, 1.4 Hz, 1H), 7.50 (t, J=6.2 Hz, 1H), 5.74 (s, 1H), 3.30 (q, J=6.9 Hz, 2H), 2.46 (tt, J=7.1, 2.4 Hz, 2H), 2.12 (qt, J=7.8, 2.7 Hz, 2H), 1.02 (t, J=7.5 Hz, 3H). $^{13}$C NMR (101 MHz, DMSO-d$_6$) δ 181.95, 181.84, 148.71, 135.34, 133.50, 132.68, 130.77, 126.36, 125.79, 100.31, 83.58, 77.33, 41.59, 18.21, 14.44, 12.23.

2-(Isopentylamino)naphthalene-1,4-dione (17)

(Wang et al., 2014; Gornostaev et al., 2016; Novel tetracyclonaphthooxazole derivative and preparation method thereof, 2015) Yield: 26 mg (16.9%) of deep orange-red solid. ESI-MS m/z: 244.25 [M+H]$^+$. $^1$H NMR (400 MHz, DMSO-d$_6$) δ 7.97 (dd, J=7.7, 1.3 Hz, 1H), 7.94 (dd, J=7.7, 1.3 Hz, 1H), 7.82 (td, J=7.6, 1.4 Hz, 1H), 7.72 (td, J=7.5, 1.3 Hz, 1H), 7.56 (t, J=6.1 Hz, 1H), 5.65 (s, 1H), 3.18 (q, J=6.9 Hz, 2H), 1.63 (dp, J=13.2, 6.6 Hz, 1H), 1.47 (q, J=7.0 Hz, 2H), 0.91 (d, J=6.6 Hz, 6H). $^{13}$C NMR (101 MHz, DMSO-d$_6$) δ 182.03, 181.60, 148.90, 135.28, 133.67, 132.55, 130.85, 126.33, 125.77, 99.56, 40.66, 36.44, 25.97, 22.82.

Rac-2-((1-hydroxyhex-4-yn-2-yl)amino)naphthalene-1,4-dione (18)

This synthesis was carried out on a 200 mg (0.844 mmol) scale. Yield: 66.8 mg (29.4%) of orange powder. ESI-MS m/z: 270.25 [M+H]$^+$. $^1$H NMR (400 MHz, DMSO-d$_6$) δ 8.00 (dd, J=7.7, 1.3 Hz, 1H), 7.95 (dd, J=7.7, 1.3 Hz, 1H), 7.84 (td, J=7.5, 1.4 Hz, 1H), 7.74 (td, J=7.5, 1.4 Hz, 1H), 6.93 (d, J=8.0 Hz, 1H), 5.80 (s, 1H), 5.00 (t, J=5.5 Hz, 1H), 3.67-3.47 (m, 2H), 2.49-2.43 (m, 2H), 1.73 (t, J=2.5 Hz, 3H). $^{13}$C NMR (101 MHz, DMSO-d$_6$) 182.03, 181.94, 148.40, 135.43, 133.41, 132.77, 130.72, 126.43, 125.81, 100.71, 77.96, 76.41, 61.72, 53.82, 20.36, 3.64.

Rac-2-(but-3-yn-2-ylamino)naphthalene-1,4-dione (19)

This synthesis was carried out on a 200 mg (0.844 mmol) scale. Yield: 74.8 mg (39.4%) of yellow powder. ESI-MS m/z: 226.17 [M+H]$^+$. $^1$H NMR (400 MHz, DMSO-d$_6$) δ 7.99 (dd, J=7.8, 1.3 Hz, 1H), 7.94 (dd, J=7.6, 1.3 Hz, 1H), 7.84 (tt, J=7.6, 1.4 Hz, 1H), 7.74 (td, J=7.5, 1.4 Hz, 1H), 7.50 (d, J=7.3 Hz, 1H), 5.84 (d, J=0.6 Hz, 1H), 4.41 (pd, J=7.1, 2.2 Hz, 1H), 3.34 (d, J=2.2 Hz, 1H), 1.51 (d, J=6.9 Hz, 2H). $^{13}$C NMR (101 MHz, DMSO-d$_6$) δ 182.24, 181.87, 147.63, 135.31, 134.92, 134.03, 133.13, 132.91, 130.81, 126.53, 126.40, 125.96, 125.82, 110.63, 102.45, 99.98, 83.65, 74.27, 20.71, 14.31.

Rac-2-(pent-4-yn-2-ylamino)naphthalene-1,4-dione (20)

This synthesis was carried out on a 200 mg (0.844 mmol) scale. Yield: 26 mg (12.9%) of yellow powder. ESI-MS m/z: 240.25 [M+H]$^+$. $^1$H NMR (400 MHz, DMSO-d$_6$) δ 7.98 (dd, J=7.7, 1.3 Hz, 1H), 7.94 (dd, J=7.6, 1.3 Hz, 1H), 7.83 (td, J=7.5, 1.4 Hz, 1H), 7.72 (td, J=7.5, 1.4 Hz, 1H), 7.15 (d, J=8.9 Hz, 1H), 5.76 (d, J=0.7 Hz, 1H), 3.76 (dq, J=8.9, 6.4 Hz, 1H), 2.91 (t, J=2.7 Hz, 1H), 2.61-2.41 (m, 2H), 1.26 (d, J=6.4 Hz, 3H). $^{13}$C NMR (101 MHz, DMSO-d$_6$) δ 181.99, 181.96, 147.86, 135.35, 133.41, 132.70, 130.75, 126.38, 125.78, 100.57, 81.76, 73.44, 47.14, 24.73, 19.18.

Rac-2-((1-phenylbut-3-yn-1-yl)amino)naphthalene-1,4-dione (21)

Yield: 45 mg (23.6%) of brownish yellow powder. ESI-MS m/z: 302.25+Hr. $^1$H NMR (400 MHz, DMSO-d$_6$) δ 7.99 (dd, J=7.7, 1.3 Hz, 1H), 7.88 (dd, J=7.7, 1.4 Hz, 1H), 7.84 (d, J=7.9 Hz, 1H), 7.80 (td, J=7.5, 1.4 Hz, 1H), 7.72 (td, J=7.5, 1.4 Hz, 1H), 7.53-7.44 (m, 2H), 7.40-7.30 (m, 2H), 7.34-7.22 (m, 1H), 5.60 (s, 1H), 4.72 (td, J=8.0, 6.0 Hz, 1H), 2.99 (ddd, J=16.7, 8.1, 2.6 Hz, 1H), 2.94-2.90 (m, 1H), 2.78 (ddd, J=16.7, 6.0, 2.7 Hz, 1H), 2.08 (s, 1H). $^{13}$C NMR (101 MHz, DMSO-d$_6$) δ 182.02, 181.90, 147.98, 140.90, 135.34, 133.17, 132.83, 130.71, 128.91, 128.09, 127.24, 126.39, 125.79, 101.89, 81.63, 73.65, 55.56, 26.49, 1.64.

(E)-2-((3,7-Dimethylocta-2,6-dien-1-yl)amino)naphthalene-1,4-dione (22)

This synthesis was carried out on a 200 mg (0.844 mmol) scale. Yield: 78.1 mg (29.9%) of bright orange solid. ESI-MS m/z: 310.17 [M+H]$^+$. $^1$H NMR (400 MHz, DMSO-d$_6$) δ 7.97 (dd, J=7.7, 1.3 Hz, 1H), 7.93 (dd, J=7.7, 1.2 Hz, 1H), 7.82 (td, J=7.5, 1.4 Hz, 1H), 7.72 (td, J=7.5, 1.4 Hz, 1H), 7.65 (t, J=6.0 Hz, 1H), 5.57 (s, 1H), 5.19 (tq, J=6.3, 1.3 Hz, 1H), 5.04 (ddp, J=7.0, 5.7, 1.5 Hz, 1H), 3.80 (t, J=6.2 Hz, 2H), 2.14-1.93 (m, 4H), 1.70 (d, J=1.3 Hz, 3H), 1.58 (d, J=1.4 Hz, 3H), 1.54 (d, J=1.3 Hz, 3H). $^{13}$C NMR (101 MHz, DMSO-d$_6$) δ 182.08, 181.59, 148.75, 138.68, 135.27, 133.62, 132.58, 131.38, 130.82, 126.30, 125.79, 124.23, 120.09, 100.19, 40.47, 26.24, 25.88, 18.01, 16.65.

(E)-2-Bromo-3-((3,7-dimethylocta-2,6-dien-1-yl)amino)naphthalene-1,4-dione (23)

This compound was isolated as a byproduct during purification of 17 and purified by standard phase chromatography on a pre-packed silica gel column eluting with a hexanes:ethyl acetate gradient. Yield: 53.1 mg (16.3%) of deep red powder. ESI-MS m/z: 388.00 [M+H]$^+$. $^1$H NMR (400 MHz, DMSO-d$_6$) δ 8.05-7.93 (m, 2H), 7.82 (td, J=7.5, 1.5 Hz, 1H), 7.74 (td, J=7.5, 1.4 Hz, 1H), 7.44-7.35 (m, 1H), 5.36-5.25 (m, 1H), 5.08-4.97 (m, 1H), 4.36 (t, J=6.2 Hz, 2H), 2.14-1.92 (m, 4H), 1.68 (d, J=1.3 Hz, 3H), 1.56 (s, 3H), 1.52 (s, 3H). $^{13}$C NMR (101 MHz, DMSO-d$_6$) δ 180.33, 138.03, 135.27, 133.08, 131.32, 127.01, 126.49, 124.25, 122.45, 26.25, 25.86, 18.01, 16.74.

Synthesis of (E)-2-((3,7-Dimethylocta-2,6-dien-1-yl)amino)-3-methylnaphthalene-1,4-dione (24)

To 2-methyl-1,4-naphthoquinone (302 mg, 1.6 mmol) in methanol:dichloromethane (2 mL each) was added geranylamine (396 mg, 2.58 mmol) and the mixture was stirred at room temperature for 48 h. The solution was concentrated in vacuo and the reaction was purified on $C_{18}$ silica gel eluting with a water:acetonitrile gradient to yield 55 mg of a deep, red oil (11% yield). ESI-MS m/z: 324.17 [M+H]$^+$. $^1$H NMR (400 MHz, DMSO-d$_6$) δ 7.92 (ddd, J=7.5, 4.4, 1.3 Hz, 2H), 7.77 (td, J=7.5, 1.4 Hz, 1H), 7.68 (td, J=7.5, 1.3 Hz, 1H), 6.68 (t, J=6.6 Hz, 1H), 5.32-5.20 (m, 1H), 5.02 (tdd, J=6.8, 3.0, 1.5 Hz, 1H), 4.14 (t, J=6.4 Hz, 2H), 2.10 (s, 3H), 2.07-1.88 (m, 4H), 1.65 (s, 3H), 1.57 (s, 3H), 1.52 (s, 3H). $^{13}$C NMR (101 MHz, DMSO-d$_6$) δ 182.65, 182.14, 147.10, 137.47, 134.86, 133.21, 132.55, 131.33, 130.70, 126.03, 125.82, 124.25, 123.46, 111.43, 42.85, 39.25, 26.21, 25.86, 18.00, 16.62, 10.86.

iii. Synthesis of 2-Alkoxy-1,4-Naphthoquinones, General Procedure 2-hydroxy-1,4-naphthoquinone was dissolved in DMF in a round bottom flask charged with a stir bar. To this was added the appropriate tosylate reagent as a solution in DMF. With stirring, solid K2CO$_3$ was added to the flask; at this point, the color of the reaction mixture changed from pale yellow to deep red in color. The reaction was then refluxed under an argon atmosphere for 2 hr, at which time the reaction was cooled, poured into a separatory funnel with DI H$_2$O and DCM, and extracted. The organic layer was washed 2×20 mL with concentrated NaHCO$_3$, 2×15 mL brine, then dried over anhydrous MgSO$_4$. The solid drying agent was removed by gravity filtration and solvent removed by rotary evaporation to yield thick, red oil, which was then purified by reversed-phase chromatography.

2-(Isopentyloxy)naphthalene-1,4-dione (25)

(Adin and Fleming, 1980) This synthesis was carried out on a 160 mg (0.920 mmol) scale. Yield: 21.2 mg (9.4%) of off-white powder. ESI-MS m/z: 245.08 [M+H]$^+$. $^1$H NMR (400 MHz, DMSO-d$_6$) δ 8.04-7.93 (m, 2H), 7.91-7.75 (m, 2H), 6.38 (s, 1H), 4.08 (t, J=6.6 Hz, 2H), 1.78 (hept, J=13.2, 6.6 Hz, 1H), 1.67 (q, J=6.7 Hz, 2H), 0.94 (d, J=6.6 Hz, 6H). $^{13}$C NMR (101 MHz, DMSO-d$_6$) δ 184.98, 180.04, 160.11, 134.91, 134.01, 131.99, 131.31, 126.51, 125.96, 110.68, 68.32, 37.00, 25.07, 22.79.

Alternate Synthesis of 2-(Isopentyloxy)naphthalene-1,4-dione (25)

A modified procedure adapted from literature syntheses of 2-(methoxy)naphthalene-1,4-dione was also used to synthesize 25 in larger amounts (Ogata et al., 2016; Sreelatha et al., 2014). 2-hydroxy-1,4-naphthoquinone (348 mg, 2 mmol) was added to isoamyl alcohol (7 mL) and stirred. 0.3 mL of concentrated HCl was then added and the reaction mixture was refluxed for 4 hr. The deep red mixture was cooled to room temperature and then further in a refrigerator overnight. The solid precipitate was isolated by filtration, dissolved in DCM, and wash with K$_2$CO$_3$ (3×30 mL) to removed 3-substituted-2-hydroxy side products. The pooled aqueous layers were back extracted 2×30 mL with DCM, the organic layers pooled and washed with brine, then dried over MgSO$_4$. Following filtration and removal of solvent in vacuo, the dark, oily crude product was purified by reversed-phase chromatography using pre-packed C18 silica columns. Yield: 157 mg (32.1%) of tan solid with the same analytical data as above.

2-Butoxynaphthalene-1,4-dione (26)

(Fieser, 1926; Wang et al., 2015) This synthesis was carried out on a 169 mg (0.971 mmol) scale. Yield: 27 mg (12.1%) of yellow powder. ESI-MS m/z: 231.17 [M+H]$^+$. $^1$H NMR (400 MHz, DMSO-d$_6$) δ 7.99 (dd, J=6.9, 2.0 Hz, 1H), 7.97-7.93 (m, 1H), 7.89-7.79 (m, 2H), 6.34 (s, 1H), 4.04 (t, J=6.5 Hz, 2H), 1.75 (p, J=8.4, 6.5 Hz, 2H), 1.44 (h, 2H), 0.94 (t, J=7.4 Hz, 3H). $^{13}$C NMR (101 MHz, DMSO-d$_6$) δ 184.94, 180.03, 160.09, 134.90, 134.01, 131.96, 131.28, 126.51, 125.95, 110.61, 69.44, 30.35, 19.08, 14.04.

2-(Benzyloxy)naphthalene-1,4-dione (27)

(Kumar et al., 2017; Ogata et al., 2016) This synthesis was carried out on a 169 mg (0.971 mmol) scale. Yield: 32.6 mg (12.7%) of off-white powder. ESI-MS m/z: 265.17 [M+H]$^+$. $^1$H NMR (400 MHz, DMSO-d$_6$) δ 8.05-7.94 (m, 2H), 7.91-7.78 (m, 2H), 7.53-7.45 (m, 2H), 7.50-7.35 (m, 3H), 6.49 (s, 1H), 5.18 (s, 2H). $^{13}$C NMR (101 MHz, DMSO-d$_6$) δ 184.98, 180.01, 159.73, 135.45, 134.97, 134.12, 131.92, 131.30, 129.07, 128.96, 128.73, 126.57, 126.02, 111.28, 71.19.

2-(But-2-yn-1-yloxy)naphthalene-1,4-dione (28)

This synthesis was carried out on a 160 mg (0.920 mmol) scale. Yield: 39.3 mg (19.2%) of off-white powder. ESI-MS m/z: 223.08 [M+H]$^+$. $^1$H NMR (400 MHz, DMSO-d$_6$) δ 8.05-7.91 (m, 2H), 7.91-7.79 (m, 2H), 6.39 (s, 1H), 4.88 (q, J=2.4 Hz, 2H), 1.90 (t, J=2.4 Hz, 3H). $^{13}$C NMR (101 MHz, DMSO-d$_6$) δ 184.84, 179.80, 158.79, 135.00, 134.17, 131.84, 131.23, 126.58, 126.02, 111.51, 86.09, 73.11, 58.05, 3.66.

2-(Pent-2-yn-1-yloxy)naphthalene-1,4-dione (29)

This synthesis was carried out on a 169 mg (0.971 mmol) scale. Yield: 64 mg (27.5%) of off-white powder. ESI-MS m/z: 241.17 [M+H]$^+$. $^1$H NMR (400 MHz, DMSO-d$_6$) δ 8.05-7.91 (m, 2H), 7.92-7.79 (m, 2H), 6.39 (s, 1H), 4.89 (t, J=2.2 Hz, 2H), 2.28 (qt, J=7.5, 2.2 Hz, 2H), 1.09 (t, J=7.5 Hz, 3H). $^{13}$C NMR (101 MHz, DMSO-d$_6$) δ 184.84, 179.79, 158.78, 135.01, 134.18, 131.82, 131.23, 126.59, 126.02, 111.52, 91.46, 73.33, 58.07, 13.86, 12.19.

2-(Hex-2-yn-1-yloxy)naphthalene-1,4-dione (30)

This synthesis was carried out on a 160 mg (0.920 mmol) scale. Yield: 21.1 mg (9.0%) of off-white powder. ESI-MS m/z: 255.25 [M+H]$^+$. $^1$H NMR (400 MHz, DMSO-d$_6$) δ 8.03-7.99 (m, 1H), 7.99-7.95 (m, 1H), 7.91-7.80 (m, 2H), 6.40 (s, 1H), 4.91 (t, J=2.2 Hz, 2H), 2.26 (tt, J=7.0, 2.2 Hz, 2H), 1.48 (h, J=7.2 Hz, 2H), 0.93 (t, J=7.3 Hz, 3H). $^{13}$C NMR (101 MHz, DMSO-d$_6$) δ 184.82, 179.82, 158.75, 135.02, 134.19, 131.81, 131.23, 126.59, 126.03, 111.61, 90.05, 74.13, 58.05, 21.76, 20.38, 13.68.

2-(Hept-2-yn-1-yloxy)naphthalene-1,4-dione (31)

This synthesis was carried out on a 169 mg (0.971 mmol) scale. Yield: 15.9 mg (6.1%) of off-white powder. ESI-MS m/z: 269.25 [M+H]$^+$. $^1$H NMR (400 MHz, DMSO-d$_6$) δ 8.06-7.92 (m, 2H), 7.86 (pd, J=7.3, 1.7 Hz, 2H), 6.40 (s, 1H), 4.91 (t, J=2.2 Hz, 2H), 2.28 (tt, J=7.0, 2.2 Hz, 2H), 1.52-1.27 (m, 4H), 0.85 (t, J=7.2 Hz, 3H). $^{13}$C NMR (101 MHz, DMSO-d$_6$) δ 184.82, 179.84, 158.74, 135.03, 134.20, 131.82, 131.24, 126.60, 126.03, 111.65, 74.00, 58.05, 30.31, 21.74, 18.10, 13.83.

2-((3-Phenylprop-2-yn-1-yl)oxy)naphthalene-1,4-dione (32)

This synthesis was carried out on a 169 mg (0.971 mmol) scale. Yield: 92 mg (32.9%) of cream-colored solid. ESI-MS m/z: 289.24 [M+H]$^+$. $^1$H NMR (400 MHz, DMSO-$d_6$) δ 8.07-8.01 (m, 1H), 8.01-7.96 (m, 1H), 7.92-7.80 (m, 2H), 7.55-7.45 (m, 2H), 7.50-7.36 (m, 3H), 6.51 (s, 1H), 5.20 (s, 2H). $^{13}$C NMR (101 MHz, DMSO-$d_6$) δ 184.88, 179.77, 158.74, 135.02, 134.21, 132.07, 131.86, 131.28, 129.86, 129.28, 126.62, 126.06, 121.56, 111.69, 88.38, 83.20, 58.09.

B. Cell Culture

The HT22 neuronal cell line is a subclone of HT4, derived from the mouse hippocampus (Morimoto and Koshland, 1990). They do not express active ionotropic glutamate receptors and are not subject to excitotoxicity (Maher and Davis, 1996). The HT22 cells used in this study were kindly provided by Dr. David Schubert (The Salk Institute for Biological Studies, La Jolla, CA, USA). The cells were grown in Dulbecco's Modified Eagle's Medium (DMEM/high glucose) supplemented with 10% fetal bovine serum (Hyclone) and 5 mL of antibiotic-antimycotic (Amphotericin B, Penicillin, and Streptomycin; Invitrogen) at 37° C. in 5% $CO_2$.

C. Cell Viability Assay

HT-22 cells were seeded onto 96-well plates at 2.5×10$^3$ cells per well in 75 μL of medium and maintained at 37° C. in 5% $CO_2$ overnight prior to the initiation of experimental treatments. For glutamate toxicity testing, cells were subsequently treated with 25 μL of medium containing glutamate (monosodium glutamate, Sigma, 1 M stock concentration in media, to achieve a final concentration of 10 mM) plus compound (stock in DMSO) and maintained at 37° C. in 5% $CO_2$ for 24 hr. CellTiter-Blue® (resazurin cell viability assay reagent) was then added to each well at a final concentration of 0.125 mg/mL. The mixture was allowed to incubate for 2-4 hr until sufficient color change occurred. Cell viability was measured as a function of resorufin fluorescence intensity using a Tecan M200 Pro spectrophotometer, 560 nm/590 nm (excitation/emission). Cell viability was calculated as a percentage compared with untreated controls. EC50s were determined using GraphPad Prism's "log(inhibitor) vs. normalized response-Variable slope" function. Morphology of HT22 cells following treatments was determined by phase-contrast microscopy.

D. Zebrafish Breeding and Maintenance

Zebrafish (AB strain) were obtained from the Zebrafish International Resource Center (supported by P40 RR012546 from NIH—NCRR). Zebrafish were maintained and crossed according to standard methods (Westerfield, 2000). Fertilized eggs were collected and placed in E3 embryo medium and positioned in an incubator set at 28.5° C. with a 14/10-hr light/dark cycle (Kimmel et al., 1995). To determine the lethal dose of each compound, 96-well plates containing one zebrafish (7 days post-fertilization, dpf) per well in 100 μL of tank water were used. 100 μL of each compound (0.5-15 μM) was added to each well for 12 animals (one row) for a final volume of 200 μL. One row of larvae was used as dimethyl sulfoxide (DMSO)-only controls. The 96-well plate was placed on a warmer at 28.5° C. and fish were observed for changes in phenotype, behavior and mortality initially after addition of compound, after 1 hr treatment and after 5 hr treatment. All zebrafish studies were approved by the Medical University of South Carolina Institutional Animal Care and Use Committee (#180278) and performed in accordance with the guidelines.

E. Toxicity Studies in Zebrafish

Using a 96-well plate, 7 dpf zebrafish were placed one per well with 100 μL of tank water. 100 μL of each compound was then added to each well for 12 animals (one row) for a final volume of 200 μL. One row of zebrafish larvae was used as DMSO only controls. The 96-well plate was then placed on a warmer plate at 28.5° C. and the fish were observed for changes in phenotype, behavior and mortality initially after addition of compound, after 1 hr and 5 hr of treatment.

F. Induction and Monitoring of Seizures in Zebrafish

We induced seizures in 7 dpf zebrafish larvae by the addition of 15 mM PTZ as originally developed by Baraban et al., 2005. In a 48-well plate, one 7-dpf zebrafish was added per well. Larvae were dosed with each compound at a sub-lethal dose 1 hr prior to PTZ treatment. Two control rows were included with each experiment—tank water only control and PTZ only. Seizures were induced by adding PTZ to wells to yield a final concentration of 10 mM. After 5 min, the plate was transferred to the Daniovision instrument (Noldus Information Technology) and the chamber light was turned on. After 2 min, MediaRecorder (Noldus) was used to record video for 15 min. A small number of videos were acquired at 25 frames per second, but the majority of data were acquired at 60 frames per second. After recording, fish were monitored visually for survival, and agitation of the plates to elicit a startle response in zebrafish would determine whether reduced swim distances were accompanied by normal behavior and not the result of sedative effects. Ethovision XT software (Noldus) was used to track the fish movement from the video images in order to calculate the total distance traveled over 15 min. All experimental comparisons were made between animals from the same clutch.

G. Stability of Compound 1 in CD-1 Mouse Plasma

The plasma stability of 1 was determined by WuXi AppTec. Three samples were prepared using 3 μL working solution (2 μg/mL in acetonitrile:$H_2O$ 70:30) spiked in 57 μL CD-1 mouse plasma (EDTA-K2) and mixed well. Samples were stored at room temperature for two hours, mixed well, then precipitated. Three 0 hr samples were prepared in the exact same manner but were precipitated immediately upon preparation. Precipitate mixtures were centrifuged at 4000 rpm for 15 min, then 2 μL supernatant was used for LC-MS/MS analysis.

H. In Vivo Pharmacokinetics Procedure in Mice

The PK studies of 1 were performed by WuXi AppTec and PK studies of 3 and 25 were performed by Touchstone Biosciences (Peng et al., 2006b; Peng et al., 2001; Peng et al., 2006a; Peng et al., 2009). Male CD-1 mice were fed a standard laboratory rodent diet and housed in individual cages on a 12 hr light and 12 hr dark cycle with room temperature maintained at 22±3° C. and relative humidity at 50±20%. Animals were typically fasted overnight before dosing, with food returned after the 6 hr blood samples were obtained. Water was provided ad libitum throughout the study. The dosing solution of each test compound was prepared in a desired oral or intravenous formulation. Three to four animals were dosed via gavage needle for oral administration at 10-20 mg/kg (10-20 mL/kg) or via tail vein injection for IV administration at 2-5 mg/kg (2-5 mL/kg). All blood samples (30-200 μL per sample) were taken via appropriate vein (saphenous, jugular, or submandibular vein) at 5, 15, and 30 min and 1, 2, 4, 6, 8, and 24 hr after dosing. Fluid replacement (1.5 mL of 0.9% NaCl injection, USP) was administered subcutaneously once after the 2 hr blood sampling. Blood samples were collected in BD Microtainer tubes coated with anticoagulant, placed on ice, and within 30 min, centrifuged at 15,000 g for 5 min to obtain plasma samples. All plasma samples were stored at −70° C. until analysis.

I. Bioanalysis of Samples

Plasma samples were prepared as follows. Three volumes of acetonitrile containing internal standard was added to one volume of plasma to precipitate proteins. Samples were centrifuged (3000 g for 10 min) and supernatant removed for analysis by LC-MS/MS. Calibration standards and quality controls were made by preparation of a 1 mg/mL stock solution and subsequently a series of working solutions in methanol:water (1:1, v/v) which were spiked into blank plasma to yield a series of calibration standard samples in the range of 1.0 ng/mL to 10 μg/mL and quality control samples at three concentration levels (low, middle and high). All incurred PK/PD plasma samples were treated identically to the calibration standards and quality control samples. LC-MS-MS analysis was performed utilizing multiple reaction monitoring for detection of characteristic ions for each drug candidate, additional related analytes and internal standard.

J. PK Data Analysis

Plasma concentrations were measured as described above to determine a concentration vs. time profile. The area under the plasma concentration vs time curve (AUC) was calculated using the linear trapezoidal method. Fitting of the data to obtain pharmacokinetic parameters was carried out using non-compartmental analysis. Key PK parameters reported following intravenous administration are as follows: terminal half-life $t_{1/2}$, initial plasma concentration $C_0$, area under the plasma concentration vs. time curve AUC, volume of distribution at steady-state $V_{ss}$, total plasma clearance $C_{Lp}$, and mean residence time MRT. Key PK parameters reported following extravascular administration are as follows: terminal half-life $t_{1/2}$, maximum plasma concentration $C_{max}$, time to reach maximum plasma concentration $t_{max}$, area under the plasma concentration vs. time curve AUC, mean residence time MRT, and bioavailability F. All parameters are expressed for individual animals as well as mean, standard deviation, and coefficient of variation.

K. Statistical Analyses

Statistical analyses were performed with GraphPad Prism 6 software. For the in vitro HT22 oxytosis assay, dose-response data were fit using GraphPad Prism's log(inhibitor) vs normalized response-variable slope parameters to determine EC50 values and 95% confidence intervals. For the zebrafish locomotive anti-seizure activity data, multiple comparisons were made using a one-way analysis of variance (ANOVA) with a Kruskal-Wallis Test, followed by the Dunn's Method to determine significant differences between all pairs or between control and experimental groups using the Dunn Method for Joint Ranking. Differences were considered statistically significant when p<0.05. Data from zebrafish experiments are represented as scatter dot plots of individual measurements, with means±standard deviation indicated by bars.

The following compounds may be synthesized based on the synthetic schemes described above.

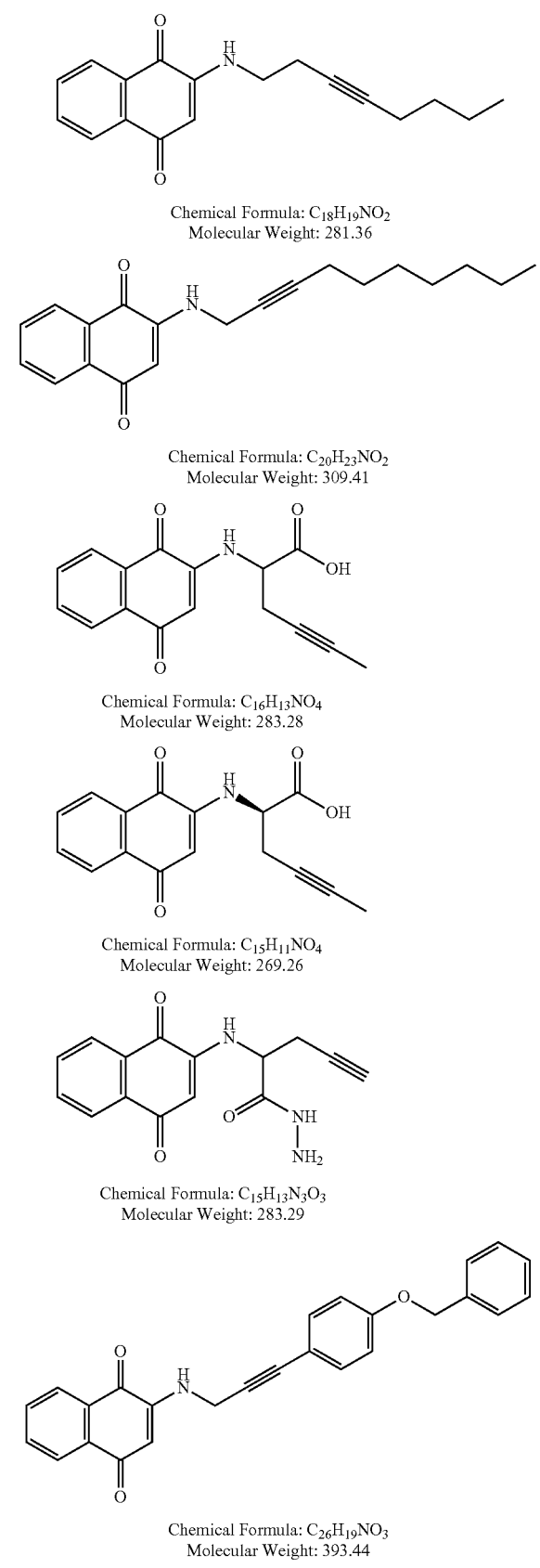

Example 3

Treatment of Medication-Resistant Epilepsy

From preliminary testing of four previous compounds of interest in the 6 Hz mouse seizure model, two compounds of particular interest, compound 3 (NT-181) and compound 17 (NT-102), displayed protection against seizures with few or no toxic events, as shown by Rotarod assay and behavioral observations. Synthesis for both compounds has been successfully scaled up. The pharmacokinetic (PK) parameters of these two Vitamin K analogs were determined via intravenous, intraperitoneal and oral administration in mice, and preliminary in vitro ADMET parameters were assessed (Table 3). These compounds are Ames-negative, have hepatic stability greater than 1 hour, can be formulated in oral solution and IV injection solution, can be synthesized in greater than 1 mg quantities, and have established brain PK. However, brain tissue binding was high for both compounds (97-98%). Both 3 (NT-181) and 17 (NT-102) have been tested for efficacy in the 6 Hz mouse seizure model at 22 mA and 32 mA, the corneal kindled mouse model, and the rat in vitro spontaneous electrographic bursting model of pharmacoresistance (Table 4). During the course of this testing, it was found that there were solubility issues with the formulation used (5% DMSO:95% Neobee); sacrifice of the animals revealed visible intraperitoneal deposits of the compound in the cavity around the injection site, and thus some of the compound may not be getting past this site. Higher concentrations may be required to complete the titration curves for protection in the 6 Hz mouse seizure model at 32 mA and 44 mA. Going through the records of the first time the Vitamin K analogs were tested in the 6 Hz model (2013-2014) revealed that the NINDS ETSP/University of Utah Anticonvulsant Drug Development (ADD) program had used a type of Miglyol for formulation. However, the type of Miglyol was not noted. Solubility of the Vitamin K analogs were tested with different types of Miglyol with varying viscosities and it was found that Miglyol840 (the least viscous Miglyol) was best. Preliminary studies with this new formulation reveal excellent solubility with full protection in the 6 Hz mouse seizure model at 22 mA, and quantification of both compounds (using this new formulation) in this model at 22 mA, 32 mA and 44 mA, is being performed as well as retesting in the corneal kindled model. Protection in acute and chronic seizure mouse models from the ADD workflow for pharmacoresistant epilepsy will be tested. Rat PK assessments will be performed, and seizure protection assessed in rat models in the ADD workflow such as the 6 Hz model and lamotrigine-resistant amygdala kindled mode. Results are shown below in Table 3 and Table 4.

TABLE 3

Mouse PK and in vitro ADMET summary

| | NT-181 | | NT-102 | |
|---|---|---|---|---|
| Parameter | Mean | Standard deviation | Mean | Standard deviation |
| Intravenous Administration (20% DMA: 40% PEG300: 40% $H_2O$) | 5 mg/kg | | 5 mg/kg | |
| $T_{1/2}$ (hr) | 14.7 | 3.78 | 4.47 | 0.536 |
| $C_0$ (ng/mL) | 1523 | 254 | 1907 | 84.7 |
| $C_{last}$ (ng/mL) | 1.37 | 0.167 | 0.154 | 0.0283 |
| $AUC_{last}$ (hr*ng/ml) | 421 | 64.8 | 636 | 49.3 |
| $AUC_{inf}$ (hr*ng/mL) | 448 | 69 | 637 | 49.1 |
| $MRT_{inf}$ (hr) | 4.28 | 1.14 | 0.874 | 0.0365 |
| $AUC_{inf}/D$ (hr*mg/mL) | 89.6 | 13.7 | 127 | 9.82 |
| $CL_p$ (ML/min/kg) | 188 | 27.3 | 131 | 10 |
| $V_{ss}$ (L/kg) | 48.6 | 15.9 | 6.89 | 0.512 |
| Brain Plasma Ratio | 0.373 | | 0.816 | |
| Intraperitoneal Admin. (5% DMSO: 95% neobee) | 20 mg/kg | | 20 mg/kg | |
| $T_{1/2}$ (hr) | 7.25 | 0.814 | 3.38 | 0.162 |
| $T_{max}$ (hr) | 1 | 0 | 1 | 0 |
| $C_{max}$ (ng/mL) | 147 | 33.5 | 320 | 91.1 |
| $C_{max}/D$ (kg/kL) | 7.33 | 1.67 | 16 | 4.56 |
| $t_{last}$ (hr) | 24 | 0 | 24 | 0 |
| $C_{last}$ (ng/ml) | 1.47 | 0.312 | 1.95 | 0.276 |
| $AUC_{last}$ (hr*ng/ml) | 463 | 28.6 | 1716 | 265 |
| $AUC_{inf}$ (hr*ng/mL) | 478 | 28 | 1726 | 265 |
| $AUC_{inf}/D$ (hr*mg/kL) | 23.9 | 1.4 | 86.3 | 13.2 |
| $MRT_{inf}$ (hr) | 4.2 | 0.696 | 4.39 | 0.49 |
| Oral Administration (5% DMSO: 95% Neobee) | 20 mg/kg | | 20 mg/kg | |
| $t_{1/2}$ (hr) | 3.34 | 0.183 | 5.28 | 0.552 |
| $t_{max}$ (hr) | 4.0 | 0 | 0.25 | 0 |
| $C_{max}$ (ng/mL) | 90.2 | 12.8 | 1025 | 273 |
| $C_{max}/D$ (kg/kL) | 4.51 | 0.639 | 51.2 | 13.7 |
| $t_{last}$ (hr) | 24 | 0 | 24 | 0 |
| $C_{last}$ (ng/mL) | 1.21 | 0.218 | 1.43 | 0.278 |
| $AUC_{last}$ (hr*ng/ml) | 682 | 135 | 903 | 175 |
| $AUC_{inf}$ (hr*kg/mL) | 688 | 135 | 914 | 177 |
| $AUC_{inf}/D$ (hr*kg/kL) | 34.4 | 6.76 | 45.7 | 8.83 |
| $MRT_{inf}$ (hr) | 5.71 | 0.29 | 2.50 | 0.228 |
| F (%) | 38.4 | 7.54 | 35.9 | 6.93 |
| In vitro ADMET | | | | |
| Brain tissue binding (% bound) | 97.4 | 0.486 | 98.5 | 0.168 |
| Aqueous solubility at pH 7.4 (ug/mL in 50 mM phosphate buffer) | 4.79 | | 9.64 | |
| Liver microsome stability ($t_{1/2}$) | >1 hr | | >1 hr | |
| Mini-Ames test (mutagenicity) | Negative | | Negative | |

Table 2 provides a summary of efficacy studies in vivo in mice, and in rat brain slices, using the 5% DMSO:95% Neobee formulation. Use of 3 (NT-181) showed pigmented urine due to the color of the compound itself. Pigmented urine was not seen with 17 (NT-102). Injection issues with the Neobee oil formulation were observed. The injection was reformulated with Miglyol840 oil mix and a lower $EC_{50}$ was observed.

TABLE 4

Summary of efficacy studies in vivo in mice, and in rat brain slices, using the 5% DMSO: 95% Neobee formulation.

| | Number of Animals Protected | |
|---|---|---|
| Model tested | NT-181 | NT-102 |
| 6 Hz mouse seizure model, 22 mA | 8/8 at 100 mg/kg | 8/8 at 400 mg/kg |
| Time of Peak Effect | 0.5 hours | 0.25 hours |
| Effective Dose | 80.60 (25-100) mg/kg | 209.05 (25-400) mg/kg |
| 6 Hz mouse seizure model, 32 mA | 0/7 at 100 mg/kg; 3/8 at 300 mg/kg | 2/8 at 400 mg/kg |
| 6 Hz mouse seizure model, 44 mA | 0/8 at 100 mg/kg | |
| Neurotoxicity (Rotorod assay) | 1/71 showed toxicity | 0/72 showed toxicity |
| Mouse corneal kindled model | 0/8 at 300 mg/kg | 0/24 at 100, 300 and 400 mg/kg |
| Rat in vitro spontaneous electrographic bursting model | 0/8 at 5 uM | 0/9 at 10 uM |

Additional rodent studies showed that compound 17 (NT-102) had efficacy in protecting against electrically-induced seizures, and separate studies were performed to see if NT-102 would affect motor function using the rotarod test in the same mouse or rat. Mice or rats were administered the NT-102 compound i.p., one hour was allowed to pass (since the time to peak effect was determined to be about one hour), and then rodents were then placed on the Rotarod to determine if any motor defects would be observed; after the rotarod test, then rodents were administered an electrical stimulation to determine if the dose of NT-102 would protect against (i.e., prevent) the seizures due to the electrical stimulation. In particular, using (i) electrical model to test for seizures in mice and, separately, (ii) in rat 6 Hz 40V model. More specifically, NT-102 was injected (i.p.) in 5% DMSO/95% Miglyol 840 as vehicle. Mice were challenged with 6 Hz 44 mA current to see if seizures would result. The Effective Dose ($ED_{50}$) of NT-102 to prevent seizures was observed to be 263.74 mg/kg (with a 95% confidence interval of 198.86-321.76 mg/kg). The Time of Peak Effect (TPE) was observed 1 hour. Additional data is shown below in Table 5. The mice were administered the NT-102 at various doses and placed on the rotarod (i.e., "Rotarod (Tox)") to test if the mice would fall off as a model of due to the effects of NT-102; for the "Rotarod(Tox)" results, the "NIT" indicates the number of mice that fell off the rotarod (e.g., for Rotarod(Tox) results, if N/T is 0/8, then zero out of eight mice fell off). For the electrical stimulation data (i.e., "6 Hz 44 mA"), an electrical stimulation of 6 Hz 44 mA was administered. For the 6 Hz 44 mA data, "N/T" refers to the number of mice who were protected against the seizures (e.g., for the 6 Hz 44 mA results if N/T is 4/8, then four out of eight mice tested were protected against the seizures and displayed no seizures due to the electrical current application). Additional electrical dosages and timepoints were tested in mice or rats, as shown in the tables below. The 44 mA electrical dosage was used since it is considered to be a model to test for medication-resistant epilepsy.

TABLE 5

Results with NT-102.

| Test | Dose | Time | N/T |
|---|---|---|---|
| Rotarod (Tox) | 100 mg/kg | 1 hr | 0/8 |
| 6 Hz 44 mA | 100 mg/kg | 1 hr | 0/8 |
| Rotarod (Tox) | 200 mg/kg | 1 hr | 2/8 |
| 6 Hz 44 mA | 200 mg/kg | 1 hr | 2/8 |
| Rotarod (Tox) | 300 mg/kg | 1 hr | 0/8 |
| 6 Hz 44 mA | 300 mg/kg | 1 hr | 4/8 |
| Rotarod (Tox) | 400 mg/kg | 1 hr | 1/8 |
| 6 Hz 44 mA | 400 mg/kg | 1 hr | 8/8 |

A different 32 mA electrical stimulation was used in additional studies with mice, as shown below. Results are shown in Table 6. As expected, a lower ED50 dose was observed of 152.72 mg/kg (with a 95% confidence interval of 98.63-210.98 mg/kg) was observed using this lower amount of electrical stimulation.

TABLE 6

Results with NT-102.

| Test | Dose | Time | N/T |
|---|---|---|---|
| Rotarod (Tox) | 50 mg/kg | 1 hr | 0/8 |
| 6 Hz 32 mA | 50 mg/kg | 1 hr | 0/8 |
| Rotarod (Tox) | 100 mg/kg | 1 hr | 0/8 |
| 6 Hz 32 mA | 100 mg/kg | 1 hr | 4/8 |
| Rotarod (Tox) | 200 mg/kg | 1 hr | 1/8 |
| 6 Hz 32 mA | 200 mg/kg | 1 hr | 3/8 |
| Rotarod (Tox) | 300 mg/kg | 1 hr | 3/8 |
| 6 Hz 32 mA | 300 mg/kg | 1 hr | 7/8 |

Rats were tested using a motor function test (referred to as "MMI(Tox)" to test for minimal motor impairment, as shown in the tables below) using dosages of NT-102 administered i.p., followed by electrical stimulation of 6 Hz 40 V. Time to peak result was observed to be about one hour. Results are shown in Table 7, below.

TABLE 7

Results with NT-102.

| Test | Dose | Time | N/T |
|---|---|---|---|
| MMI (Tox) | 300 mg/kg | 0.25 hr | 0/4 |
| 6 Hz 40 V | 300 mg/kg | 0.25 hr | 3/8 |
| MMI (Tox) | 300 mg/kg | 0.5 hr | 0/4 |
| 6 Hz 40 V | 300 mg/kg | 0.5 hr | 0/8 |
| MMI (Tox) | 300 mg/kg | 1 hr | 0/4 |
| 6 Hz 40 V | 300 mg/kg | 1 hr | 5/8 |
| MMI (Tox) | 300 mg/kg | 2 hr | 0/4 |
| 6 Hz 40 V | 300 mg/kg | 2 hr | 0/4 |
| MMI (Tox) | 300 mg/kg | 4 hr | 0/4 |
| 6 Hz 40 V | 300 mg/kg | 4 hr | 0/4 |

Additional studies with the rat model were performed as shown in Table 8, below. The ED50 in the rats for the 6 Hz 40 V electrical stimulation was observed to be 293 mg/kg (with a 95% confidence interval of 242-441 mg/kg). The 6 Hz 40 V electrical stimulation amount was used because this electrical dosage is considered to be a rat model for medication-resistant epilepsy.

TABLE 8

Results with NT-102.

| Test | Dose | Time | N/T |
| --- | --- | --- | --- |
| 6 Hz 40 V | 200 mg/kg | 1 hr | 1/8 |
| 6 Hz 40 V | 250 mg/kg | 1 hr | 2/8 |
| 6 Hz 40 V | 350 mg/kg | 1 hr | 6/8 |
| MMI (Tox) | 350 mg/kg | 1 hr | 0/8 |

Example 4

Treatment of Parkinson's disease

Figure 6:
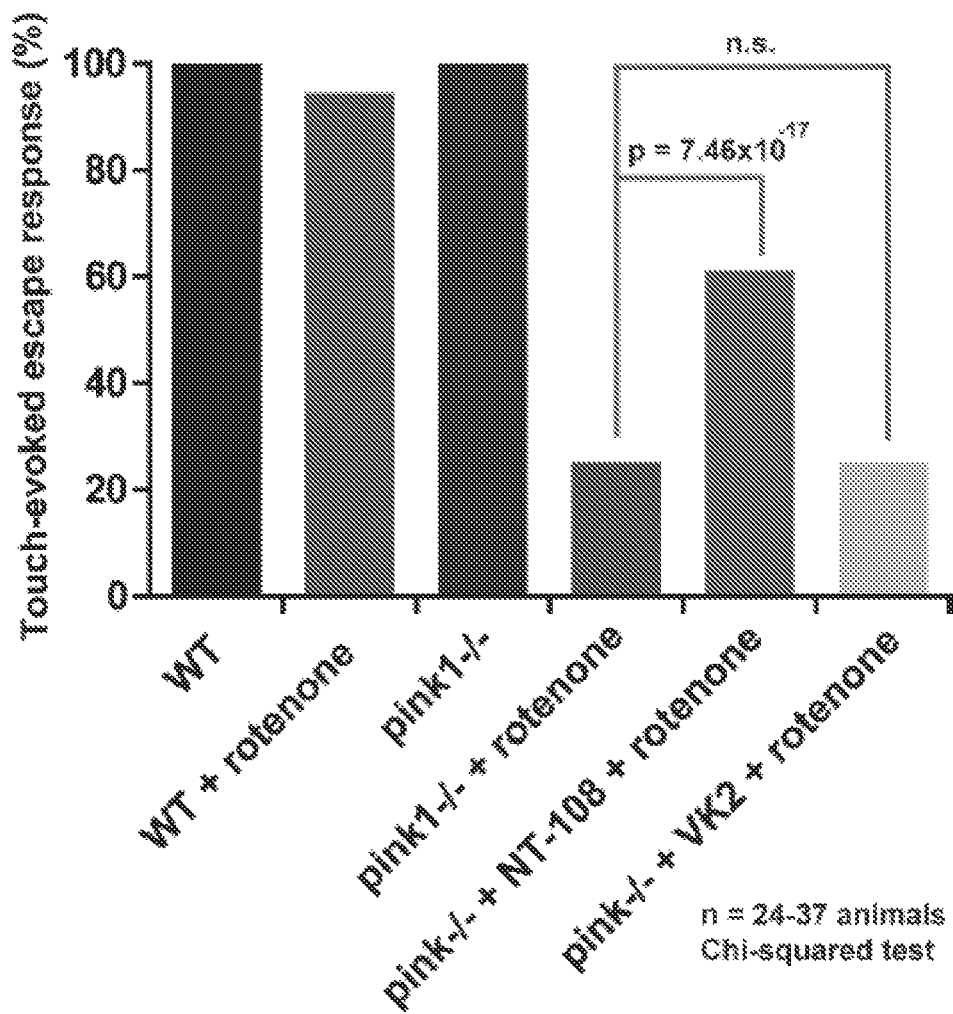
FIG. 6: In vivo results for treatment of Parkinson's disease (PD) using the Pink1 mutant zebrafish model using NT-108. "VK2" refers to the naturally occurring Vitamin K2.

Pink1 mutant zebrafish were obtained from Dr. Daniel Hesselson from the Garvan Institute, Sydney, Australia. His paper in Cell Chemical Biology (2017) outlines the phenotypic screening strategy; one of these factors tested is touch-evoked escape response—young zebrafish are placed in multi-well plates and incubated with a mitochondrial toxin, rotenone. WT zebrafish with or without rotenone treatment, as well as untreated pink−/− zebrafish are able to react to a touch to their tail by the investigator. However, pink1−/− zebrafish treated with rotenone have a significantly dampened touch response, which is rescued by pretreatment with 1 µM 1st generation VK analog NT-108. While one concentration has been tested, the 2nd-generation VK analogs are being tested on this animal model of Parkinson's. Results are shown in FIG. 6.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,399,363
U.S. Pat. No. 5,466,468
U.S. Pat. No. 5,543,158
U.S. Pat. No. 5,580,579
U.S. Pat. No. 5,629,001
U.S. Pat. No. 5,641,515
U.S. Pat. No. 5,725,871
U.S. Pat. No. 5,756,353
U.S. Pat. No. 5,780,045
U.S. Pat. No. 5,792,451
U.S. Pat. No. 5,804,212
U.S. Pat. No. 6,613,308
Adin and Fleming, CO(III) Complex containing radiation sensitive element with diazo recording layer. Eastman Kodak Co., U.S. Pat. No. 4,195,998A, 1980.
Albrecht et al., Mechanisms of oxidative glutamate toxicity: the glutamate/cystine antiporter system xc- as a neuroprotective drug target. CNS Neurol Disord Drug Targets; 9(3):373-82, 2010.
Alsdorf and Wyszynski, Teratogenicity of sodium valproate. Expert Opin Drug Saf.; 4(2):345-53, 2005.
Anderson, Practical Process Research & Development—A Guide for Organic Chemists, $2^{nd}$ ed., Academic Press, New York, 2012.
Andreux et al., A method to identify and validate mitochondrial modulators using mammalian cells and the worm C. elegans. Sci Rep; 4:5285; 2014.
Andreux et al., Pharmacological approaches to restore mitochondrial function. Nat Rev Drug Discov; 12(6):465-83; 2013.
Artuso et al., Mitochondrial DNA metabolism in early development of zebrafish (Danio rerio). Biochim Biophys Acta.; 1817(7):1002-11, 2012.
Baraban et al., Pentylenetetrazole induced changes in zebrafish behavior, neural activity and c-fos expression. Neuroscience. 2005; 131(3):759-68; 2005.
Barton et al., Pharmacological characterization of the 6 Hz psychomotor seizure model of partial epilepsy. Epilepsy Res; 47(3):217-27, 2001.
Bialer and White, Key factors in the discovery and development of new antiepileptic drugs. Nat Rev Drug Discov.; 9(1):68-82, 2010.
Bindoff and Engelsen BA. Mitochondrial diseases and epilepsy. Epilepsia.; 53:92-7, 2012.
Bindoff and Engelsen, Mitochondrial cytopathies. In: Andermann F, Guerrini R, Shorvon S D, editors. The Causes of Epilepsy: Common and Uncommon Causes in Adults and Children. Cambridge: Cambridge University Press; p. 147-57, 2011.
Broughton et al., The complete sequence of the zebrafish (Danio rerio) mitochondrial genome and evolutionary patterns in vertebrate mitochondrial DNA. Genome Res.; 11(11):1958-67, 2001.
Cheng et al., Retinoic acid protects against proteasome inhibition associated cell death in SH-SY5Y cells via the AKT pathway. Neurochem Int.; 62(1):31-42, 2013.
Fei et al., Azaanthraquinone assembly from N-propargylamino quinone via iodine-induced 6-endo-dig electrophilic cyclization. Org Biomol Chem.; 8(18):4096-103, 2010.
Fei et al., CuCl2-promoted 6-endo-dig chlorocyclization and oxidative aromatization cascade: efficient construction of 1-azaanthraquinones from N-propargylaminoquinones. Org Lett.; 13(16):4208-11, 2011.
Fieser and Fieser, The Reduction Potentials of Various Naphthoquinones. J Am Chem Soc.; 57(3):491-4, 1935.
Fieser, THE ALKYLATION OF HYDROXYNAPHTHOQUINONE I. ORTHO-ETHERS. J Am Chem Soc.; 48(11):2922-37, 1926.
Finsterer and Scorza, Effects of antiepileptic drugs on mitochondrial functions, morphology, kinetics, biogenesis, and survival. Epilepsy Res.; 136:5-11, 2017.
Finsterer and Segall, Drugs interfering with mitochondrial disorders. Drug Chem Toxicol.; 33(2):138-5, 2010.

Fleming et al., Functional characterisation of the maturation of the blood-brain barrier in larval zebrafish. PLoS One; 8(10):e77548, 2013.

Franco et al., Challenges in the clinical development of new antiepileptic drugs. Pharmacol Res.; 103:95-104, 2016.

CN 101712648B. Synthesis method of azepine anthraquinone, 2010.

Gornostaev et al., Synthesis of 13-alkylbenzo[f]isochromeno[4,3-b]indole-5,7,12(13H)-triones by reaction of 2-alkylamino-1,4-naphthoquinones with ninhydrin. Russian Journal of Organic Chemistry; 52(1):80-6, 2016.

Ha and Park, Glutamate-induced oxidative stress, but not cell death, is largely dependent upon extracellular calcium in mouse neuronal HT22 cells. Neurosci Lett.; 393(2-3): 165-9, 2006.

*Handbook of Pharmaceutical Salts: Properties, and Use,* Stahl and Wermuth Eds., Verlag Helvetica Chimica Acta, 2002.

Hansen et al., Anticonvulsant and antiepileptogenic effects of GABAA receptor ligands in pentylenetetrazole-kindled mice. Prog Neuropsychopharmacol Biol Psychiatry; 28(1):105-13, 2004.

Howe et al., The zebrafish reference genome sequence and its relationship to the human genome. Nature; 496(7446): 498-503, 2013.

Hwang et al., 1998.

Jeong et al., Functional and developmental analysis of the blood-brain barrier in zebrafish. Brain Res Bull.; 75(5): 619-28. Epub 2008/03/22. doi: 10.1016/j.brainresbull.2007.10.043. PubMed PMID: 18355638, 2008.

Jiang and Wang, Gold(III)-Catalyzed 1,4-Nucleophilic Addition: Facile Approach to Prepare 2-Amino-1,4-naphthalenedione and 6-Amino-5,8-quinolinedione Derivatives. Synlett.; 2009(07): 1099-102, 2009.

Jiang et al., Azaanthraquinonc Assembly from N-Propargylamino Quinone via a Au(I)-Catalyzed 6-endo-dig Cycloisomerization. J Org Chem.; 75(12):4323-5, 2010.

Josey et al., Structure-activity relationship study of vitamin k derivatives yields highly potent neuroprotective agents. J Med Chem; 56(3):1007-22, 2013.

Kimmel et al., Stages of embryonic development of the zebrafish. Dev Dyn.; 203(3):253-310, 1995.

Kumar et al., Synthesis of pharmacologically important naphthoquinones and anticancer activity of 2-benzyllawsone through DNA topoisomerase-II inhibition. Bioorg Med Chem.; 25(4):1364-73, 2017.

Lewerenz et al., Activation of stimulatory heterotrimeric G proteins increases glutathione and protects neuronal cells against oxidative stress. J Neurochem.; 87(2):522-31, 2003.

Lewerenz et al., Induction of Nrf2 and xCT are involved in the action of the neuroprotective antibiotic ceftriaxone in vitro. J Neurochem.; 111(2):332-43, 2009.

Lheureux and Hantson, Carnitine in the treatment of valproic acid-induced toxicity. Clin Toxicol (Phila).; 47(2): 101-11, 2009.

Lien et al., cSynthesis of 2-alkoxy 1,4-naphthoquinone derivatives as antiplatelet, antiinflammatory, and antiallergic agents. Chem Pharm Bull (Tokyo); 50(5):672-4, 2002.

Loscher and Schmidt, Modern antiepileptic drug development has failed to deliver: ways out of the current dilemma. Epilepsia.; 52(4):657-78, 2011.

Loscher et al., New avenues for anti-epileptic drug discovery and development. Nat Rev Drug Discov.; 12(10):757-76, 2013.

Maher and Davis, The role of monoamine metabolism in oxidative glutamate toxicity. J Neurosci.; 16(20):6394-401, 1996.

Matagne and Klitgaard, Validation of corneally kindled mice: a sensitive screening model for partial epilepsy in man. Epilepsy Res; 31(1):59-71, 1998.

Mathiowitz et al., 1997.

Matsumoto et al., Secondary elevation of extracellular neurotransmitter amino acids in the reperfusion phase following focal cerebral ischemia. J Cereb Blood Flow Metab.; 16(1):114-24, 1996.

Metcalf et al., Development and pharmacologic characterization of the rat 6 Hz model of partial seizures. Epilepsi; 58(6):1073-84, 2017.

Milton et al., Rational design of quinones for high power density biofuel cells. Chem Sci.; 6(8):4867-75, 2015.

Mohanraj and Brodie, Outcomes in newly diagnosed localization-related epilepsies. Seizure; 14(5):318-23, 2005.

Morimoto and Koshland, Induction and expression of long- and short-term neurosecretory potentiation in a neural cell line. Neuron.; 5(6):875-80, 1990.

Nadanaciva et al., Toxicity assessments of nonsteroidal anti-inflammatory drugs in isolated mitochondria, rat hepatocytes, and zebrafish show good concordance across chemical classes. Toxicol Appl Pharmacol., 2013.

Noebels et al., Jasper's Basic Mechanisms of the Epilepsies. 4th edition ed. Bethesda (MD): National Center for Biotechnology Information (US); 2012.

Nogueira et al., "Syndromes associated with mitochondrial DNA depletion." *Ital J Pediatr.,* 40:34, 2014.

Novel tetracyclonaphthooxazole derivative and preparation method thereof, 2015.

Ogata et al., Unusual, chemoselective etherification of 2-hydroxy-1,4-naphthoquinone derivatives utilizing alkoxymethyl chlorides: scope, mechanism and application to the synthesis of biologically active natural product (±)-lantalucratin C. Tetrahedron; 72(11):1423-32, 2016.

Ohlow et al., Why Have Clinical Trials of Antioxidants to Prevent Neurodegeneration Failed?—A Cellular Investigation of Novel Phenothiazine-Type Antioxidants Reveals Competing Objectives for Pharmaceutical Neuroprotection. Pharm Res.; 34(2):378-93, 2017.

Peng et al., A 96-Well Screen Filter Plate for High-Throughput Biological Sample Preparation and LC-MS/MS Analysis. Analytical Chemistry; 78(1):343-8, 2006a.

Peng et al., Fully Automated 96-Well Liquid—Liquid Extraction for Analysis of Biological Samples by Liquid Chromatography with Tandem Mass Spectrometry. Analytical Chemistry.; 73(3):708-14, 2001.

Peng et al., Improved pharmacokinetic and bioavailability support of drug discovery using serial blood sampling in mice. Journal of pharmaceutical sciences; 98(5):1877-84, 2009.

Peng et al., Particulate separation filters and methods. Google Patents; 2006b.

Perucca, Pharmacological and therapeutic properties of valproate: a summary after 35 years of clinical experience. CNS Drugs.; 16(10):695-714, 2002.

Petrova et al., Electrochemical properties of some naturally occurring quinoncs. Journal of electroanalytical chemistry and interfacial electrochemistry; 277(1-2):189-96, 1990.

Poteet et al., Neuroprotective actions of methylene blue and its derivatives. PLoS One; 7(10):e48279, 2012.

Practical Process Research & Development, 2012.

Rahn et al., Novel Vitamin K analogs suppress seizures in zebrafish and mouse models of epilepsy. Neuroscience. 2014; 259C:142-54, 2013.

Rahn et al., Novel Vitamin K analogs suppress seizures in zebrafish and mouse models of epilepsy. Neuroscience; 259C:142-54, 2014.

Reagan-Shaw et al., FASEB J., 22(3):659-661, 2008.

Remington: The Science and Practice of Pharmacy, 21st Ed. Lippincott Williams and Wilkins, 2005.

Remington's Pharmaceutical Sciences, 15th Edition, pages 1035-1038 and 1570-1580, 1975.

Remington's Pharmaceutical Sciences, 18th Ed. Mack Printing Company, pp. 1289-1329, 1990.

Rowley and White, Comparative anticonvulsant efficacy in the corneal kindled mouse model of partial epilepsy: Correlation with other seizure and epilepsy models. Epilepsy Res.; 92(2-3):163-9, 2010.

Sagara and Schubert, The activation of metabotropic glutamate receptors protects nerve cells from oxidative stress. J Neurosci.; 18(17):6662-71, 1998.

Schriml et al., Human Disease Genes and Their Cloned Mouse Orthologs: Exploration of the FANTOM2 cDNA Sequence Data Set. Genome Research; 13(6b):1496-500, 2003.

Schubert and Maher, An alternative approach to drug discovery for Alzheimer's disease dementia. Future Med Chem.; 4(13):1681-8, 2012.

Smith, March's Advanced Organic Chemistry: Reactions, Mechanisms, and Structure, 7th Ed., Wiley, 2013.

Sreelatha et al., Synthesis and SAR study of novel anticancer and antimicrobial naphthoquinone amide derivatives. Bioorg Med Chem Lett.; 24(15):3647-51, 2014.

Stables and Kupferberg, The NIH anticonvulsant drug development (ADD) program: preclinical anticonvulsant. Molecular and cellular targets for anti-epileptic drugs; 12:191, 1997.

Stables et al., Therapy discovery for pharmacoresistant epilepsy and for disease-modifying therapeutics: summary of the NIH/NINDS/AES models II workshop. Epilepsia; 44(12):1472-8, 2003.

Stewart et al., Polymerase gamma gene POLG determines the risk of sodium valproate-induced liver toxicity. Hepatology.; 52(5):1791-6, 2010.

Takenaga et al., 1998.

Tan et al., Oxytosis: A novel form of programmed cell death. Curr Top Med Chem.; 1(6):497-506, 2001.

Tandon et al., Synthesis and evaluation of novel 1,4-naphthoquinone derivatives as antiviral, antifungal and anticancer agents. Bioorg Med Chem Lett; 14(11):2901-4, 2004.

Tobaben et al., Bid-mediated mitochondrial damage is a key mechanism in glutamate-induced oxidative stress and AIF-dependent cell death in immortalized HT-22 hippocampal neurons. Cell Death Differ.; 18(2):282-92, 2011.

Vafai et al., Natural Product Screening Reveals Naphthoquinone Complex I Bypass Factors. PLoS One; 11(9): e0162686, 2016.

Valente et al., The 1,4-naphthoquinone scaffold in the design of cysteine protease inhibitors. Bioorg Med Chem; 15(15):5340-50, 2007.

van Leyen et al., Novel lipoxygenase inhibitors as neuroprotective reagents. J Neurosci Res.; 86(4):904-9, 2008.

van Leyen et al., Proteasome inhibition protects HT22 neuronal cells from oxidative glutamate toxicity. J Neurochem.; 92(4):824-30, 2005.

Wang et al., Naphthoquinone-directed C—H annulation and C(sp(3))-H bond cleavage: one-pot synthesis of tetracyclic naphthoxazoles. J Org Chem.; 79(10):4553-60, 2014.

Wang et al., Synthesis and Biological Evaluation of Lipophilic 1,4-Naphthoquinone Derivatives against Human Cancer Cell Lines. Molecules; 20(7):11994-2015, 2015.

Watanabe et al., In vivo assessment of the permeability of the blood-brain barrier and blood-retinal barrier to fluorescent indoline derivatives in zebrafish. BMC Neurosci.; 13(1): 101, 2012.

Wen et al., Alternative mitochondrial electron transfer as a novel strategy for neuroprotection. J Biol Chem.; 286(18): 16504-15, 2011.

Westerfield, The zebrafish book. A guide for the laboratory use of zebrafish (Danio rerio). 4th ed. Eugene: University of Oregon Press; 2000.

Xie et al., A novel transgenic zebrafish model for bloodbrain and blood-retinal barrier development. BMC Dev Biol.; 10:76, 2010.

Yang et al., The excitatory neurotransmitter glutamate stimulates DNA repair to increase neuronal resiliency. Mech Ageing Dev.; 132(8-9):405-11, 2011.

What is claimed is:

1. A method of treating epilepsy in a mammalian subject comprising administering to a subject a therapeutically effective dose of a pharmaceutical composition comprising a compound of the formula:

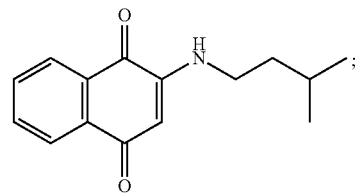 [SMILES: CC(C)CCNC1=CC(=O)c2ccccc2C1=O]

or a pharmaceutically acceptable salt thereof.

2. The method of claim 1, wherein the epilepsy is medication-resistant epilepsy.

3. The method of claim 1, wherein the pharmaceutical composition is administered orally, sublingually, intranasally, intravenously, subcutaneously, parenterally, via inhalation or aerosol or the subject is a human.

4. The method of claim 1, wherein the compound is further defined as:

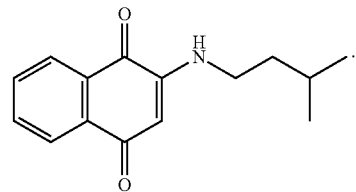

5. The method of claim 1, wherein the compound is formulated with a pharmaceutically acceptable excipient.

* * * * *